(12) United States Patent
Yayon et al.

(10) Patent No.: US 9,226,949 B2
(45) Date of Patent: Jan. 5, 2016

(54) FGF-18 TRUNCATED VARIANTS HAVING INCREASED RECEPTOR SPECIFICITY AND USES THEREOF

(71) Applicant: HEPACORE LTD., Ness Ziona (IL)

(72) Inventors: Avner Yayon, Moshav Sitria (IL); Eran Rom, Rehovot (IL); Roy Sirkis, Ness Ziona (IL); Dalit Strauss-Ayali, Sde Warburg (IL)

(73) Assignee: HEPACORE LTD., Ness Ziona (IL)

(*) Notice: Subject to any disclaimer, the term of this patent is extended or adjusted under 35 U.S.C. 154(b) by 0 days.

(21) Appl. No.: 13/848,569

(22) Filed: Mar. 21, 2013

(65) Prior Publication Data

US 2013/0225493 A1 Aug. 29, 2013

Related U.S. Application Data

(63) Continuation of application No. PCT/IL2011/000731, filed on Sep. 14, 2011.

(60) Provisional application No. 61/384,766, filed on Sep. 21, 2010.

(51) Int. Cl.
*A61K 38/18* (2006.01)
*C07K 14/50* (2006.01)
*A61K 45/06* (2006.01)

(52) U.S. Cl.
CPC .............. *A61K 38/1825* (2013.01); *A61K 45/06* (2013.01); *C07K 14/50* (2013.01)

(58) Field of Classification Search
None
See application file for complete search history.

(56) References Cited

U.S. PATENT DOCUMENTS

| 5,512,460 | A | 4/1996 | Nauro et al. |
| 5,571,895 | A | 11/1996 | Kurokawa et al. |
| 5,998,170 | A | 12/1999 | Arakawa et al. |
| 2004/0014658 | A1 | 1/2004 | Bogin et al. |
| 2008/0193425 | A1 | 8/2008 | Ellsworth |
| 2009/0247462 | A1 | 10/2009 | Bogin et al. |
| 2009/0286965 | A1 | 11/2009 | Imamura et al. |
| 2010/0016223 | A1 | 1/2010 | Gimona et al. |
| 2013/0225493 | A1 * | 8/2013 | Yayon et al. ................... 514/9.1 |

FOREIGN PATENT DOCUMENTS

| WO | 0139788 A2 | 6/2001 |
| WO | 0236732 A2 | 5/2002 |
| WO | 03094835 A2 | 11/2003 |
| WO | 2006063362 A1 | 6/2006 |
| WO | WO 2007080847 A1 * | 7/2007 |
| WO | 2007144893 A2 | 12/2007 |
| WO | 2008038287 A2 | 4/2008 |
| WO | 2008081463 A2 | 7/2008 |

OTHER PUBLICATIONS

Mohammadi et al. Structural basis for fibroblast growth factor receptor activation. Cytokine Growth Factor Rev. Apr. 2005;16(2):107-37.*
Aikawa et al., (2001) Fibroblast growth factor inhibits chondrocytic growth through induction of p21 and subsequent inactivation of cyclin E-Cdk2. J Biol Chem 276(31): 29347-29352.
Bellosta et al., (2001) Identification of receptor and heparin binding sites in fibroblast growth factor 4 by structure-based mutagenesis. Mol Cell Biol 21(17): 5946-5957.
Blesch et al., (1994) Cloning of a novel malignant melanoma-derived growthregulatory protein, MIA. Cancer Res 54 (21): 5695-5701.
Bosserhoff and Buettner (2003) Establishing the protein MIA (melanoma inhibitory activity) as a marker for chondrocyte differentiation. Biomaterials 24(19): 3229-3234.
Chusho et al., (2001) Dwarfism and early death in mice lacking C-type natriuretic peptide. Proc Natl Acad Sci USA 98 (7): 4016-4021.
Davidson et al., (2005) Fibroblast growth factor (FGF) 18 signals through FGF receptor 3 to promote chondrogenesis. J Biol Chem 280(21): 20509-20515.
Dietz and Sandell (1996) Cloning of a retinoic acid-sensitive mRNA expressed in cartilage and during chondrogenesis. J Biol Chem 271(6): 3311-3316.
Hamidouche et al., (2010) Autocrine fibroblast growth factor 18 mediates dexamethasone-induced osteogenic differentiation of murine mesenchymal stem cells. J Cell Physiol 224(2): 509-515.
Hoshikawa et al., (2002) FGF-18 is a neuron-derived glial cell growth factor expressed in the rat brain during early postnatal development. Brain Res Mol Brain Res 105(1-2): 60-66.
Hu et al., (1998) FGF-18, a novel member of the fibroblast growth factor family, stimulates hepatic and intestinal proliferation. Mol Cell Biol 18(10): 6063-6074.
Imamura et al., (1990) Recovery of mitogenic activity of a growth factor mutant with a nuclear translocation sequence. Science 249(4976): 1567-1570.
Jang et al., (2001) Mutations in fibroblast growth factor receptor 2 and fibroblast growth factor receptor 3 genes associated with human gastric and colorectal cancers. Cancer Res 61(9): 3541-3543.
Katoh (2008) Cancer genomics and genetics of FGFR2 (Review). Int J Oncol 33(2): 233-237.
Krejci et al., (2005) Interaction of fibroblast growth factor and C-natriuretic peptide signaling in regulation of chondrocyte proliferation and extracellular matrix homeostasis. J Cell Sci 118(Pt 21): 5089-5100.

(Continued)

*Primary Examiner* — David Romeo
(74) *Attorney, Agent, or Firm* — Vorys, Sater, Seymour and Pease LLP

(57) ABSTRACT

The present invention relates to fibroblast growth factor 18 (FGF-18) variants having various truncations beyond the signal peptide domain of the N-terminus, which activate FGFR3 with increased specificity. The invention further relates to polynucleotides encoding the variants, pharmaceutical compositions comprising same and methods for use thereof in treating cartilage and skeletal disorders.

20 Claims, 16 Drawing Sheets

(56) References Cited

OTHER PUBLICATIONS

Kuroda et al., (1999) Anabolic effect of aminoterminally truncated fibroblast growth factor 4 (FGF4) on bone. Bone 25 (4): 431-437.

Liu et al., (2002) Hyaluronate-heparin conjugate gels for the delivery of basic fibroblast growth factor (FGF-2). J Biomed Mater Res 62(1): 128-135.

Miyaoka et al, (2010) A novel regulatory mechanism for Fgf18 signaling involving cysteine-rich FGF receptor (Cfr) and delta-like protein (Dlk). Development 137(1): 159-167.

Miyazawa et al., (2002) Cyclic GMP-dependent protein kinase II plays a critical role in C-type natriuretic peptide-mediated endochondral ossification. Endocrinology 143(9): 3604-3610.

Mohammadi et al., (2005) Structural basis for fibroblast growth factor receptor activation. Cytokine Growth Factor Rev 16(2): 107-137.

Olsen et al., (2004) Insights into the molecular basis for fibroblast growth factor receptor autoinhibition and ligand-binding promiscuity. PNAS 101(4): 935-940.

Ornitz (2000) FGFs, heparan sulfate and FGFRs: complex interactions essential for development. Bioessays 22: 108-112.

Ornitz and Itoh (2001) Fibroblast growth factors. Gen Biol 2(3): 30005.1-3005.12.

Ozasa et al., (2005) Complementary antagonistic actions between C-type natriuretic peptide and the MAPK pathway through FGFR-3 in ATDC5 cells. Bone 36(6): 1056-1064.

Plotnikov et al., (2000) Crystal structures of two FGF-FGFR complexes reveal the determinants of ligand-receptor specificity. Cell 101: 413-424.

Seno et al., (1990) Carboxyl-terminal structure of basic fibroblast growth factor significantly contributes to its affinity for heparin. Eur J Biochem 188(2): 239-245.

Sonvilla et al., (2010) Fibroblast growth factor receptor 3-IIIc mediates colorectal cancer growth and migration. Br J Cancer 102(7): 1145-1156.

Tamura et al., (2004) Critical roles of the guanylyl cyclase B receptor in endochondral ossification and development of female reproductive organs. PNAS 101(49): 17300-17305.

Tanaka et al., (1995) Human androgen-induced growth factor in prostate and breast cancer cells: its molecular cloning and growth properties. FEBS Lett 363(3): 226-230.

Zhang et al., (2006) Receptor specificity of the fibroblast growth factor family. The complete mammalian FGF family. J Biol Chem 281(23): 15694-15700.

International Search Report Application No. PCT/IL2011/000731 Completed: Jul. 9, 2012; Mailing Date: Jul. 27, 2012 13 pages.

* cited by examiner

SEQ ID NO: 1

MYSAPSACTCLCLHFLLLCFQVQVLVAEENVDFRIHVENQTRARDDVSRKQ
LRLYQLYSRTSGKHIQVLGRRISARGEDGDKYAQLLVETDTFGSQVRIKGK
ETEFYLCMNRKGKLVGKPDGTSKECVFIEKVLENNYTALMSAKYSGWYVGF
TKKGRPRKGPKTRENQQDVHFMKRYPKGQPELQKPFKYTTVTKRSRRIRPT
HPA

SEQ ID NO: 2

MENVDFRIHVENQTRARDDVSRKQLRLYQLYSRTSGKHIQVLGRRISARGE
DGDKYAQLLVETDTFGSQVRIKGKETEFYLCMNRKGKLVGKPDGTSKECVF
IEKVLENNYTALMSAKYSGWYVGFTKKGRPRKGPKTRENQQDVHFMKRYPK
GQPELQKPFKYTTVTKRSRRIRPTHPA

Figure 1

SEQUENCE LISTING

```
<160> NUMBER OF SEQ ID NOS: 71

<210> SEQ ID NO 1
<211> LENGTH: 207
<212> TYPE: PRT
<213> ORGANISM: Homo sapiens

<400> SEQUENCE: 1

Met Tyr Ser Ala Pro Ser Ala Cys Thr Cys Leu Cys Leu His Phe Leu
1               5                   10                  15

Leu Leu Cys Phe Gln Val Gln Val Leu Val Ala Glu Glu Asn Val Asp
                20                  25                  30

Phe Arg Ile His Val Glu Asn Gln Thr Arg Ala Arg Asp Asp Val Ser
            35                  40                  45

Arg Lys Gln Leu Arg Leu Tyr Gln Leu Tyr Ser Arg Thr Ser Gly Lys
        50                  55                  60

His Ile Gln Val Leu Gly Arg Arg Ile Ser Ala Arg Gly Glu Asp Gly
65                  70                  75                  80

Asp Lys Tyr Ala Gln Leu Leu Val Glu Thr Asp Thr Phe Gly Ser Gln
                85                  90                  95
```

```
Val Arg Ile Lys Gly Lys Glu Thr Glu Phe Tyr Leu Cys Met Asn Arg
            100                 105                 110

Lys Gly Lys Leu Val Gly Lys Pro Asp Gly Thr Ser Lys Glu Cys Val
        115                 120                 125

Phe Ile Glu Lys Val Leu Glu Asn Asn Tyr Thr Ala Leu Met Ser Ala
130                 135                 140

Lys Tyr Ser Gly Trp Tyr Val Gly Phe Thr Lys Lys Gly Arg Pro Arg
145                 150                 155                 160

Lys Gly Pro Lys Thr Arg Glu Asn Gln Gln Asp Val His Phe Met Lys
                165                 170                 175

Arg Tyr Pro Lys Gly Gln Pro Glu Leu Gln Lys Pro Phe Lys Tyr Thr
            180                 185                 190

Thr Val Thr Lys Arg Ser Arg Arg Ile Arg Pro Thr His Pro Ala
            195                 200                 205

<210> SEQ ID NO 2
<211> LENGTH: 180
<212> TYPE: PRT
<213> ORGANISM: Artificial Sequence
<220> FEATURE:
<223> OTHER INFORMATION: Synthetic polypeptide

<400> SEQUENCE: 2

Met Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala
        35                  40                  45

Arg Gly Glu Asp Gly Asp Lys Tyr Ala Gln Leu Leu Val Glu Thr Asp
    50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
    130                 135                 140

Val His Phe Met Lys Arg Tyr Pro Lys Gly Gln Pro Glu Leu Gln Lys
145                 150                 155                 160

Pro Phe Lys Tyr Thr Thr Val Thr Lys Arg Ser Arg Arg Ile Arg Pro
                165                 170                 175

Thr His Pro Ala
            180

<210> SEQ ID NO 3
<211> LENGTH: 179
<212> TYPE: PRT
<213> ORGANISM: Artificial Sequence
<220> FEATURE:
<223> OTHER INFORMATION: Synthetic polypeptide

<400> SEQUENCE: 3

Met Asn Val Asp Phe Arg Ile His Val Glu Asn Gln Thr Arg Ala Arg
```

```
            1               5                  10                  15
Asp Asp Val Ser Arg Lys Gln Leu Arg Leu Tyr Gln Leu Tyr Ser Arg
            20                  25                  30
Thr Ser Gly Lys His Ile Gln Val Leu Gly Arg Arg Ile Ser Ala Arg
            35                  40                  45
Gly Glu Asp Gly Asp Lys Tyr Ala Gln Leu Leu Val Glu Thr Asp Thr
    50                  55                  60
Phe Gly Ser Gln Val Arg Ile Lys Gly Lys Glu Thr Glu Phe Tyr Leu
65                  70                  75                  80
Cys Met Asn Arg Lys Gly Lys Leu Val Gly Lys Pro Asp Gly Thr Ser
                85                  90                  95
Lys Glu Cys Val Phe Ile Glu Lys Val Leu Glu Asn Asn Tyr Thr Ala
            100                 105                 110
Leu Met Ser Ala Lys Tyr Ser Gly Trp Tyr Val Gly Phe Thr Lys Lys
            115                 120                 125
Gly Arg Pro Arg Lys Gly Pro Lys Thr Arg Glu Asn Gln Gln Asp Val
    130                 135                 140
His Phe Met Lys Arg Tyr Pro Lys Gly Gln Pro Glu Leu Gln Lys Pro
145                 150                 155                 160
Phe Lys Tyr Thr Thr Val Thr Lys Arg Ser Arg Arg Ile Arg Pro Thr
                165                 170                 175
His Pro Ala

<210> SEQ ID NO 4
<211> LENGTH: 540
<212> TYPE: DNA
<213> ORGANISM: Artificial Sequence
<220> FEATURE:
<223> OTHER INFORMATION: Synthetic polynucleotide

<400> SEQUENCE: 4
atgaacgtgg acttccgcat ccacgtggag aaccagacgc gggctcggga cgatgtgagc      60
cgtaagcagc tgcggctgta ccagctctac agccggacca gtgggaaaca catccaggtc     120
ctgggccgca ggatcagtgc ccgcggcgag gatggggaca gtatgcccca gctcctagtg     180
gagacagaca ccttcggtag tcaagtccgg atcaagggca aggagacgga attctacctg     240
tgcatgaacc gcaaaggcaa gctcgtgggg aagcccgatg caccagcaa ggagtgtgtg      300
ttcatcgaga aggttctgga gaacaactac acggccctga tgtcggctaa gtactccggc     360
tggtacgtgg gcttcaccaa gaaggggcgg ccgcggaagg gccccaagac ccgggagaac     420
cagcaggacg tgcatttcat gaagcgctac cccaaggggc agccggagct tcagaagccc     480
ttcaagtaca cgacggtgac caagaggtcc cgtcggatca ggcccacaca ccctgcctag     540

<210> SEQ ID NO 5
<211> LENGTH: 178
<212> TYPE: PRT
<213> ORGANISM: Artificial Sequence
<220> FEATURE:
<223> OTHER INFORMATION: Synthetic polypeptide

<400> SEQUENCE: 5

Met Val Asp Phe Arg Ile His Val Glu Asn Gln Thr Arg Ala Arg Asp
1               5                   10                  15
Asp Val Ser Arg Lys Gln Leu Arg Leu Tyr Gln Leu Tyr Ser Arg Thr
            20                  25                  30
Ser Gly Lys His Ile Gln Val Leu Gly Arg Arg Ile Ser Ala Arg Gly
```

```
            35                  40                  45
Glu Asp Gly Asp Lys Tyr Ala Gln Leu Leu Val Glu Thr Asp Thr Phe
 50                  55                  60

Gly Ser Gln Val Arg Ile Lys Gly Lys Glu Thr Glu Phe Tyr Leu Cys
 65                  70                  75                  80

Met Asn Arg Lys Gly Lys Leu Val Gly Lys Pro Asp Gly Thr Ser Lys
                 85                  90                  95

Glu Cys Val Phe Ile Glu Lys Val Leu Glu Asn Asn Tyr Thr Ala Leu
            100                 105                 110

Met Ser Ala Lys Tyr Ser Gly Trp Tyr Val Gly Phe Thr Lys Lys Gly
            115                 120                 125

Arg Pro Arg Lys Gly Pro Lys Thr Arg Glu Asn Gln Gln Asp Val His
        130                 135                 140

Phe Met Lys Arg Tyr Pro Lys Gly Gln Pro Leu Gln Lys Pro Phe
145                 150                 155                 160

Lys Tyr Thr Thr Val Thr Lys Arg Ser Arg Arg Ile Arg Pro Thr His
                165                 170                 175

Pro Ala

<210> SEQ ID NO 6
<211> LENGTH: 537
<212> TYPE: DNA
<213> ORGANISM: Artificial Sequence
<220> FEATURE:
<223> OTHER INFORMATION: Synthetic polynucleotide

<400> SEQUENCE: 6
atggtggact tccgcatcca cgtggagaac cagacgcggg ctcgggacga tgtgagccgt      60
aagcagctgc ggctgtacca gctctacagc cggaccagtg ggaaacacat ccaggtcctg     120
ggccgcagga tcagtgcccg cggcgaggat ggggacaagt atgcccagct cctagtggag     180
acagacacct tcggtagtca agtccggatc aagggcaagg agacggaatt ctacctgtgc     240
atgaaccgca aaggcaagct cgtggggaag cccgatggca ccagcaagga gtgtgtgttc     300
atcgagaagg ttctggagaa caactacacg gccctgatgt cggctaagta ctccggctgg     360
tacgtgggct tcaccaagaa ggggcggccg cggaagggcc ccaagacccg ggagaaccag     420
caggacgtgc atttcatgaa gcgctacccc aaggggcagc cggagcttca gaagcccttc     480
aagtacacga cggtgaccaa gaggtcccgt cggatcaggc ccacacaccc tgcctag       537

<210> SEQ ID NO 7
<211> LENGTH: 177
<212> TYPE: PRT
<213> ORGANISM: Artificial Sequence
<220> FEATURE:
<223> OTHER INFORMATION: Synthetic polypeptide

<400> SEQUENCE: 7

Met Asp Phe Arg Ile His Val Glu Asn Gln Thr Arg Ala Arg Asp Asp
  1               5                  10                  15

Val Ser Arg Lys Gln Leu Arg Leu Tyr Gln Leu Tyr Ser Arg Thr Ser
                 20                  25                  30

Gly Lys His Ile Gln Val Leu Gly Arg Arg Ile Ser Ala Arg Gly Glu
            35                  40                  45

Asp Gly Asp Lys Tyr Ala Gln Leu Leu Val Glu Thr Asp Thr Phe Gly
 50                  55                  60

Ser Gln Val Arg Ile Lys Gly Lys Glu Thr Glu Phe Tyr Leu Cys Met
```

```
            65                  70                  75                  80
Asn Arg Lys Gly Lys Leu Val Gly Lys Pro Asp Gly Thr Ser Lys Glu
                    85                  90                  95

Cys Val Phe Ile Glu Lys Val Leu Glu Asn Asn Tyr Thr Ala Leu Met
                100                 105                 110

Ser Ala Lys Tyr Ser Gly Trp Tyr Val Gly Phe Thr Lys Lys Gly Arg
                115                 120                 125

Pro Arg Lys Gly Pro Lys Thr Arg Glu Asn Gln Gln Asp Val His Phe
            130                 135                 140

Met Lys Arg Tyr Pro Lys Gly Gln Pro Glu Leu Gln Lys Pro Phe Lys
145                 150                 155                 160

Tyr Thr Thr Val Thr Lys Arg Ser Arg Arg Ile Arg Pro Thr His Pro
                165                 170                 175

Ala

<210> SEQ ID NO 8
<211> LENGTH: 534
<212> TYPE: DNA
<213> ORGANISM: Artificial Sequence
<220> FEATURE:
<223> OTHER INFORMATION: Synthetic polynucleotide

<400> SEQUENCE: 8
atggacttcc gcatccacgt ggagaaccag acgcgggctc gggacgatgt gagccgtaag      60
cagctgcggc tgtaccagct ctacagccgg accagtggga acacatccag gtcctgggc     120 cgcaggatca gtgcccgcgg cgaggatggg acaagtatg cccagctcct agtggagaca     180
gacaccttcg gtagtcaagt ccggatcaag ggcaaggaga cggaattcta cctgtgcatg     240
aaccgcaaag gcaagctcgt ggggaagccc gatggcacca gcaaggagtg tgtgttcatc     300
gagaaggttc tggagaacaa ctacacggcc ctgatgtcgg ctaagtactc cggctggtac     360
gtgggcttca ccaagaaggg gcggccgcgg aagggcccca gacccgggga gaaccagcag     420
gacgtgcatt tcatgaagcg ctaccccaag gggcagccgg agcttcagaa gcccttcaag     480
tacacgacgg tgaccaagag gtcccgtcgg atcaggccca cacccctgc ctag            534

<210> SEQ ID NO 9
<211> LENGTH: 176
<212> TYPE: PRT
<213> ORGANISM: Artificial Sequence
<220> FEATURE:
<223> OTHER INFORMATION: Synthetic polypeptide

<400> SEQUENCE: 9

Met Phe Arg Ile His Val Glu Asn Gln Thr Arg Ala Arg Asp Asp Val
1               5                   10                  15

Ser Arg Lys Gln Leu Arg Leu Tyr Gln Leu Tyr Ser Arg Thr Ser Gly
                20                  25                  30

Lys His Ile Gln Val Leu Gly Arg Arg Ile Ser Ala Arg Gly Glu Asp
            35                  40                  45

Gly Asp Lys Tyr Ala Gln Leu Leu Val Glu Thr Asp Thr Phe Gly Ser
        50                  55                  60

Gln Val Arg Ile Lys Gly Lys Glu Thr Glu Phe Tyr Leu Cys Met Asn
65                  70                  75                  80

Arg Lys Gly Lys Leu Val Gly Lys Pro Asp Gly Thr Ser Lys Glu Cys
                85                  90                  95

Val Phe Ile Glu Lys Val Leu Glu Asn Asn Tyr Thr Ala Leu Met Ser
```

```
              100                 105                 110
Ala Lys Tyr Ser Gly Trp Tyr Val Gly Phe Thr Lys Lys Gly Arg Pro
            115                 120                 125

Arg Lys Gly Pro Lys Thr Arg Glu Asn Gln Gln Asp Val His Phe Met
        130                 135                 140

Lys Arg Tyr Pro Lys Gly Gln Pro Glu Leu Gln Lys Pro Phe Lys Tyr
    145                 150                 155                 160

Thr Thr Val Thr Lys Arg Ser Arg Arg Ile Arg Pro Thr His Pro Ala
                165                 170                 175

<210> SEQ ID NO 10
<211> LENGTH: 531
<212> TYPE: DNA
<213> ORGANISM: Artificial Sequence
<220> FEATURE:
<223> OTHER INFORMATION: Synthetic polynucleotide

<400> SEQUENCE: 10
atgttccgca tccacgtgga gaaccagacg cgggctcggg acgatgtgag ccgtaagcag     60
ctgcggctgt accagctcta cagccggacc agtgggaaac acatccaggt cctgggccgc    120
aggatcagtg cccgcggcga ggatgggggac aagtatgccc agctcctagt ggagacagac   180
accttcggta gtcaagtccg gatcaagggc aaggagacgg aattctacct gtgcatgaac    240
cgcaaaggca agctcgtggg gaagcccgat ggcaccagca ggagtgtgt gttcatcgag     300 aaggttctgg agaacaacta cacggccctg atgtcggcta agtactccgg ctggtacgtg    360
ggcttcacca agaaggggcg gccgcggaag ggccccaaga cccgggagaa ccagcaggac    420
gtgcatttca tgaagcgcta ccccaagggg cagccggagc ttcagaagcc cttcaagtac    480
acgacggtga ccaagaggtc ccgtcggatc aggcccacac ccctgccta g              531

<210> SEQ ID NO 11
<211> LENGTH: 175
<212> TYPE: PRT
<213> ORGANISM: Artificial Sequence
<220> FEATURE:
<223> OTHER INFORMATION: Synthetic polypeptide

<400> SEQUENCE: 11

Met Arg Ile His Val Glu Asn Gln Thr Arg Ala Arg Asp Asp Val Ser
1               5                  10                  15

Arg Lys Gln Leu Arg Leu Tyr Gln Leu Tyr Ser Arg Thr Ser Gly Lys
            20                  25                  30

His Ile Gln Val Leu Gly Arg Arg Ile Ser Ala Arg Gly Glu Asp Gly
        35                  40                  45

Asp Lys Tyr Ala Gln Leu Leu Val Glu Thr Asp Thr Phe Gly Ser Gln
    50                  55                  60

Val Arg Ile Lys Gly Lys Glu Thr Glu Phe Tyr Leu Cys Met Asn Arg
65                  70                  75                  80

Lys Gly Lys Leu Val Gly Lys Pro Asp Gly Thr Ser Lys Glu Cys Val
                85                  90                  95

Phe Ile Glu Lys Val Leu Glu Asn Asn Tyr Thr Ala Leu Met Ser Ala
            100                 105                 110

Lys Tyr Ser Gly Trp Tyr Val Gly Phe Thr Lys Lys Gly Arg Pro Arg
        115                 120                 125

Lys Gly Pro Lys Thr Arg Glu Asn Gln Gln Asp Val His Phe Met Lys
    130                 135                 140
```

```
Arg Tyr Pro Lys Gly Gln Pro Glu Leu Gln Lys Pro Phe Lys Tyr Thr
145                 150                 155                 160

Thr Val Thr Lys Arg Ser Arg Arg Ile Arg Pro Thr His Pro Ala
                165                 170                 175

<210> SEQ ID NO 12
<211> LENGTH: 528
<212> TYPE: DNA
<213> ORGANISM: Artificial Sequence
<220> FEATURE:
<223> OTHER INFORMATION: Synthetic polynucleotide

<400> SEQUENCE: 12
atgcgcatcc acgtggagaa ccagacgcgg gctcgggacg atgtgagccg taagcagctg      60
cggctgtacc agctctacag ccggaccagt gggaaacaca tccaggtcct gggccgcagg     120
atcagtgccc gcggcgagga tggggacaag tatgcccagc tcctagtgga gacagacacc     180
ttcggtagtc aagtccggat caagggcaag gagacggaat tctacctgtg catgaaccgc     240
aaaggcaagc tcgtggggaa gcccgatggc accagcaagg agtgtgtgtt catcgagaag     300
gttctggaga caaactacac ggccctgatg tcggctaagt actccggctg gtacgtgggc     360
ttcaccaaga aggggcggcc gcggaagggc cccaagaccc gggagaacca gcaggacgtg     420
catttcatga gcgctacccc aaggggcag ccggagcttc agaagccctt caagtacacg     480
acggtgacca gaggtcccg tcggatcagg cccacacacc ctgcctag                  528

<210> SEQ ID NO 13
<211> LENGTH: 174
<212> TYPE: PRT
<213> ORGANISM: Artificial Sequence
<220> FEATURE:
<223> OTHER INFORMATION: Synthetic polypeptide

<400> SEQUENCE: 13

Met Ile His Val Glu Asn Gln Thr Arg Ala Arg Asp Asp Val Ser Arg
1               5                   10                  15

Lys Gln Leu Arg Leu Tyr Gln Leu Tyr Ser Arg Thr Ser Gly Lys His
                20                  25                  30

Ile Gln Val Leu Gly Arg Arg Ile Ser Ala Arg Gly Glu Asp Gly Asp
                35                  40                  45

Lys Tyr Ala Gln Leu Leu Val Glu Thr Asp Thr Phe Gly Ser Gln Val
50                  55                  60

Arg Ile Lys Gly Lys Glu Thr Glu Phe Tyr Leu Cys Met Asn Arg Lys
65                  70                  75                  80

Gly Lys Leu Val Gly Lys Pro Asp Gly Thr Ser Lys Glu Cys Val Phe
                85                  90                  95

Ile Glu Lys Val Leu Glu Asn Asn Tyr Thr Ala Leu Met Ser Ala Lys
                100                 105                 110

Tyr Ser Gly Trp Tyr Val Gly Phe Thr Lys Lys Gly Arg Pro Arg Lys
                115                 120                 125

Gly Pro Lys Thr Arg Glu Asn Gln Gln Asp Val His Phe Met Lys Arg
130                 135                 140

Tyr Pro Lys Gly Gln Pro Glu Leu Gln Lys Pro Phe Lys Tyr Thr Thr
145                 150                 155                 160

Val Thr Lys Arg Ser Arg Arg Ile Arg Pro Thr His Pro Ala
                165                 170

<210> SEQ ID NO 14
```

<211> LENGTH: 525
<212> TYPE: DNA
<213> ORGANISM: Artificial Sequence
<220> FEATURE:
<223> OTHER INFORMATION: Synthetic polynucleotide

<400> SEQUENCE: 14

```
atgatccacg tggagaacca gacgcgggct cgggacgatg tgagccgtaa gcagctgcgg      60
ctgtaccagc tctacagccg gaccagtggg aaacacatcc aggtcctggg ccgcaggatc     120
agtgcccgcg gcgaggatgg ggacaagtat gcccagctcc tagtggagac agacaccttc     180
ggtagtcaag tccggatcaa gggcaaggag acggaattct acctgtgcat gaaccgcaaa     240
ggcaagctcg tggggaagcc cgatggcacc agcaaggagt gtgtgttcat cgagaaggtt     300
ctggagaaca actacacggc cctgatgtcg gctaagtact ccggctggta cgtgggcttc     360
accaagaagg ggcggccgcg gaagggcccc aagacccggg agaaccagca ggacgtgcat     420
ttcatgaagc gctaccccaa ggggcagccg gagcttcaga agcccttcaa gtacacgacg     480
gtgaccaaga ggtcccgtcg gatcaggccc acacaccctg cctag                      525
```

<210> SEQ ID NO 15
<211> LENGTH: 173
<212> TYPE: PRT
<213> ORGANISM: Artificial Sequence
<220> FEATURE:
<223> OTHER INFORMATION: Synthetic polypeptide

<400> SEQUENCE: 15

```
Met His Val Glu Asn Gln Thr Arg Ala Arg Asp Asp Val Ser Arg Lys
 1               5                  10                  15
Gln Leu Arg Leu Tyr Gln Leu Tyr Ser Arg Thr Ser Gly Lys His Ile
            20                  25                  30
Gln Val Leu Gly Arg Arg Ile Ser Ala Arg Gly Glu Asp Gly Asp Lys
        35                  40                  45
Tyr Ala Gln Leu Leu Val Glu Thr Asp Thr Phe Gly Ser Gln Val Arg
    50                  55                  60
Ile Lys Gly Lys Glu Thr Glu Phe Tyr Leu Cys Met Asn Arg Lys Gly
65                  70                  75                  80
Lys Leu Val Gly Lys Pro Asp Gly Thr Ser Lys Glu Cys Val Phe Ile
                85                  90                  95
Glu Lys Val Leu Glu Asn Asn Tyr Thr Ala Leu Met Ser Ala Lys Tyr
            100                 105                 110
Ser Gly Trp Tyr Val Gly Phe Thr Lys Lys Gly Arg Pro Arg Lys Gly
        115                 120                 125
Pro Lys Thr Arg Glu Asn Gln Gln Asp Val His Phe Met Lys Arg Tyr
    130                 135                 140
Pro Lys Gly Gln Pro Glu Leu Gln Lys Pro Phe Lys Tyr Thr Thr Val
145                 150                 155                 160
Thr Lys Arg Ser Arg Arg Ile Arg Pro Thr His Pro Ala
                165                 170
```

<210> SEQ ID NO 16
<211> LENGTH: 522
<212> TYPE: DNA
<213> ORGANISM: Artificial Sequence
<220> FEATURE:
<223> OTHER INFORMATION: Synthetic polynucleotide

<400> SEQUENCE: 16

```
atgcacgtgg agaaccagac gcgggctcgg gacgatgtga gccgtaagca gctgcggctg    60
taccagctct acagccggac cagtgggaaa cacatccagg tcctgggccg caggatcagt   120
gcccgcggcg aggatgggga caagtatgcc cagctcctag tggagacaga caccttcggt   180
agtcaagtcc ggatcaaggg caaggagacg gaattctacc tgtgcatgaa ccgcaaaggc   240
aagctcgtgg ggaagcccga tggcaccagc aaggagtgtg tgttcatcga aaggttctg    300 gagaacaact acacggccct gatgtcggct aagtactccg ctggtacgt gggcttcacc    360 aagaagggc ggccgcggaa gggccccaag accgggaga accagcagga cgtgcatttc     420
atgaagcgct accccaaggg gcagccggag cttcagaagc ccttcaagta cacgacggtg    480
accaagaggt cccgtcggat caggcccaca caccctgcct ag                      522
```

<210> SEQ ID NO 17
<211> LENGTH: 172
<212> TYPE: PRT
<213> ORGANISM: Artificial Sequence
<220> FEATURE:
<223> OTHER INFORMATION: Synthetic polypeptide

<400> SEQUENCE: 17

```
Met Val Glu Asn Gln Thr Arg Ala Arg Asp Asp Val Ser Arg Lys Gln
1               5                   10                  15

Leu Arg Leu Tyr Gln Leu Tyr Ser Arg Thr Ser Gly Lys His Ile Gln
            20                  25                  30

Val Leu Gly Arg Arg Ile Ser Ala Arg Gly Glu Asp Gly Asp Lys Tyr
        35                  40                  45

Ala Gln Leu Leu Val Glu Thr Asp Thr Phe Gly Ser Gln Val Arg Ile
    50                  55                  60

Lys Gly Lys Glu Thr Glu Phe Tyr Leu Cys Met Asn Arg Lys Gly Lys
65                  70                  75                  80

Leu Val Gly Lys Pro Asp Gly Thr Ser Lys Glu Cys Val Phe Ile Glu
                85                  90                  95

Lys Val Leu Glu Asn Asn Tyr Thr Ala Leu Met Ser Ala Lys Tyr Ser
            100                 105                 110

Gly Trp Tyr Val Gly Phe Thr Lys Lys Gly Arg Pro Arg Lys Gly Pro
        115                 120                 125

Lys Thr Arg Glu Asn Gln Gln Asp Val His Phe Met Lys Arg Tyr Pro
    130                 135                 140

Lys Gly Gln Pro Glu Leu Gln Lys Pro Phe Lys Tyr Thr Thr Val Thr
145                 150                 155                 160

Lys Arg Ser Arg Arg Ile Arg Pro Thr His Pro Ala
                165                 170
```

<210> SEQ ID NO 18
<211> LENGTH: 519
<212> TYPE: DNA
<213> ORGANISM: Artificial Sequence
<220> FEATURE:
<223> OTHER INFORMATION: Synthetic polynucleotide

<400> SEQUENCE: 18

```
atggtggaga accagacgcg ggctcgggac gatgtgagcc gtaagcagct gcggctgtac    60
cagctctaca gccggaccag tgggaaacac atccaggtcc tgggccgcag gatcagtgcc   120
cgcggcgagg atggggacaa gtatgcccag ctcctagtgg agacagacac cttcggtagt   180
caagtccgga tcaagggcaa ggagacggaa ttctacctgt gcatgaaccg caaaggcaag   240
```

```
ctcgtgggga agcccgatgg caccagcaag gagtgtgtgt tcatcgagaa ggttctggag    300
aacaactaca cggccctgat gtcggctaag tactccggct ggtacgtggg cttcaccaag    360
aaggggcggc cgcggaaggg ccccaagacc cgggagaacc agcaggacgt gcatttcatg    420
aagcgctacc ccaaggggca gccggagctt cagaagccct tcaagtacac gacggtgacc    480
aagaggtccc gtcggatcag gcccacacac cctgcctag                          519
```

```
<210> SEQ ID NO 19
<211> LENGTH: 171
<212> TYPE: PRT
<213> ORGANISM: Artificial Sequence
<220> FEATURE:
<223> OTHER INFORMATION: Synthetic polypeptide

<400> SEQUENCE: 19
```

Met Glu Asn Gln Thr Arg Ala Arg Asp Asp Val Ser Arg Lys Gln Leu
1               5                   10                  15

Arg Leu Tyr Gln Leu Tyr Ser Arg Thr Ser Gly Lys His Ile Gln Val
            20                  25                  30

Leu Gly Arg Arg Ile Ser Ala Arg Gly Glu Asp Gly Asp Lys Tyr Ala
        35                  40                  45

Gln Leu Leu Val Glu Thr Asp Thr Phe Gly Ser Gln Val Arg Ile Lys
    50                  55                  60

Gly Lys Glu Thr Glu Phe Tyr Leu Cys Met Asn Arg Lys Gly Lys Leu
65                  70                  75                  80

Val Gly Lys Pro Asp Gly Thr Ser Lys Glu Cys Val Phe Ile Glu Lys
                85                  90                  95

Val Leu Glu Asn Asn Tyr Thr Ala Leu Met Ser Ala Lys Tyr Ser Gly
            100                 105                 110

Trp Tyr Val Gly Phe Thr Lys Lys Gly Arg Pro Arg Lys Gly Pro Lys
        115                 120                 125

Thr Arg Glu Asn Gln Gln Asp Val His Phe Met Lys Arg Tyr Pro Lys
    130                 135                 140

Gly Gln Pro Glu Leu Gln Lys Pro Phe Lys Tyr Thr Thr Val Thr Lys
145                 150                 155                 160

Arg Ser Arg Arg Ile Arg Pro Thr His Pro Ala
                165                 170

```
<210> SEQ ID NO 20
<211> LENGTH: 516
<212> TYPE: DNA
<213> ORGANISM: Artificial Sequence
<220> FEATURE:
<223> OTHER INFORMATION: Synthetic polynucleotide

<400> SEQUENCE: 20
atggagaacc agacgcgggc tcgggacgat gtgagccgta agcagctgcg gctgtaccag     60
ctctacagcc ggaccagtgg gaaacacatc caggtcctgg ccgcaggat cagtgcccgc    120 ggcgaggatg gggacaagta tgcccagctc ctagtggaga cagacacctt cggtagtcaa    180
gtccggatca agggcaagga gacggaattc tacctgtgca tgaaccgcaa aggcaagctc    240
gtggggaagc ccgatggcac cagcaaggag tgtgtgttca tcgagaaggt tctggagaac    300
aactacacgg ccctgatgtc ggctaagtac tccggctggt acgtgggctt caccaagaag    360
gggcggccgc ggaagggccc caagacccgg gagaaccagc aggacgtgca tttcatgaag    420
cgctacccca aggggcagcc ggagcttcag aagcccttca gtacacgac ggtgaccaag    480
```
aggtcccgtc ggatcaggcc cacacaccct gcctag        516

<210> SEQ ID NO 21
<211> LENGTH: 170
<212> TYPE: PRT
<213> ORGANISM: Artificial Sequence
<220> FEATURE:
<223> OTHER INFORMATION: Synthetic polypeptide

<400> SEQUENCE: 21

```
Met Asn Gln Thr Arg Ala Arg Asp Asp Val Ser Arg Lys Gln Leu Arg
1               5                   10                  15

Leu Tyr Gln Leu Tyr Ser Arg Thr Ser Gly Lys His Ile Gln Val Leu
            20                  25                  30

Gly Arg Arg Ile Ser Ala Arg Gly Glu Asp Gly Asp Lys Tyr Ala Gln
        35                  40                  45

Leu Leu Val Glu Thr Asp Thr Phe Gly Ser Gln Val Arg Ile Lys Gly
    50                  55                  60

Lys Glu Thr Glu Phe Tyr Leu Cys Met Asn Arg Lys Gly Lys Leu Val
65                  70                  75                  80

Gly Lys Pro Asp Gly Thr Ser Lys Glu Cys Val Phe Ile Glu Lys Val
                85                  90                  95

Leu Glu Asn Asn Tyr Thr Ala Leu Met Ser Ala Lys Tyr Ser Gly Trp
            100                 105                 110

Tyr Val Gly Phe Thr Lys Lys Gly Arg Pro Arg Lys Gly Pro Lys Thr
        115                 120                 125

Arg Glu Asn Gln Gln Asp Val His Phe Met Lys Arg Tyr Pro Lys Gly
    130                 135                 140

Gln Pro Glu Leu Gln Lys Pro Phe Lys Tyr Thr Thr Val Thr Lys Arg
145                 150                 155                 160

Ser Arg Arg Ile Arg Pro Thr His Pro Ala
                165                 170
```

<210> SEQ ID NO 22
<211> LENGTH: 513
<212> TYPE: DNA
<213> ORGANISM: Artificial Sequence
<220> FEATURE:
<223> OTHER INFORMATION: Synthetic polynucleotide

<400> SEQUENCE: 22
atgaaccaga cgcgggctcg ggacgatgtg agccgtaagc agctgcggct gtaccagctc        60
tacagccgga ccagtgggaa acacatccag gtcctgggcc gcaggatcag tgcccgcggc       120
gaggatgggg acaagtatgc ccagctccta gtggagacag acaccttcgg tagtcaagtc       180
cggatcaagg gcaaggagac ggaattctac ctgtgcatga accgcaaagg caagctcgtg       240
gggaagcccg atggcaccag caaggagtgt gtgttcatcg agaaggttct ggagaacaac       300
tacacggccc tgatgtcggc taagtactcc ggctggtacg tgggcttcac caagaagggg       360
cggccgcgga agggccccaa gacccgggag aaccagcagg acgtgcattt catgaagcgc       420
taccccaagg ggcagccgga gcttcagaag cccttcaagt acacgacggt gaccaagagg       480
tcccgtcgga tcaggcccac acacctgcc tag                                      513

<210> SEQ ID NO 23
<211> LENGTH: 169
<212> TYPE: PRT
<213> ORGANISM: Artificial Sequence
<220> FEATURE:

<223> OTHER INFORMATION: Synthetic polypeptide

<400> SEQUENCE: 23

Met Gln Thr Arg Ala Arg Asp Asp Val Ser Arg Lys Gln Leu Arg Leu
1               5                   10                  15

Tyr Gln Leu Tyr Ser Arg Thr Ser Gly Lys His Ile Gln Val Leu Gly
            20                  25                  30

Arg Arg Ile Ser Ala Arg Gly Glu Asp Gly Asp Lys Tyr Ala Gln Leu
        35                  40                  45

Leu Val Glu Thr Asp Thr Phe Gly Ser Gln Val Arg Ile Lys Gly Lys
50                  55                  60

Glu Thr Glu Phe Tyr Leu Cys Met Asn Arg Lys Gly Lys Leu Val Gly
65                  70                  75                  80

Lys Pro Asp Gly Thr Ser Lys Glu Cys Val Phe Ile Glu Lys Val Leu
                85                  90                  95

Glu Asn Asn Tyr Thr Ala Leu Met Ser Ala Lys Tyr Ser Gly Trp Tyr
            100                 105                 110

Val Gly Phe Thr Lys Lys Gly Arg Pro Arg Lys Gly Pro Lys Thr Arg
        115                 120                 125

Glu Asn Gln Gln Asp Val His Phe Met Lys Arg Tyr Pro Lys Gly Gln
    130                 135                 140

Pro Glu Leu Gln Lys Pro Phe Lys Tyr Thr Thr Val Thr Lys Arg Ser
145                 150                 155                 160

Arg Arg Ile Arg Pro Thr His Pro Ala
                165

<210> SEQ ID NO 24
<211> LENGTH: 510
<212> TYPE: DNA
<213> ORGANISM: Artificial Sequence
<220> FEATURE:
<223> OTHER INFORMATION: Synthetic polynucleotide

<400> SEQUENCE: 24
atgcagacgc gggctcggga cgatgtgagc cgtaagcagc tgcggctgta ccagctctac      60
agccggacca gtgggaaaca catccaggtc ctgggccgca ggatcagtgc ccgcggcgag     120
gatgggacaa gtatgcccaa gctcctagtg gagacagaca ccttcggtag tcaagtccgg     180
atcaagggca aggagacgga attctacctg tgcatgaacc gcaaaggcaa gctcgtgggg     240
aagcccgatg gcaccagcaa ggagtgtgtg ttcatcgaga aggttctgga gaacaactac     300
acggccctga tgtcggctaa gtactccggc tggtacgtgg gcttcaccaa gaaggggcgg     360
ccgcggaagg gccccaagac ccgggagaac cagcaggacg tgcatttcat gaagcgctac     420
cccaaggggc agccggagct tcagaagccc ttcaagtaca cgacggtgac caagaggtcc     480
cgtcggatca ggcccacaca ccctgcctag                                      510

<210> SEQ ID NO 25
<211> LENGTH: 168
<212> TYPE: PRT
<213> ORGANISM: Artificial Sequence
<220> FEATURE:
<223> OTHER INFORMATION: Synthetic polypeptide

<400> SEQUENCE: 25

Met Thr Arg Ala Arg Asp Asp Val Ser Arg Lys Gln Leu Arg Leu Tyr
1               5                   10                  15

Gln Leu Tyr Ser Arg Thr Ser Gly Lys His Ile Gln Val Leu Gly Arg

```
                    20                  25                  30
Arg Ile Ser Ala Arg Gly Glu Asp Gly Asp Lys Tyr Ala Gln Leu Leu
            35                  40                  45

Val Glu Thr Asp Thr Phe Gly Ser Gln Val Arg Ile Lys Gly Lys Glu
    50                  55                  60

Thr Glu Phe Tyr Leu Cys Met Asn Arg Lys Gly Lys Leu Val Gly Lys
65                  70                  75                  80

Pro Asp Gly Thr Ser Lys Glu Cys Val Phe Ile Glu Lys Val Leu Glu
                85                  90                  95

Asn Asn Tyr Thr Ala Leu Met Ser Ala Lys Tyr Ser Gly Trp Tyr Val
            100                 105                 110

Gly Phe Thr Lys Lys Gly Arg Pro Arg Lys Gly Pro Lys Thr Arg Glu
        115                 120                 125

Asn Gln Gln Asp Val His Phe Met Lys Arg Tyr Pro Lys Gly Gln Pro
    130                 135                 140

Glu Leu Gln Lys Pro Phe Lys Tyr Thr Thr Val Thr Lys Arg Ser Arg
145                 150                 155                 160

Arg Ile Arg Pro Thr His Pro Ala
                165

<210> SEQ ID NO 26
<211> LENGTH: 507
<212> TYPE: DNA
<213> ORGANISM: Artificial Sequence
<220> FEATURE:
<223> OTHER INFORMATION: Synthetic polynucleotide

<400> SEQUENCE: 26
atgacgcggg ctcgggacga tgtgagccgt aagcagctgc ggctgtacca gctctacagc        60
cggaccagtg ggaaacacat ccaggtcctg ggccgcagga tcagtgcccg cggcgaggat       120
ggggacaagt atgcccagct cctagtggag acagacacct tcggtagtca agtccggatc       180
aagggcaagg agacggaatt ctacctgtgc atgaaccgca aaggcaagct cgtggggaag       240
cccgatggca ccagcaagga gtgtgtgttc atcgagaagg ttctggagaa caactacacg       300
gccctgatgt cggctaagta ctccggctgg tacgtgggct tcaccaagaa ggggcggccg       360
cggaagggcc ccaagacccg ggagaaccag caggacgtgc atttcatgaa gcgctacccc       420 aagggcagc ggagcttca gaagcccttc aagtacacga cggtgaccaa gaggtcccgt        480
cggatcaggc ccacacaccc tgcctag                                            507

<210> SEQ ID NO 27
<211> LENGTH: 167
<212> TYPE: PRT
<213> ORGANISM: Artificial Sequence
<220> FEATURE:
<223> OTHER INFORMATION: Synthetic polypeptide

<400> SEQUENCE: 27

Met Arg Ala Arg Asp Asp Val Ser Arg Lys Gln Leu Arg Leu Tyr Gln
1               5                   10                  15

Leu Tyr Ser Arg Thr Ser Gly Lys His Ile Gln Val Leu Gly Arg Arg
            20                  25                  30

Ile Ser Ala Arg Gly Glu Asp Gly Asp Lys Tyr Ala Gln Leu Leu Val
        35                  40                  45

Glu Thr Asp Thr Phe Gly Ser Gln Val Arg Ile Lys Gly Lys Glu Thr
    50                  55                  60
```

```
Glu Phe Tyr Leu Cys Met Asn Arg Lys Gly Lys Leu Val Gly Lys Pro
 65                  70                  75                  80

Asp Gly Thr Ser Lys Glu Cys Val Phe Ile Glu Lys Val Leu Glu Asn
                 85                  90                  95

Asn Tyr Thr Ala Leu Met Ser Ala Lys Tyr Ser Gly Trp Tyr Val Gly
            100                 105                 110

Phe Thr Lys Lys Gly Arg Pro Arg Lys Gly Pro Lys Thr Arg Glu Asn
        115                 120                 125

Gln Gln Asp Val His Phe Met Lys Arg Tyr Pro Lys Gly Gln Pro Glu
    130                 135                 140

Leu Gln Lys Pro Phe Lys Tyr Thr Thr Val Thr Lys Arg Ser Arg
145                 150                 155                 160

Ile Arg Pro Thr His Pro Ala
                165

<210> SEQ ID NO 28
<211> LENGTH: 504
<212> TYPE: DNA
<213> ORGANISM: Artificial Sequence
<220> FEATURE:
<223> OTHER INFORMATION: Synthetic polynucleotide

<400> SEQUENCE: 28
atgcgggctc gggacgatgt gagccgtaag cagctgcggc tgtaccagct ctacagccgg      60
accagtggga aacacatcca ggtcctgggc cgcaggatca gtgcccgcgg cgaggatggg     120
gacaagtatg cccagctcct agtggagaca gacaccttcg gtagtcaagt ccggatcaag     180
ggcaaggaga cggaattcta cctgtgcatg aaccgcaaag caagctcgt ggggaagccc      240 gatggcacca gcaaggagtg tgtgttcatc gagaaggttc tggagaacaa ctacacggcc     300
ctgatgtcgg ctaagtactc cggctggtac gtgggcttca ccaagaaggg gcggccgcgg     360
aagggcccca gacccggga gaaccagcag gacgtgcatt tcatgaagcg ctaccccaag      420
gggcagccgg agcttcagaa gcccttcaag tacacgacgg tgaccaagag gtcccgtcgg     480
atcaggccca cacccctgc ctag                                             504

<210> SEQ ID NO 29
<211> LENGTH: 166
<212> TYPE: PRT
<213> ORGANISM: Artificial Sequence
<220> FEATURE:
<223> OTHER INFORMATION: Synthetic polypeptide

<400> SEQUENCE: 29

Met Ala Arg Asp Asp Val Ser Arg Lys Gln Leu Arg Leu Tyr Gln Leu
  1               5                  10                  15

Tyr Ser Arg Thr Ser Gly Lys His Ile Gln Val Leu Gly Arg Arg Ile
             20                  25                  30

Ser Ala Arg Gly Glu Asp Gly Asp Lys Tyr Ala Gln Leu Leu Val Glu
         35                  40                  45

Thr Asp Thr Phe Gly Ser Gln Val Arg Ile Lys Gly Lys Glu Thr Glu
     50                  55                  60

Phe Tyr Leu Cys Met Asn Arg Lys Gly Lys Leu Val Gly Lys Pro Asp
 65                  70                  75                  80

Gly Thr Ser Lys Glu Cys Val Phe Ile Glu Lys Val Leu Glu Asn Asn
                 85                  90                  95

Tyr Thr Ala Leu Met Ser Ala Lys Tyr Ser Gly Trp Tyr Val Gly Phe
            100                 105                 110
```

Thr Lys Lys Gly Arg Pro Arg Lys Gly Pro Lys Thr Arg Glu Asn Gln
            115                 120                 125

Gln Asp Val His Phe Met Lys Arg Tyr Pro Lys Gly Gln Pro Glu Leu
        130                 135                 140

Gln Lys Pro Phe Lys Tyr Thr Thr Val Thr Lys Arg Ser Arg Arg Ile
145                 150                 155                 160

Arg Pro Thr His Pro Ala
                165

<210> SEQ ID NO 30
<211> LENGTH: 501
<212> TYPE: DNA
<213> ORGANISM: Artificial Sequence
<220> FEATURE:
<223> OTHER INFORMATION: Synthetic polynucleotide

<400> SEQUENCE: 30
atggctcggg acgatgtgag ccgtaagcag ctgcggctgt accagctcta cagccggacc      60
agtgggaaac acatccaggt cctgggccgc aggatcagtg cccgcggcga ggatggggac     120
aagtatgccc agctcctagt ggagacagac accttcggta gtcaagtccg gatcaagggc     180
aaggagacgg aattctacct gtgcatgaac cgcaaaggca agctcgtggg aagcccgat     240 ggcaccagca aggagtgtgt gttcatcgag aaggttctgg agaacaacta cacggccctg     300
atgtcggcta agtactccgg ctggtacgtg ggcttcacca agaaggggcg gccgcggaag     360
ggcccccaag a cccgggagaa ccagcaggac gtgcatttca tgaagcgcta ccccaagggg     420
cagccggagc ttcagaagcc cttcaagtac acgacggtga ccaagaggtc ccgtcggatc     480
aggcccacac accctgccta g                                                501

<210> SEQ ID NO 31
<211> LENGTH: 165
<212> TYPE: PRT
<213> ORGANISM: Artificial Sequence
<220> FEATURE:
<223> OTHER INFORMATION: Synthetic polypeptide

<400> SEQUENCE: 31

Met Arg Asp Asp Val Ser Arg Lys Gln Leu Arg Leu Tyr Gln Leu Tyr
1               5                   10                  15

Ser Arg Thr Ser Gly Lys His Ile Gln Val Leu Gly Arg Arg Ile Ser
            20                  25                  30

Ala Arg Gly Glu Asp Gly Asp Lys Tyr Ala Gln Leu Leu Val Glu Thr
        35                  40                  45

Asp Thr Phe Gly Ser Gln Val Arg Ile Lys Gly Lys Glu Thr Glu Phe
    50                  55                  60

Tyr Leu Cys Met Asn Arg Lys Gly Lys Leu Val Gly Lys Pro Asp Gly
65                  70                  75                  80

Thr Ser Lys Glu Cys Val Phe Ile Glu Lys Val Leu Glu Asn Asn Tyr
            85                  90                  95

Thr Ala Leu Met Ser Ala Lys Tyr Ser Gly Trp Tyr Val Gly Phe Thr
        100                 105                 110

Lys Lys Gly Arg Pro Arg Lys Gly Pro Lys Thr Arg Glu Asn Gln Gln
    115                 120                 125

Asp Val His Phe Met Lys Arg Tyr Pro Lys Gly Gln Pro Glu Leu Gln
130                 135                 140

Lys Pro Phe Lys Tyr Thr Thr Val Thr Lys Arg Ser Arg Arg Ile Arg

```
                145                 150                 155                 160
Pro Thr His Pro Ala
                165

<210> SEQ ID NO 32
<211> LENGTH: 498
<212> TYPE: DNA
<213> ORGANISM: Artificial Sequence
<220> FEATURE:
<223> OTHER INFORMATION: Synthetic polynucleotide

<400> SEQUENCE: 32
atgcgggacg atgtgagccg taagcagctg cggctgtacc agctctacag ccggaccagt    60
gggaaacaca tccaggtcct gggccgcagg atcagtgccc gcggcgagga tgggacaag    120 tatgcccagc tcctagtgga gacagacacc ttcggtagtc aagtccggat caagggcaag   180
gagacggaat tctacctgtg catgaaccgc aaaggcaagc tcgtgtgggaa gcccgatggc   240 accagcaagg agtgtgtgtt catcgagaag gttctggaga caactacac ggccctgatg    300 tcggctaagt actccggctg gtacgtgggc ttcaccaaga aggggcggcc gcggaagggc    360
cccaagaccc gggagaacca gcaggacgtg catttcatga gcgctaccc caaggggcag    420 ccggagcttc agaagcccct taagtacacg acggtgacca agaggtcccg tcggatcagg    480
cccacacacc ctgcctag                                                  498

<210> SEQ ID NO 33
<211> LENGTH: 164
<212> TYPE: PRT
<213> ORGANISM: Artificial Sequence
<220> FEATURE:
<223> OTHER INFORMATION: Synthetic polypeptide

<400> SEQUENCE: 33

Met Asp Asp Val Ser Arg Lys Gln Leu Arg Leu Tyr Gln Leu Tyr Ser
1               5                   10                  15

Arg Thr Ser Gly Lys His Ile Gln Val Leu Gly Arg Arg Ile Ser Ala
                20                  25                  30

Arg Gly Glu Asp Gly Asp Lys Tyr Ala Gln Leu Leu Val Glu Thr Asp
            35                  40                  45

Thr Phe Gly Ser Gln Val Arg Ile Lys Gly Lys Glu Thr Glu Phe Tyr
        50                  55                  60

Leu Cys Met Asn Arg Lys Gly Lys Leu Val Gly Lys Pro Asp Gly Thr
65                  70                  75                  80

Ser Lys Glu Cys Val Phe Ile Glu Lys Val Leu Glu Asn Asn Tyr Thr
                85                  90                  95

Ala Leu Met Ser Ala Lys Tyr Ser Gly Trp Tyr Val Gly Phe Thr Lys
            100                 105                 110

Lys Gly Arg Pro Arg Lys Gly Pro Lys Thr Arg Glu Asn Gln Gln Asp
        115                 120                 125

Val His Phe Met Lys Arg Tyr Pro Lys Gly Gln Pro Glu Leu Gln Lys
    130                 135                 140

Pro Phe Lys Tyr Thr Thr Val Thr Lys Arg Ser Arg Arg Ile Arg Pro
145                 150                 155                 160

Thr His Pro Ala

<210> SEQ ID NO 34
<211> LENGTH: 495
<212> TYPE: DNA
```

<213> ORGANISM: Artificial Sequence
<220> FEATURE:
<223> OTHER INFORMATION: Synthetic polynucleotide

<400> SEQUENCE: 34

```
atggacgatg tgagccgtaa gcagctgcgg ctgtaccagc tctacagccg gaccagtggg      60
aaacacatcc aggtcctggg ccgcaggatc agtgcccgcg gcgaggatgg ggacaagtat     120
gcccagctcc tagtggagac agacaccttc ggtagtcaag tccggatcaa gggcaaggag     180
acggaattct acctgtgcat gaaccgcaaa ggcaagctcg tggggaagcc cgatggcacc     240
agcaaggagt gtgtgttcat cgagaaggtt ctggagaaca actacacggc cctgatgtcg     300
gctaagtact ccggctggta cgtgggcttc accaagaagg ggcggccgcg aagggccccc     360
aagacccggg agaaccagca ggacgtgcat ttcatgaagc gctaccccaa ggggcagccg     420
gagcttcaga agcccttcaa gtacgacgcg gtgaccaaga ggtcccgtcg gatcaggccc     480
acacaccctg cctag                                                     495
```

<210> SEQ ID NO 35
<211> LENGTH: 163
<212> TYPE: PRT
<213> ORGANISM: Artificial Sequence
<220> FEATURE:
<223> OTHER INFORMATION: Synthetic polypeptide

<400> SEQUENCE: 35

```
Met Asp Val Ser Arg Lys Gln Leu Arg Leu Tyr Gln Leu Tyr Ser Arg
1               5                   10                  15
Thr Ser Gly Lys His Ile Gln Val Leu Gly Arg Arg Ile Ser Ala Arg
            20                  25                  30
Gly Glu Asp Gly Asp Lys Tyr Ala Gln Leu Leu Val Glu Thr Asp Thr
        35                  40                  45
Phe Gly Ser Gln Val Arg Ile Lys Gly Lys Glu Thr Glu Phe Tyr Leu
    50                  55                  60
Cys Met Asn Arg Lys Gly Lys Leu Val Gly Lys Pro Asp Gly Thr Ser
65                  70                  75                  80
Lys Glu Cys Val Phe Ile Glu Lys Val Leu Glu Asn Asn Tyr Thr Ala
                85                  90                  95
Leu Met Ser Ala Lys Tyr Ser Gly Trp Tyr Val Gly Phe Thr Lys Lys
            100                 105                 110
Gly Arg Pro Arg Lys Gly Pro Lys Thr Arg Glu Asn Gln Gln Asp Val
        115                 120                 125
His Phe Met Lys Arg Tyr Pro Lys Gly Gln Pro Glu Leu Gln Lys Pro
    130                 135                 140
Phe Lys Tyr Thr Thr Val Thr Lys Arg Ser Arg Arg Ile Arg Pro Thr
145                 150                 155                 160
His Pro Ala
```

<210> SEQ ID NO 36
<211> LENGTH: 492
<212> TYPE: DNA
<213> ORGANISM: Artificial Sequence
<220> FEATURE:
<223> OTHER INFORMATION: Synthetic polynucleotide

<400> SEQUENCE: 36

```
atggatgtga gccgtaagca gctgcggctg taccagctct acagccggac cagtgggaaa      60
cacatccagg tcctgggccg caggatcagt gcccgcggcg aggatgggga caagtatgcc     120
```

```
cagctcctag tggagacaga caccttcggt agtcaagtcc ggatcaaggg caaggagacg 180
gaattctacc tgtgcatgaa ccgcaaaggc aagctcgtgg ggaagcccga tggcaccagc 240
aaggagtgtg tgttcatcga gaaggttctg gagaacaact acacggccct gatgtcggct 300
```

```
aagtactccg gctggtacgt gggcttcacc aagaaggggc ggccgcggaa gggccccaag 360
acccgggaga accagcagga cgtgcatttc atgaagcgct accccaaggg gcagccggag 420
cttcagaagc ccttcaagta cacgacggtg accaagaggt cccgtcggat caggcccaca 480
caccctgcct ag 492
```

<210> SEQ ID NO 37
<211> LENGTH: 162
<212> TYPE: PRT
<213> ORGANISM: Artificial Sequence
<220> FEATURE:
<223> OTHER INFORMATION: Synthetic polypeptide

<400> SEQUENCE: 37

```
Met Val Ser Arg Lys Gln Leu Arg Leu Tyr Gln Leu Tyr Ser Arg Thr
1 5 10 15

Ser Gly Lys His Ile Gln Val Leu Gly Arg Arg Ile Ser Ala Arg Gly
20 25 30

Glu Asp Gly Asp Lys Tyr Ala Gln Leu Leu Val Glu Thr Asp Thr Phe
35 40 45

Gly Ser Gln Val Arg Ile Lys Gly Lys Glu Thr Glu Phe Tyr Leu Cys
50 55 60

Met Asn Arg Lys Gly Lys Leu Val Gly Lys Pro Asp Gly Thr Ser Lys
65 70 75 80

Glu Cys Val Phe Ile Glu Lys Val Leu Glu Asn Asn Tyr Thr Ala Leu
85 90 95

Met Ser Ala Lys Tyr Ser Gly Trp Tyr Val Gly Phe Thr Lys Lys Gly
100 105 110

Arg Pro Arg Lys Gly Pro Lys Thr Arg Glu Asn Gln Gln Asp Val His
115 120 125

Phe Met Lys Arg Tyr Pro Lys Gly Gln Pro Glu Leu Gln Lys Pro Phe
130 135 140

Lys Tyr Thr Thr Val Thr Lys Arg Ser Arg Arg Ile Arg Pro Thr His
145 150 155 160

Pro Ala
```

<210> SEQ ID NO 38
<211> LENGTH: 489
<212> TYPE: DNA
<213> ORGANISM: Artificial Sequence
<220> FEATURE:
<223> OTHER INFORMATION: Synthetic polynucleotide

<400> SEQUENCE: 38

```
atggtgagcc gtaagcagct gcggctgtac cagctctaca gccggaccag tgggaaacac 60
atccaggtcc tgggccgcag gatcagtgcc cgcggcgagg atggggacaa gtatgcccag 120
ctcctagtgg agacagacac cttcggtagt caagtccgga tcaagggcaa ggagacggaa 180
ttctacctgt gcatgaaccg caaaggcaag ctcgtgggga agcccgatgg caccagcaag 240
gagtgtgtgt tcatcgagaa ggttctggag aacaactaca cggccctgat gtcggctaag 300
tactccggct ggtacgtggg cttcaccaag aaggggcggc cgcggaaggg ccccaagacc 360
```

```
cgggagaacc agcaggacgt gcatttcatg aagcgctacc ccaagggggca gccggagctt    420 cagaagccct tcaagtacac gacggtgacc aagaggtccc gtcggatcag gcccacacac    480
cctgcctag                                                            489
```

```
<210> SEQ ID NO 39
<211> LENGTH: 161
<212> TYPE: PRT
<213> ORGANISM: Artificial Sequence
<220> FEATURE:
<223> OTHER INFORMATION: Synthetic polypeptide

<400> SEQUENCE: 39
```

Met Ser Arg Lys Gln Leu Arg Leu Tyr Gln Leu Tyr Ser Arg Thr Ser
1               5                   10                  15

Gly Lys His Ile Gln Val Leu Gly Arg Arg Ile Ser Ala Arg Gly Glu
            20                  25                  30

Asp Gly Asp Lys Tyr Ala Gln Leu Leu Val Glu Thr Asp Thr Phe Gly
        35                  40                  45

Ser Gln Val Arg Ile Lys Gly Lys Glu Thr Glu Phe Tyr Leu Cys Met
    50                  55                  60

Asn Arg Lys Gly Lys Leu Val Gly Lys Pro Asp Gly Thr Ser Lys Glu
65                  70                  75                  80

Cys Val Phe Ile Glu Lys Val Leu Glu Asn Asn Tyr Thr Ala Leu Met
                85                  90                  95

Ser Ala Lys Tyr Ser Gly Trp Tyr Val Gly Phe Thr Lys Lys Gly Arg
            100                 105                 110

Pro Arg Lys Gly Pro Lys Thr Arg Glu Asn Gln Gln Asp Val His Phe
        115                 120                 125

Met Lys Arg Tyr Pro Lys Gly Gln Pro Glu Leu Gln Lys Pro Phe Lys
    130                 135                 140

Tyr Thr Thr Val Thr Lys Arg Ser Arg Arg Ile Arg Pro Thr His Pro
145                 150                 155                 160

Ala

```
<210> SEQ ID NO 40
<211> LENGTH: 486
<212> TYPE: DNA
<213> ORGANISM: Artificial Sequence
<220> FEATURE:
<223> OTHER INFORMATION: Synthetic polynucleotide

<400> SEQUENCE: 40
atgagccgta agcagctgcg gctgtaccag ctctacagcc ggaccagtgg gaaacacatc     60
caggtcctgg gccgcaggat cagtgcccgc ggcgaggatg gggacaagta tgcccagctc    120
ctagtggaga cagacacctt cggtagtcaa gtccggatca agggcaagga gacggaattc    180
tacctgtgca tgaaccgcaa aggcaagctc gtggggaagc ccgatggcac cagcaaggag    240
tgtgtgttca tcgagaaggt tctggagaac aactacacgg ccctgatgtc ggctaagtac    300
tccggctggt acgtgggctt caccaagaag gggcggccgc ggaagggccc caagacccgg    360
gagaaccagc aggacgtgca tttcatgaag cgctacccca gggcagcc ggagcttcag    420 aagcccttca gtacacgac ggtgaccaag aggtcccgtc ggatcaggcc cacacaccct    480
gcctag                                                              486
```

```
<210> SEQ ID NO 41
<211> LENGTH: 160
```

<212> TYPE: PRT
<213> ORGANISM: Artificial Sequence
<220> FEATURE:
<223> OTHER INFORMATION: Synthetic polypeptide

<400> SEQUENCE: 41

Met Arg Lys Gln Leu Arg Leu Tyr Gln Leu Tyr Ser Arg Thr Ser Gly
1               5                   10                  15

Lys His Ile Gln Val Leu Gly Arg Arg Ile Ser Ala Arg Gly Glu Asp
            20                  25                  30

Gly Asp Lys Tyr Ala Gln Leu Leu Val Glu Thr Asp Thr Phe Gly Ser
        35                  40                  45

Gln Val Arg Ile Lys Gly Lys Glu Thr Glu Phe Tyr Leu Cys Met Asn
    50                  55                  60

Arg Lys Gly Lys Leu Val Gly Lys Pro Asp Gly Thr Ser Lys Glu Cys
65                  70                  75                  80

Val Phe Ile Glu Lys Val Leu Glu Asn Asn Tyr Thr Ala Leu Met Ser
                85                  90                  95

Ala Lys Tyr Ser Gly Trp Tyr Val Gly Phe Thr Lys Lys Gly Arg Pro
            100                 105                 110

Arg Lys Gly Pro Lys Thr Arg Glu Asn Gln Gln Asp Val His Phe Met
        115                 120                 125

Lys Arg Tyr Pro Lys Gly Gln Pro Glu Leu Gln Lys Pro Phe Lys Tyr
    130                 135                 140

Thr Thr Val Thr Lys Arg Ser Arg Arg Ile Arg Pro Thr His Pro Ala
145                 150                 155                 160

<210> SEQ ID NO 42
<211> LENGTH: 486
<212> TYPE: DNA
<213> ORGANISM: Artificial Sequence
<220> FEATURE:
<223> OTHER INFORMATION: Synthetic polynucleotide

<400> SEQUENCE: 42
atgagccgta agcagctgcg gctgtaccag ctctacagcc ggaccagtgg gaaacacatc      60
caggtcctgg gccgcaggat cagtgcccgc ggcgaggatg gggacaagta tgcccagctc     120
ctagtggaga cagacacctt cggtagtcaa gtccggatca agggcaagga cggaattc      180 tacctgtgca tgaaccgcaa aggcaagctc gtggggaagc ccgatggcac cagcaaggag     240
tgtgtgttca tcgagaaggt tctggagaac aactacacgg ccctgatgtc ggctaagtac     300
tccggctggt acgtgggctt caccaagaag gggcggccgc ggaagggccc caagacccgg     360
gagaaccagc aggacgtgca tttcatgaag cgctacccca aggggcagcc ggagcttcag     420
aagcccttca gtacacgac ggtgaccaag aggtcccgtc ggatcaggcc cacacaccct     480
gcctag                                                                486

<210> SEQ ID NO 43
<211> LENGTH: 159
<212> TYPE: PRT
<213> ORGANISM: Artificial Sequence
<220> FEATURE:
<223> OTHER INFORMATION: Synthetic polypeptide

<400> SEQUENCE: 43

Met Lys Gln Leu Arg Leu Tyr Gln Leu Tyr Ser Arg Thr Ser Gly Lys
1               5                   10                  15

His Ile Gln Val Leu Gly Arg Arg Ile Ser Ala Arg Gly Glu Asp Gly

```
            20                  25                  30
Asp Lys Tyr Ala Gln Leu Leu Val Glu Thr Asp Thr Phe Gly Ser Gln
                35                  40                  45

Val Arg Ile Lys Gly Lys Glu Thr Glu Phe Tyr Leu Cys Met Asn Arg
 50                  55                  60

Lys Gly Lys Leu Val Gly Lys Pro Asp Gly Thr Ser Lys Glu Cys Val
 65                  70                  75                  80

Phe Ile Glu Lys Val Leu Glu Asn Asn Tyr Thr Ala Leu Met Ser Ala
                85                  90                  95

Lys Tyr Ser Gly Trp Tyr Val Gly Phe Thr Lys Lys Gly Arg Pro Arg
                100                 105                 110

Lys Gly Pro Lys Thr Arg Glu Asn Gln Gln Asp Val His Phe Met Lys
                115                 120                 125

Arg Tyr Pro Lys Gly Gln Pro Glu Leu Gln Lys Pro Lys Tyr Thr
            130                 135                 140

Thr Val Thr Lys Arg Ser Arg Arg Ile Arg Pro Thr His Pro Ala
145                 150                 155
```

```
<210> SEQ ID NO 44
<211> LENGTH: 483
<212> TYPE: DNA
<213> ORGANISM: Artificial Sequence
<220> FEATURE:
<223> OTHER INFORMATION: Synthetic polynucleotide

<400> SEQUENCE: 44
atgcgtaagc agctgcggct gtaccagctc tacagccgga ccagtgggaa acacatccag      60
gtcctgggcc gcaggatcag tgcccgcggc gaggatgggg acaagtatgc ccagctccta     120
gtggagacag acaccttcgg tagtcaagtc cggatcaagg gcaaggagac ggaattctac     180
ctgtgcatga accgcaaagg caagctcgtg gggaagcccg atggcaccag caaggagtgt     240
gtgttcatcg agaaggttct ggagaacaac tacacggccc tgatgtcggc taagtactcc     300
ggctggtacg tgggcttcac caagaagggg cggccgcgga agggccccaa gacccgggag     360
aaccagcagg acgtgcattt catgaagcgc taccccaagg gcagccgga  gcttcagaag     420 cccttcaagt acacgacggt gaccaagagg tcccgtcgga tcaggcccac acaccctgcc     480
tag                                                                    483
```

```
<210> SEQ ID NO 45
<211> LENGTH: 158
<212> TYPE: PRT
<213> ORGANISM: Artificial Sequence
<220> FEATURE:
<223> OTHER INFORMATION: Synthetic polypeptide

<400> SEQUENCE: 45

Met Gln Leu Arg Leu Tyr Gln Leu Tyr Ser Arg Thr Ser Gly Lys His
 1               5                  10                  15

Ile Gln Val Leu Gly Arg Arg Ile Ser Ala Arg Gly Glu Asp Gly Asp
                20                  25                  30

Lys Tyr Ala Gln Leu Leu Val Glu Thr Asp Thr Phe Gly Ser Gln Val
            35                  40                  45

Arg Ile Lys Gly Lys Glu Thr Glu Phe Tyr Leu Cys Met Asn Arg Lys
 50                  55                  60

Gly Lys Leu Val Gly Lys Pro Asp Gly Thr Ser Lys Glu Cys Val Phe
 65                  70                  75                  80
```

```
Ile Glu Lys Val Leu Glu Asn Asn Tyr Thr Ala Leu Met Ser Ala Lys
                85                  90                  95

Tyr Ser Gly Trp Tyr Val Gly Phe Thr Lys Lys Gly Arg Pro Arg Lys
            100                 105                 110

Gly Pro Lys Thr Arg Glu Asn Gln Gln Asp Val His Phe Met Lys Arg
        115                 120                 125

Tyr Pro Lys Gly Gln Pro Glu Leu Gln Lys Pro Phe Lys Tyr Thr Thr
    130                 135                 140

Val Thr Lys Arg Ser Arg Arg Ile Arg Pro Thr His Pro Ala
145                 150                 155
```

<210> SEQ ID NO 46
<211> LENGTH: 480
<212> TYPE: DNA
<213> ORGANISM: Artificial Sequence
<220> FEATURE:
<223> OTHER INFORMATION: Synthetic polynucleotide

<400> SEQUENCE: 46

```
atgaagcagc tgcggctgta ccagctctac agccggacca gtgggaaaca catccaggtc    60
ctgggccgca ggatcagtgc cgcggcgag  gatggggaca gtatgcccca gctcctagtg   120
gagacagaca ccttcggtag tcaagtccgg atcaagggca aggagacgga attctacctg   180
tgcatgaacc gcaaaggcaa gctcgtgggg aagcccgatg gcaccagcaa ggagtgtgtg   240
ttcatcgaga aggttctgga gaacaactac acggccctga tgtcggctaa gtactccggc   300
tggtacgtgg gcttcaccaa gaaggggcgg ccgcggaagg gccccaagac ccgggagaac   360
cagcaggacg tgcatttcat gaagcgctac cccaaggggc agccggagct tcagaagccc   420
ttcaagtaca cgacggtgac caagaggtcc cgtcggatca ggcccacaca ccctgcctag   480
```

<210> SEQ ID NO 47
<211> LENGTH: 157
<212> TYPE: PRT
<213> ORGANISM: Artificial Sequence
<220> FEATURE:
<223> OTHER INFORMATION: Synthetic polypeptide

<400> SEQUENCE: 47

```
Met Leu Arg Leu Tyr Gln Leu Tyr Ser Arg Thr Ser Gly Lys His Ile
1               5                   10                  15

Gln Val Leu Gly Arg Arg Ile Ser Ala Arg Gly Glu Asp Gly Asp Lys
            20                  25                  30

Tyr Ala Gln Leu Leu Val Glu Thr Asp Thr Phe Gly Ser Gln Val Arg
        35                  40                  45

Ile Lys Gly Lys Glu Thr Glu Phe Tyr Leu Cys Met Asn Arg Lys Gly
    50                  55                  60

Lys Leu Val Gly Lys Pro Asp Gly Thr Ser Lys Glu Cys Val Phe Ile
65                  70                  75                  80

Glu Lys Val Leu Glu Asn Asn Tyr Thr Ala Leu Met Ser Ala Lys Tyr
                85                  90                  95

Ser Gly Trp Tyr Val Gly Phe Thr Lys Lys Gly Arg Pro Arg Lys Gly
            100                 105                 110

Pro Lys Thr Arg Glu Asn Gln Gln Asp Val His Phe Met Lys Arg Tyr
        115                 120                 125

Pro Lys Gly Gln Pro Glu Leu Gln Lys Pro Phe Lys Tyr Thr Thr Val
    130                 135                 140

Thr Lys Arg Ser Arg Arg Ile Arg Pro Thr His Pro Ala
145                 150                 155
```

<210> SEQ ID NO 48
<211> LENGTH: 474
<212> TYPE: DNA
<213> ORGANISM: Artificial Sequence
<220> FEATURE:
<223> OTHER INFORMATION: Synthetic polynucleotide

<400> SEQUENCE: 48

```
atgctgcggc tgtaccagct ctacagccgg accagtggga acacatcca ggtcctgggc     60
cgcaggatca gtgcccgcgg cgaggatggg acaagtatg cccagctcct agtggagaca    120
gacaccttcg gtagtcaagt ccggatcaag ggcaaggaga cggaattcta cctgtgcatg    180
aaccgcaaag gcaagctcgt ggggaagccc gatggcacca gcaaggagtg tgtgttcatc    240
gagaaggttc tggagaacaa ctacacggcc ctgatgtcgg ctaagtactc cggctggtac    300
gtgggcttca ccaagaaggg gcggccgcgg aagggcccca agacccggga gaaccagcag    360
gacgtgcatt tcatgaagcg ctaccccaag gggcagccga gcttcagaa gcccttcaag    420
tacacgacgg tgaccaagag gtcccgtcgg atcaggccca cacaccctgc ctag          474
```

<210> SEQ ID NO 49
<211> LENGTH: 156
<212> TYPE: PRT
<213> ORGANISM: Artificial Sequence
<220> FEATURE:
<223> OTHER INFORMATION: Synthetic polypeptide

<400> SEQUENCE: 49

```
Met Arg Leu Tyr Gln Leu Tyr Ser Arg Thr Ser Gly Lys His Ile Gln
1               5                   10                  15
Val Leu Gly Arg Arg Ile Ser Ala Arg Gly Glu Asp Gly Asp Lys Tyr
            20                  25                  30
Ala Gln Leu Leu Val Glu Thr Asp Thr Phe Gly Ser Gln Val Arg Ile
        35                  40                  45
Lys Gly Lys Glu Thr Glu Phe Tyr Leu Cys Met Asn Arg Lys Gly Lys
    50                  55                  60
Leu Val Gly Lys Pro Asp Gly Thr Ser Lys Glu Cys Val Phe Ile Glu
65                  70                  75                  80
Lys Val Leu Glu Asn Asn Tyr Thr Ala Leu Met Ser Ala Lys Tyr Ser
                85                  90                  95
Gly Trp Tyr Val Gly Phe Thr Lys Lys Gly Arg Pro Arg Lys Gly Pro
            100                 105                 110
Lys Thr Arg Glu Asn Gln Gln Asp Val His Phe Met Lys Arg Tyr Pro
        115                 120                 125
Lys Gly Gln Pro Glu Leu Gln Lys Pro Phe Lys Tyr Thr Thr Val Thr
    130                 135                 140
Lys Arg Ser Arg Arg Ile Arg Pro Thr His Pro Ala
145                 150                 155
```

<210> SEQ ID NO 50
<211> LENGTH: 471
<212> TYPE: DNA
<213> ORGANISM: Artificial Sequence
<220> FEATURE:
<223> OTHER INFORMATION: Synthetic polynucleotide

<400> SEQUENCE: 50

```
atgcggctgt accagctcta cagccggacc agtgggaaac acatccaggt cctgggccgc     60
```

-continued

```
aggatcagtg cccgcggcga ggatggggac aagtatgccc agctcctagt ggagacagac      120
accttcggta gtcaagtccg gatcaagggc aaggagacgg aattctacct gtgcatgaac      180
cgcaaaggca agctcgtggg gaagcccgat ggcaccagca aggagtgtgt gttcatcgag      240
aaggttctgg agaacaacta cacggccctg atgtcggcta agtactccgg ctggtacgtg      300
ggcttcacca agaaggggcg gccgcggaag ggccccaaga cccgggagaa ccagcaggac      360
gtgcatttca tgaagcgcta ccccaagggg cagccggagc ttcagaagcc cttcaagtac      420
acgacggtga ccaagaggtc ccgtcggatc aggcccacac accctgccta g                471
```

<210> SEQ ID NO 51
<211> LENGTH: 155
<212> TYPE: PRT
<213> ORGANISM: Artificial Sequence
<220> FEATURE:
<223> OTHER INFORMATION: Synthetic polypeptide

<400> SEQUENCE: 51

```
Met Leu Tyr Gln Leu Tyr Ser Arg Thr Ser Gly Lys His Ile Gln Val
1               5                   10                  15

Leu Gly Arg Arg Ile Ser Ala Arg Gly Glu Asp Gly Asp Lys Tyr Ala
            20                  25                  30

Gln Leu Leu Val Glu Thr Asp Thr Phe Gly Ser Gln Val Arg Ile Lys
        35                  40                  45

Gly Lys Glu Thr Glu Phe Tyr Leu Cys Met Asn Arg Lys Gly Lys Leu
    50                  55                  60

Val Gly Lys Pro Asp Gly Thr Ser Lys Glu Cys Val Phe Ile Glu Lys
65                  70                  75                  80

Val Leu Glu Asn Asn Tyr Thr Ala Leu Met Ser Ala Lys Tyr Ser Gly
                85                  90                  95

Trp Tyr Val Gly Phe Thr Lys Lys Gly Arg Pro Arg Lys Gly Pro Lys
            100                 105                 110

Thr Arg Glu Asn Gln Gln Asp Val His Phe Met Lys Arg Tyr Pro Lys
        115                 120                 125

Gly Gln Pro Glu Leu Gln Lys Pro Phe Lys Tyr Thr Thr Val Thr Lys
    130                 135                 140

Arg Ser Arg Arg Ile Arg Pro Thr His Pro Ala
145                 150                 155
```

<210> SEQ ID NO 52
<211> LENGTH: 468
<212> TYPE: DNA
<213> ORGANISM: Artificial Sequence
<220> FEATURE:
<223> OTHER INFORMATION: Synthetic polynucleotide

<400> SEQUENCE: 52

```
atgctgtacc agctctacag ccggaccagt gggaaacaca tccaggtcct gggccgcagg       60
atcagtgccc gcggcgagga tggggacaag tatgcccagc tcctagtgga cagacacc       120 ttcggtagtc aagtccggat caagggcaag gagacggaat ctacctgtg catgaaccgc       180 aaaggcaagc tcgtgggaa gcccgatggc accagcaagg agtgtgtgtt catcgagaag       240
gttctggaga caactacac ggccctgatg tcggctaagt actccggctg gtacgtgggc       300
ttcaccaaga aggggcggcc gcggaagggc cccaagaccc gggagaacca gcaggacgtg       360
catttcatga agcgctaccc caaggggcag ccggagcttc agaagccctt caagtacacg       420
``` acgtgacca agaggtcccg tcggatcagg cccacacacc ctgcctag            468

<210> SEQ ID NO 53
<211> LENGTH: 154
<212> TYPE: PRT
<213> ORGANISM: Artificial Sequence
<220> FEATURE:
<223> OTHER INFORMATION: Synthetic polypeptide

<400> SEQUENCE: 53

Met Tyr Gln Leu Tyr Ser Arg Thr Ser Gly Lys His Ile Gln Val Leu
1               5                   10                  15

Gly Arg Arg Ile Ser Ala Arg Gly Glu Asp Gly Asp Lys Tyr Ala Gln
            20                  25                  30

Leu Leu Val Glu Thr Asp Thr Phe Gly Ser Gln Val Arg Ile Lys Gly
        35                  40                  45

Lys Glu Thr Glu Phe Tyr Leu Cys Met Asn Arg Lys Gly Lys Leu Val
    50                  55                  60

Gly Lys Pro Asp Gly Thr Ser Lys Glu Cys Val Phe Ile Glu Lys Val
65                  70                  75                  80

Leu Glu Asn Asn Tyr Thr Ala Leu Met Ser Ala Lys Tyr Ser Gly Trp
                85                  90                  95

Tyr Val Gly Phe Thr Lys Lys Gly Arg Pro Arg Lys Gly Pro Lys Thr
            100                 105                 110

Arg Glu Asn Gln Gln Asp Val His Phe Met Lys Arg Tyr Pro Lys Gly
        115                 120                 125

Gln Pro Glu Leu Gln Lys Pro Phe Lys Tyr Thr Thr Val Thr Lys Arg
    130                 135                 140

Ser Arg Arg Ile Arg Pro Thr His Pro Ala
145                 150

<210> SEQ ID NO 54
<211> LENGTH: 465
<212> TYPE: DNA
<213> ORGANISM: Artificial Sequence
<220> FEATURE:
<223> OTHER INFORMATION: Synthetic polynucleotide

<400> SEQUENCE: 54
atgtaccagc tctacagccg gaccagtggg aaacacatcc aggtcctggg ccgcaggatc      60
agtgcccgcg gcgaggatgg ggacaagtat gcccagctcc tagtggagac agacaccttc    120
ggtagtcaag tccggatcaa gggcaaggag acggaattct acctgtgcat gaaccgcaaa    180
ggcaagctcg tggggaagcc cgatggcacc agcaaggagt gtgtgttcat cgagaaggtt    240
ctggagaaca actacacggc cctgatgtcg gctaagtact ccggctggta cgtgggcttc    300
accaagaagg gcggccgcg aagggcccc aagacccggg agaaccagca ggacgtgcat      360
ttcatgaagc gctaccccaa ggggcagccg agcttcaga agcccttcaa gtacacgacg    420
gtgaccaaga ggtcccgtcg gatcaggccc acacacctg cctag                    465

<210> SEQ ID NO 55
<211> LENGTH: 153
<212> TYPE: PRT
<213> ORGANISM: Artificial Sequence
<220> FEATURE:
<223> OTHER INFORMATION: Synthetic polypeptide

<400> SEQUENCE: 55

Met Gln Leu Tyr Ser Arg Thr Ser Gly Lys His Ile Gln Val Leu Gly

```
            1               5                  10                  15
         Arg Arg Ile Ser Ala Arg Gly Glu Asp Gly Asp Lys Tyr Ala Gln Leu
                        20                  25                  30

Leu Val Glu Thr Asp Thr Phe Gly Ser Gln Val Arg Ile Lys Gly Lys
                        35                  40                  45

Glu Thr Glu Phe Tyr Leu Cys Met Asn Arg Lys Gly Lys Leu Val Gly
                        50                  55                  60

Lys Pro Asp Gly Thr Ser Lys Glu Cys Val Phe Ile Glu Lys Val Leu
         65                     70                  75                  80

Glu Asn Asn Tyr Thr Ala Leu Met Ser Ala Lys Tyr Ser Gly Trp Tyr
                        85                  90                  95

Val Gly Phe Thr Lys Lys Gly Arg Pro Arg Lys Gly Pro Lys Thr Arg
                        100                 105                 110

Glu Asn Gln Gln Asp Val His Phe Met Lys Arg Tyr Pro Lys Gly Gln
                        115                 120                 125

Pro Glu Leu Gln Lys Pro Phe Lys Tyr Thr Thr Val Thr Lys Arg Ser
                        130                 135                 140

Arg Arg Ile Arg Pro Thr His Pro Ala
         145                     150

<210> SEQ ID NO 56
<211> LENGTH: 462
<212> TYPE: DNA
<213> ORGANISM: Artificial Sequence
<220> FEATURE:
<223> OTHER INFORMATION: Synthetic polynucleotide

<400> SEQUENCE: 56
atgcagctct acagccggac cagtgggaaa cacatccagg tcctgggccg caggatcagt      60
gcccgcggcg aggatgggga caagtatgcc cagctcctag tggagacaga caccttcggt     120
agtcaagtcc ggatcaaggg caaggagacg gaattctacc tgtgcatgaa ccgcaaaggc     180
aagctcgtgg ggaagcccga tggcaccagc aaggagtgtg tgttcatcga aaaggttctg     240
gagaacaact acacggccct gatgtcggct aagtactccg gctggtacgt gggcttcacc     300 aagaagggc ggccgcggaa gggccccaag acccgggaga ccagcagga cgtgcatttc      360 atgaagcgct accccaaggg gcagccggag cttcagaagc ccttcaagta cacgacggtg     420
accaagaggt cccgtcggat caggcccaca caccctgcct ag                       462

<210> SEQ ID NO 57
<211> LENGTH: 152
<212> TYPE: PRT
<213> ORGANISM: Artificial Sequence
<220> FEATURE:
<223> OTHER INFORMATION: Synthetic polypeptide

<400> SEQUENCE: 57

Met Leu Tyr Ser Arg Thr Ser Gly Lys His Ile Gln Val Leu Gly Arg
         1               5                   10                  15

Arg Ile Ser Ala Arg Gly Glu Asp Gly Asp Lys Tyr Ala Gln Leu Leu
                        20                  25                  30

Val Glu Thr Asp Thr Phe Gly Ser Gln Val Arg Ile Lys Gly Lys Glu
                        35                  40                  45

Thr Glu Phe Tyr Leu Cys Met Asn Arg Lys Gly Lys Leu Val Gly Lys
                        50                  55                  60

Pro Asp Gly Thr Ser Lys Glu Cys Val Phe Ile Glu Lys Val Leu Glu
         65                     70                  75                  80
```

Asn Asn Tyr Thr Ala Leu Met Ser Ala Lys Tyr Ser Gly Trp Tyr Val
                85                  90                  95

Gly Phe Thr Lys Lys Gly Arg Pro Arg Lys Gly Pro Lys Thr Arg Glu
            100                 105                 110

Asn Gln Gln Asp Val His Phe Met Lys Arg Tyr Pro Lys Gly Gln Pro
        115                 120                 125

Glu Leu Gln Lys Pro Phe Lys Tyr Thr Thr Val Thr Lys Arg Ser Arg
    130                 135                 140

Arg Ile Arg Pro Thr His Pro Ala
145                 150

<210> SEQ ID NO 58
<211> LENGTH: 459
<212> TYPE: DNA
<213> ORGANISM: Artificial Sequence
<220> FEATURE:
<223> OTHER INFORMATION: Synthetic polynucleotide

<400> SEQUENCE: 58
atgctctaca gccggaccag tgggaaacac atccaggtcc tgggccgcag gatcagtgcc      60
cgcggcgagg atgggcacaa gtatgcccag ctcctagtgg agacagacac cttcggtagt     120
caagtccgga tcaagggcaa ggagacggaa ttctacctgt gcatgaaccg caaaggcaag     180
ctcgtgggga agcccgatgg caccagcaag gagtgtgtgt tcatcgagaa ggttctggag     240
aacaactaca cggccctgat gtcggctaag tactccggct ggtacgtggg cttcaccaag     300
aaggggcggc gcggaagggg ccccaagacc cgggagaacc agcaggacgt gcatttcatg     360
aagcgctacc ccaaggggca gccggagctt cagaagccct tcaagtacac gacggtgacc     420
aagaggtccc gtcggatcag gcccacacac cctgcctag                            459

<210> SEQ ID NO 59
<211> LENGTH: 549
<212> TYPE: DNA
<213> ORGANISM: Artificial Sequence
<220> FEATURE:
<223> OTHER INFORMATION: Synthetic polynucleotide

<400> SEQUENCE: 59
atggccgagg agaacgtgga cttccgcatc cacgtggaga accagacgcg ggctcgggac      60
gatgtgagcc gtaagcagct gcggctgtac cagctctaca gccggaccag tgggaaacac     120
atccaggtcc tgggccgcag gatcagtgcc cgcggcgagg atgggcacaa gtatgcccag     180
ctcctagtgg agacagacac cttcggtagt caagtccgga tcaagggcaa ggagacggaa     240
ttctacctgt gcatgaaccg caaaggcaag ctcgtgggga agcccgatgg caccagcaag     300
gagtgtgtgt tcatcgagaa ggttctggag aacaactaca cggccctgat gtcggctaag     360
tactccggct ggtacgtggg cttcaccaag aaggggcggc gcggaagggg ccccaagacc     420
cgggagaacc agcaggacgt gcatttcatg aagcgctacc ccaaggggca gccggagctt     480
cagaagccct tcaagtacac gacggtgacc aagaggtccc gtcggatccg gcccacacac     540
cctgcctag                                                             549

<210> SEQ ID NO 60
<211> LENGTH: 30
<212> TYPE: DNA
<213> ORGANISM: Artificial Sequence
<220> FEATURE:
<223> OTHER INFORMATION: Primer

```
<400> SEQUENCE: 60
ggaattccat atggagaacc agacgcgggc                                    30

<210> SEQ ID NO 61
<211> LENGTH: 27
<212> TYPE: DNA
<213> ORGANISM: Artificial Sequence
<220> FEATURE:
<223> OTHER INFORMATION: Primer

<400> SEQUENCE: 61
acgtggatcc ctaggcaggg tgtgtgg                                       27

<210> SEQ ID NO 62
<211> LENGTH: 31
<212> TYPE: DNA
<213> ORGANISM: Artificial Sequence
<220> FEATURE:
<223> OTHER INFORMATION: Primer

<400> SEQUENCE: 62
ggaattccat atggatgtga gccgtaagca g                                  31

<210> SEQ ID NO 63
<211> LENGTH: 31
<212> TYPE: DNA
<213> ORGANISM: Artificial Sequence
<220> FEATURE:
<223> OTHER INFORMATION: Primer

<400> SEQUENCE: 63
ggaattccat atgctgcggc tgtaccagct c                                  31

<210> SEQ ID NO 64
<211> LENGTH: 29
<212> TYPE: DNA
<213> ORGANISM: Artificial Sequence
<220> FEATURE:
<223> OTHER INFORMATION: Primer

<400> SEQUENCE: 64
ggaattccat atggccgagg agaacgtgg                                     29

<210> SEQ ID NO 65
<211> LENGTH: 29
<212> TYPE: DNA
<213> ORGANISM: Artificial Sequence
<220> FEATURE:
<223> OTHER INFORMATION: Primer

<400> SEQUENCE: 65
ggaattccat atggacttcc gcatccacg                                     29

<210> SEQ ID NO 66
<211> LENGTH: 31
<212> TYPE: DNA
<213> ORGANISM: Artificial Sequence
<220> FEATURE:
<223> OTHER INFORMATION: Primer

<400> SEQUENCE: 66
ggaattccat atgcgcatcc acgtggagaa c                                  31

<210> SEQ ID NO 67
```

<211> LENGTH: 157
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: X is an amino acid other than leucine, for example isoleucine, valine or methionine.

<400> SEQUENCE: 67

```
Met Xaa Arg Leu Tyr Gln Leu Tyr Ser Arg Thr Ser Gly Lys His Ile
1               5                   10                  15

Gln Val Leu Gly Arg Arg Ile Ser Ala Arg Gly Glu Asp Gly Asp Lys
            20                  25                  30

Tyr Ala Gln Leu Leu Val Glu Thr Asp Thr Phe Gly Ser Gln Val Arg
        35                  40                  45

Ile Lys Gly Lys Glu Thr Glu Phe Tyr Leu Cys Met Asn Arg Lys Gly
50                  55                  60

Lys Leu Val Gly Lys Pro Asp Gly Thr Ser Lys Glu Cys Val Phe Ile
65                  70                  75                  80

Glu Lys Val Leu Glu Asn Asn Tyr Thr Ala Leu Met Ser Ala Lys Tyr
                85                  90                  95

Ser Gly Trp Tyr Val Gly Phe Thr Lys Lys Gly Arg Pro Arg Lys Gly
            100                 105                 110

Pro Lys Thr Arg Glu Asn Gln Gln Asp Val His Phe Met Lys Arg Tyr
        115                 120                 125

Pro Lys Gly Gln Pro Glu Leu Gln Lys Pro Phe Lys Tyr Thr Thr Val
    130                 135                 140

Thr Lys Arg Ser Arg Arg Ile Arg Pro Thr His Pro Ala
145                 150                 155
```

<210> SEQ ID NO 68
<211> LENGTH: 474
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (4)..(6)
<223> OTHER INFORMATION: NNN is a codon coding for an amino acid other than leucine, for example isoleucine, valine or methionine.

<400> SEQUENCE: 68

```
atgnnncggc tgtaccagct ctacagccgg accagtggga acacatcca ggtcctgggc      60
cgcaggatca gtgcccgcgg cgaggatggg acaagtatg cccagctcct agtggagaca     120
gacaccttcg gtagtcaagt ccggatcaag ggcaaggaga cggaattcta cctgtgcatg    180
aaccgcaaag gcaagctcgt ggggaagccc gatggcacca gcaaggagtg tgtgttcatc    240
gagaaggttc tggagaacaa ctacacggcc ctgatgtcgg ctaagtactc cggctggtac    300
gtgggcttca ccaagaaggg gcggccgcgg aagggcccca agacccggga gaaccagcag    360
gacgtgcatt tcatgaagcg ctaccccaag gggcagccgg agcttcagaa gcccttcaag    420
tacacgacgg tgaccaagag gtcccgtcgg atcaggccca cacccctgc ctag           474
```

<210> SEQ ID NO 69
<211> LENGTH: 157
<212> TYPE: PRT
<213> ORGANISM: Artificial Sequence

```
<220> FEATURE:
<223> OTHER INFORMATION: Synthetic polypeptide

<400> SEQUENCE: 69

Met Ile Arg Leu Tyr Gln Leu Tyr Ser Arg Thr Ser Gly Lys His Ile
1               5                   10                  15

Gln Val Leu Gly Arg Arg Ile Ser Ala Arg Gly Glu Asp Gly Asp Lys
            20                  25                  30

Tyr Ala Gln Leu Leu Val Glu Thr Asp Thr Phe Gly Ser Gln Val Arg
        35                  40                  45

Ile Lys Gly Lys Glu Thr Glu Phe Tyr Leu Cys Met Asn Arg Lys Gly
50                  55                  60

Lys Leu Val Gly Lys Pro Asp Gly Thr Ser Lys Glu Cys Val Phe Ile
65                  70                  75                  80

Glu Lys Val Leu Glu Asn Asn Tyr Thr Ala Leu Met Ser Ala Lys Tyr
                85                  90                  95

Ser Gly Trp Tyr Val Gly Phe Thr Lys Lys Gly Arg Pro Arg Lys Gly
            100                 105                 110

Pro Lys Thr Arg Glu Asn Gln Gln Asp Val His Phe Met Lys Arg Tyr
        115                 120                 125

Pro Lys Gly Gln Pro Glu Leu Gln Lys Pro Phe Lys Tyr Thr Thr Val
    130                 135                 140

Thr Lys Arg Ser Arg Arg Ile Arg Pro Thr His Pro Ala
145                 150                 155

<210> SEQ ID NO 70
<211> LENGTH: 474
<212> TYPE: DNA
<213> ORGANISM: Artificial Sequence
<220> FEATURE:
<223> OTHER INFORMATION: Synthetic polynucleotide

<400> SEQUENCE: 70
atgatacggc tgtaccagct ctacagccgg accagtggga aacacatcca ggtcctgggc      60
cgcaggatca gtgcccgcgg cgaggatggg acaagtatg cccagctcct agtggagaca     120
gacaccttcg gtagtcaagt ccggatcaag ggcaaggaga cggaattcta cctgtgcatg     180
aaccgcaaag gcaagctcgt ggggaagccc gatggcacca gcaaggagtg tgtgttcatc     240
gagaaggttc tggagaacaa ctacacggcc ctgatgtcgg ctaagtactc cggctggtac     300
gtgggcttca ccaagaaggg gcggccgcgg aagggcccca agacccggga gaaccagcag     360
gacgtgcatt tcatgaagcg ctaccccaag gggcagccgg agcttcagaa gcccttcaag     420
tacacgacgg tgaccaagag gtcccgtcgg atcaggccca cacccctgc ctag            474

<210> SEQ ID NO 71
<211> LENGTH: 624
<212> TYPE: DNA
<213> ORGANISM: Homo sapiens

<400> SEQUENCE: 71
atgtattcag cgccctccgc ctgcacttgc ctgtgtttac acttcctgct gctgtgcttc      60
caggtacagg tgctggttgc cgaggagaac gtggacttcc gcatccacgt ggagaaccag     120
acgcgggctc gggacgatgt gagccgtaag cagctgcggc tgtaccagct ctacagccgg     180
accagtggga aacacatcca ggtcctgggc cgcaggatca gtgcccgcgg cgaggatggg     240 acaagtatg cccagctcct agtggagaca gacaccttcg gtagtcaagt ccggatcaag     300
```

-continued

```
ggcaaggaga cggaattcta cctgtgcatg aaccgcaaag gcaagctcgt ggggaagccc    360
gatggcacca gcaaggagtg tgtgttcatc gagaaggttc tggagaacaa ctacacggcc    420
ctgatgtcgg ctaagtactc cggctggtac gtgggcttca ccaagaaggg gcggccgcgg    480
aagggcccca agacccggga gaaccagcag gacgtgcatt tcatgaagcg ctaccccaag    540
gggcagccgg agcttcagaa gcccttcaag tacacgacgg tgaccaagag gtcccgtcgg    600
atccggccca cacaccctgc ctag                                           624
```

FGF-18 TRUNCATED VARIANTS HAVING INCREASED RECEPTOR SPECIFICITY AND USES THEREOF

FIELD OF THE INVENTION

The present invention relates to fibroblast growth factor 18 (FGF-18) variants, which activate FGFR3 with increased specificity. In particular, the invention relates to FGF-18 variants having various truncations beyond the signal peptide domain of the N-terminus, nucleic acids encoding the variants, pharmaceutical compositions comprising same and methods of use thereof.

BACKGROUND OF THE INVENTION

Fibroblast Growth Factors and their Receptors

Fibroblast growth factors (FGFs) comprise a large family of evolutionarily conserved polypeptides involved in a variety of biological processes including morphogenesis, angiogenesis, and tissue remodeling as well as in the pathogenesis of numerous diseases. The various members of this family stimulate the proliferation of a wide spectrum of cells, including those deriving from mesenchymal, endothelial, epithelial and neuroectodermal origin. FGFs are expressed in a strict temporal and spatial pattern during development and have important roles in patterning and limb formation (Ornitz, Bioessays, 2000, Vol. 22, p. 108). All members of the FGF family share a homology core domain of about 120 amino acids, 28 aa residues are highly conserved and four are identical. The adjacent N- and C-termini are of variable length and share limited homology. The core domain comprises both the primary receptor binding sites and a heparin-binding domain, which are distinct from each other (Ornitz and Itoh, Gen. Biol., 2001, Vol. 2, No. 3, p. 30005).

Fibroblast growth factor 18 (FGF-18), is highly conserved between humans and mice and is most homologous to FGF-8 among the FGF family members. FGF-18 is primarily expressed in the lungs and kidneys and at lower levels in the heart, testes, spleen, skeletal muscle, and brain. The first 27 amino acids of the human and mouse FGF-18 protein are hydrophobic residues that are predicted to be signal peptides for secretion. FGF-18 further contains two potential N-linked glycosylation sites and it was glycosylated and secreted when it was transfected into 293-EBNA cells. Glycosylation was determined not to be critical for FGF-18 activity as the glycosylated (mammalian cells expressed) and non-glycosylated (*E. coli* expressed) FGF-18 showed similar activity on target cells (Hu et al., Molecular and Cellular Biology, 1998, Vol. 18, No. 10, p. 6063). WO 2006/063362 discloses expression vectors and methods using an *E. coli* expression system for the large scale production of FGF-18. Initially, FGF-18 was disclosed as being a pleiotropic growth factor that stimulates proliferation in a number of tissues, most notably the liver and small intestine (Hu et al., Molecular and Cellular Biology, 1998, Vol. 18, No. 10, p. 6063). US 2008/0193425 discloses a composition for intra-articular delivery of chondrogenic polypeptides comprising a pharmaceutically acceptable admixture comprising FGF-18 and hyaluronic acid. US 2010/0016223 discloses the treatment of cartilage disorder and osteoarthritis in particular, using FGF-18 and truncated variants which comprise or consist of residues 28 to 175-207.

The biological response of cells to FGF is mediated through specific, high affinity (Kd 20-500 pM) cell surface receptors that possess intrinsic tyrosine kinase activity and are phosphorylated upon binding to FGF. Five distinct Fibroblast Growth Factor Receptors (FGFRs) have been identified, FGFR1-4 are transmembrane-protein kinases while FGFR5 lacks a tyrosine kinase domain. The FGFR extracellular domain consists of three immunoglobulin-like (Ig-like) domains (D1, D2 and D3), a heparin binding domain and an acidic box. Alternative splicing of D3 in FGFR1-3 mRNAs generates six different receptor subtypes, each having unique ligand specificity and tissue distribution pattern. Most naturally occurring FGF ligands share the capacity to bind multiple FGF receptors. Fibroblast growth factor-18 (FGF-18) binds to FGF receptors-2 and -3. Compositions comprising an FGF-18 component can be used to target cells including tumor cells that express constitutively activated forms of FGF receptors-2 and -3 (WO 01/39788).

FGF Variants and Receptor Specificity

Attempts have been made to achieve altered FGF receptor specificity by inducing mutations at certain locations within the gene encoding the proteins and/or by inducing truncations in the FGF ligands. WO 02/36732 and WO 03/094835 disclose FGF-9 N- and/or C-terminus truncated variants having enhanced specificity for one receptor subtype compared to the corresponding wild type FGF. WO 03/094835 further discloses an FGF-4 variant having both an N-terminal truncation (55 amino acids) and an amino acid substitution in the β8-β9 loop, the variant exhibiting enhanced receptor specificity towards FGFR3 with substantially unchanged activity towards FGFR1 and FGFR2. WO 08/038,287 discloses FGF-2 and FGF-4 variants having N-terminus truncations which activate only one or two of the FGFR subtypes, preferably FGFR1. Kuroda et al., (Bone, 1999, Vol. 25, p. 431) demonstrated that a full-length FGF4 polypeptide (191 aa) and an N-terminal truncated version containing 134 amino acid residues exhibit comparable cellular proliferation on NIH3T3 cells and increase of bone density. The shortest form of FGF4 tested, containing only 111 amino acid residues, exhibited limited growth stimulatory activity. U.S. Pat. No. 5,998,170 discloses a biologically active FGF-16 molecule having from one to thirty-four amino acids deleted from the N-terminus or from one to eighteen amino acids deleted from the C-terminus. The truncated ligands were shown to retain biological activity including hepatocellular proliferation and increased production of triglycerides and serum proteins, when administered to animals.

X-ray crystallography has been used in an attempt to study the basis of specificity of FGFs to their receptors (Plotnikov et al., Cell, 2000, Vol. 101, p. 413; Olsen, et al., PNAS US, 2004, Vol. 101, p. 935; Mohammadi et al., Cyto. Growth Factor Rev., 2005, Vol. 16, No. 2, p. 107). The role of the N-terminal domain of the FGFs was partially resolved in a few of the abovementioned crystal structures. Olsen et al., (PNAS US, 2004, Vol. 101, p. 935) compared receptor binding of a full length FGF-1 (155 aa) to an N-terminal truncated form (21-155) and showed that the N-terminus of FGF-1 may be relevant to binding and activation of the FGFR3c isoform. The (21-155) form also exhibits reduced FGFR2 and FGFR3 phosphorylation. Plotnikov et al., (Plotnikov et al., Cell, 2000, Vol. 101, p. 413) determined the crystal structures of FGF-1 and FGF-2 complexed with the ligand binding domains (Ig-like domains 2 and 3) of FGFR1 and FGFR2, respectively and showed that certain N-terminal residues of FGF, in particular Phe17 and Lys18 of FGF-2 (Lys27 of 155 aa form), could be in contact with the D3 domain of FGFR2. The authors speculated that amino acids 7-13 of FGF-1 play a role in receptor binding. The deletion of that specific sequence, which had originally been proposed to be a nuclear localization sequence, reduces the ability of FGF-1 to induce cell proliferation in endothelial cell lines by about 250-fold (Imamura et al., Science, 1990, Vol. 249, p. 1567). Seno et al., (Eur. J. Biochem. 1990, Vol. 188, p. 239) disclosed certain FGF-2 variants having N- and C-terminus truncations and have characterized their ability to bind heparin. The mitogenic activity of those variants in BALB/c3T3 cells was determined and the N14 variant (corresponding to a 22 amino acid truncation of the 155 aa bFGF species) showed an activity of 68% of the mature form of bFGF. A much larger truncation, N41, which corresponds to a 49 amino acid truncation of the 155 aa species, exhibits only about 2% mitogenic activity.

Attempts have been made to alter FGF receptor specificity and heparin binding by means of site directed mutagenesis within the FGF genes. U.S. Pat. No. 5,512,460 discloses a biologically active FGF-9 (glia activating factor, GAF) molecule comprising N-terminus and C-terminus truncations of 53 aa and 13 aa, respectively. U.S. Pat. No. 5,571,895 discloses an N-terminus 54 aa deletion yielding a 154 aa protein retaining its biological activity, as measured by glial cell growth activity. Bellosta et al., (Mol. Cell. Biol., 2001, Vol. 21, No. 17, p. 5946) disclosed mutated and truncated FGF-4 variants having reduced receptor binding and a low mitogenic potential.

Wild type FGF-18 was found to bind to FGF receptors (FGFRs)-3c and -2c but not to FGFR-1c (Hoshikawa, Brain Res. Mol. Brain Res., 2002, Vol. 105, No. 1-2, p. 60). Yet another paper (Hamidouche et al J Cell Physiol. 2010 Vol. 224(2), p. 509) demonstrates that FGF-18 signaling in mesenchymal stem cells is mediated via FGFR1 and FGFR2. Another study identified a novel mechanism for FGF-18 signaling. It involves an accessory receptor (Cfr) that binds to FGF-18 and increases its affinity towards FGFR3c (Miyaoka et al, Development. 2010 Vol. 137(1), p. 159). Zhang et al. (J. Bio. Chem. 2006, Vol. 281(23), p. 15694) discloses that FGF-18 specifically activates FGFRs 1c, 2c, and 3c and the two Ig-like domain forms of FGFR4. WO 01/39788 discloses FGF-18 peptide that lacks the signal peptide (amino acids 1-27) also known as the mature form of FGF-18, and FGF-18 functional fragments comprising C-terminal truncations as targeting compositions for inhibiting the proliferation of cells including tumor cells that express constitutively activated forms of FGF receptors-2 and -3.

Certain FGFRs have been implicated in certain malignancies and proliferative diseases. FGFR3 is the most frequently mutated oncogene in transitional cell carcinoma (TCC) of the bladder where it is mutated in about 50% of the cases; the FGFR3IIIc isoform is ectopically expressed in 15-20% of patients with multiple myeloma and is over expressed in the white blood cells of chronic myeloid leukemia (CML) patients. FGFR3IIIc isoform is also implicated in mediation of colorectal cancer growth and migration (Sonvilla et al, British Journal of Cancer 2010, Vol. 102, p. 1145). Single nucleotide polymorphisms (SNPs) of FGFR2 are associated with increased risk of breast cancer (Katoh, Inter. J. Oncol., 2008, Vol. 33, No. 2, p. 233). Mutations in FGFR2 and FGFR3 genes are associated with human gastric and colorectal cancers (Jang et al., Cancer Res., 2001, Vol. 61, p. 3541). A mutation in FGFR3 is linked to cervical carcinoma. FGFR4 was shown to be associated with pituitary tumors and breast cancer progression. FGF-18 is known to stimulate the proliferation of chondrocytes resulting in an increased cartilage formation (Davidson et al., The Journal of Biological Chemistry, 2005, Vol. 280, No. 21, p. 20509).

There remains an unmet need for highly selective FGF variants, useful in selective stimulation or inhibition of FGF receptor subtypes, thus being useful in treating cartilage and skeletal disorders.

SUMMARY OF THE INVENTION

The present invention provides Fibroblast Growth Factor 18 (FGF-18) N-terminal truncated polypeptides that show an increase in receptor specificity for FGF receptor 3 when compared to the corresponding wild type polypeptide. In particular, the invention provides FGF-18 polypeptides having an N-terminal truncation beyond the signal peptide domain, polynucleotides encoding same, pharmaceutical compositions comprising the polypeptides or polynucleotide encoding same, and use thereof in treating cartilage and skeletal disorders.

The present invention is based in part on the unexpected finding that certain N-terminal truncated variants of the mature form of FGF-18 have enhanced receptor specificity for FGFR3 thus affording selective activation of FGFR3. The selective activation of FGFR3 has now been shown to inhibit proliferation of chondrocytes while affording chondrocyte differentiation. The FGF-18 truncated polypeptides of the present invention provide chondrogenic differentiation for specific treatment of cartilage disorders.

According to one aspect, the present invention provides an isolated FGF-18 polypeptide having an N-terminal truncation, wherein the N-terminal truncation is extending beyond the signal peptide, and wherein the polypeptide has increased receptor selectivity when compared to the isolated wild-type FGF-18 polypeptide by a gain of activity or loss of activity by at least a factor of two toward at least one receptor subtype but not toward all FGFR subtypes. In one embodiment, the N-terminal truncated FGF-18 polypeptides are specific to FGFR3.

The sequence of native FGF-18 including the signal peptide is set forth in SEQ ID NO: 1 and shown in FIG. 1. The signal peptide, the R34-H36 basic cluster 1 (BC1), the R42-R44 basic cluster 2 (BC2), and the R49-K50 basic cluster 3 (BC3) are underlined. The sequence of the polynucleotide encoding native FGF-18 which includes the signal peptide is set forth in SEQ ID NO: 71. The sequence of the recombinant wild-type mature FGF-18 (without the signal peptide) is set forth in SEQ ID NO: 2. The corresponding polynucleotide sequence is set forth in SEQ ID NO: 59.

In some embodiments, the N-terminus of the isolated FGF-18 polypeptide of the present invention retains between 0 and 28 amino acid residues extending beyond the core domain.

In one embodiment, the isolated FGF-18 polypeptide having an N-terminal truncation comprises an amino acid sequence as set forth in SEQ ID NO: 11. In other embodiments, the isolated FGF-18 polypeptide having an N-terminal truncation comprises an amino acid sequence as set forth in SEQ ID NO: 19. In other embodiments, the isolated FGF-18 polypeptide having an N-terminal truncation comprises an amino acid sequence as set forth in SEQ ID NO: 35. In yet other embodiments, the isolated FGF-18 polypeptide having an N-terminal truncation comprises an amino acid sequence as set forth in SEQ ID NO: 47. In certain embodiments, the isolated FGF-18 polypeptide having an N-terminal truncation consists of an amino acid sequence as set forth in any one of SEQ ID NOS: 11, 19, 35 or 47. Each possibility represents a separate embodiment of the present invention.

A description of the FGF-18 N-terminal truncated polypeptides of the present invention is set forth hereinbelow. It is to be noted that the N-terminal methionine residue (Met) is required for expression in the bacterial expression system, yet it is generally post-translationally cleaved and a polypeptide lacking the first Met is obtained. However, it is to be understood that FGF-18 polypeptides having the N-terminal methionine are encompassed within the scope of the present application.

The FGF-18 N-terminal truncated polypeptides are characterized as follows:

SEQ ID NO: 3, represents FGF-18$^{\Delta 29}$, having a 28 amino acid N-terminal truncation with the Glu29 replaced by a Met residue. This polypeptide is encoded by a polynucleotide sequence as set forth in SEQ ID NO: 4. It is to be understood that the amino acid numbering includes the signal peptide located at amino acids positions 1-27.

SEQ ID NO: 5, represents FGF-18$^{\Delta 30}$, having a 29 amino acid N-terminal truncation with the Asn30 replaced by a Met residue. This polypeptide is encoded by a polynucleotide sequence as set forth in SEQ ID NO: 6. It is to be understood that the amino acid numbering includes the signal peptide located at amino acids positions 1-27.

SEQ ID NO: 7, represents FGF-18$^{\Delta 31}$, having a 30 amino acid N-terminal truncation with the Val31 replaced by a Met residue. This polypeptide is encoded by a polynucleotide sequence as set forth in SEQ ID NO: 8. It is to be understood that the amino acid numbering includes the signal peptide located at amino acids positions 1-27.

SEQ ID NO: 9, represents FGF-18$^{\Delta 32}$, having a 31 amino acid N-terminal truncation with the Asp32 replaced by a Met residue. This polypeptide is encoded by a polynucleotide sequence as set forth in SEQ ID NO: 10. It is to be understood that the amino acid numbering includes the signal peptide located at amino acids positions 1-27.

SEQ ID NO: 11, represents FGF-18$^{\Delta 33}$, having a 32 amino acid N-terminal truncation with the Phe33 replaced by a Met residue. This polypeptide is encoded by a polynucleotide sequence as set forth in SEQ ID NO: 12. It is to be understood that the amino acid numbering includes the signal peptide located at amino acids positions 1-27.

SEQ ID NO: 13, represents FGF-18$^{\Delta 34}$, having a 33 amino acid N-terminal truncation with the Arg34 replaced by a Met residue. This polypeptide is encoded by a polynucleotide sequence as set forth in SEQ ID NO: 14. It is to be understood that the amino acid numbering includes the signal peptide located at amino acids positions 1-27.

SEQ ID NO: 15, represents FGF-18$^{\Delta 35}$, having a 34 amino acid N-terminal truncation with the Ile35 replaced by a Met residue. This polypeptide is encoded by a polynucleotide sequence as set forth in SEQ ID NO: 16. It is to be understood that the amino acid numbering includes the signal peptide located at amino acids positions 1-27.

SEQ ID NO: 17, represents FGF-18$^{\Delta 36}$, having a 35 amino acid N-terminal truncation with the His36 replaced by a Met residue. This polypeptide is encoded by a polynucleotide sequence as set forth in SEQ ID NO: 18. It is to be understood that the amino acid numbering includes the signal peptide located at amino acids positions 1-27.

SEQ ID NO: 19, represents FGF-18$^{\Delta 37}$, having a 36 amino acid N-terminal truncation with the Val37 replaced by a Met residue. This polypeptide is encoded by a polynucleotide sequence as set forth in SEQ ID NO: 20. It is to be understood that the amino acid numbering includes the signal peptide located at amino acids positions 1-27.

SEQ ID NO: 21, represents FGF-18$^{\Delta 38}$, having a 37 amino acid N-terminal truncation with the Glu38 replaced by a Met residue. This polypeptide is encoded by a polynucleotide sequence as set forth in SEQ ID NO: 22. It is to be understood that the amino acid numbering includes the signal peptide located at amino acids positions 1-27.

SEQ ID NO: 23, represents FGF-18$^{\Delta 39}$, having a 38 amino acid N-terminal truncation with the Asn39 replaced by a Met residue. This polypeptide is encoded by a polynucleotide sequence as set forth in SEQ ID NO: 24. It is to be understood that the amino acid numbering includes the signal peptide located at amino acids positions 1-27.

SEQ ID NO: 25, represents FGF-18$^{\Delta 40}$, having a 39 amino acid N-terminal truncation with the Gln40 replaced by a Met residue. This polypeptide is encoded by a polynucleotide sequence as set forth in SEQ ID NO: 26. It is to be understood that the amino acid numbering includes the signal peptide located at amino acids positions 1-27.

SEQ ID NO: 27, represents FGF-18$^{\Delta 41}$, having a 40 amino acid N-terminal truncation with the Thr41 replaced by a Met residue. This polypeptide is encoded by a polynucleotide sequence as set forth in SEQ ID NO: 28. It is to be understood that the amino acid numbering includes the signal peptide located at amino acids positions 1-27.

SEQ ID NO: 29, represents FGF-18$^{\Delta 42}$, having a 41 amino acid N-terminal truncation with the Arg42 replaced by a Met residue. This polypeptide is encoded by a polynucleotide sequence as set forth in SEQ ID NO: 30. It is to be understood that the amino acid numbering includes the signal peptide located at amino acids positions 1-27.

SEQ ID NO: 31, represents FGF-18$^{\Delta 43}$, having a 42 amino acid N-terminal truncation with the Ala43 replaced by a Met residue. This polypeptide is encoded by a polynucleotide sequence as set forth in SEQ ID NO: 32. It is to be understood that the amino acid numbering includes the signal peptide located at amino acids positions 1-27.

SEQ ID NO: 33, represents FGF-18$^{\Delta 44}$, having a 43 amino acid N-terminal truncation with the Arg44 replaced by a Met residue. This polypeptide is encoded by a polynucleotide sequence as set forth in SEQ ID NO: 34. It is to be understood that the amino acid numbering includes the signal peptide located at amino acids positions 1-27.

SEQ ID NO: 35, represents FGF-18$^{\Delta 45}$, having a 44 amino acid N-terminal truncation with the Asp45 replaced by a Met residue. This polypeptide is encoded by a polynucleotide sequence as set forth in SEQ ID NO: 36. It is to be understood that the amino acid numbering includes the signal peptide located at amino acids positions 1-27.

SEQ ID NO: 37, represents FGF-18$^{\Delta 46}$, having a 45 amino acid N-terminal truncation with the Asp46 replaced by a Met residue. This polypeptide is encoded by a polynucleotide sequence as set forth in SEQ ID NO: 38. It is to be understood that the amino acid numbering includes the signal peptide located at amino acids positions 1-27.

SEQ ID NO: 39, represents FGF-18$^{\Delta 47}$, having a 46 amino acid N-terminal truncation with the Val47 replaced by a Met residue. This polypeptide is encoded by a polynucleotide sequence as set forth in SEQ ID NO: 40. It is to be understood that the amino acid numbering includes the signal peptide located at amino acids positions 1-27.

SEQ ID NO: 41, represents FGF-18$^{\Delta 48}$, having a 47 amino acid N-terminal truncation with the Ser48 replaced by a Met residue. This polypeptide is encoded by a polynucleotide sequence as set forth in SEQ ID NO: 42. It is to be understood that the amino acid numbering includes the signal peptide located at amino acids positions 1-27.

SEQ ID NO: 43, represents FGF-18$^{\Delta 49}$, having a 48 amino acid N-terminal truncation with the Arg49 replaced by a Met residue. This polypeptide is encoded by a polynucleotide sequence as set forth in SEQ ID NO: 44. It is to be understood that the amino acid numbering includes the signal peptide located at amino acids positions 1-27.

SEQ ID NO: 45, represents FGF-18$^{\Delta 50}$, having a 49 amino acid N-terminal truncation with the Lys50 replaced by a Met residue. This polypeptide is encoded by a polynucleotide sequence as set forth in SEQ ID NO: 46. It is to be understood that the amino acid numbering includes the signal peptide located at amino acids positions 1-27.

SEQ ID NO: 47, represents FGF-18$^{\Delta 51}$, having a 50 amino acid N-terminal truncation with the Gln51 replaced by a Met residue. This polypeptide is encoded by a polynucleotide sequence as set forth in SEQ ID NO: 48. It is to be understood that the amino acid numbering includes the signal peptide located at amino acids positions 1-27.

SEQ ID NO: 49, represents FGF-18$^{\Delta 52}$, having a 51 amino acid N-terminal truncation with the Leu52 replaced by a Met residue. This polypeptide is encoded by a polynucleotide sequence as set forth in SEQ ID NO: 50. It is to be understood that the amino acid numbering includes the signal peptide located at amino acids positions 1-27.

SEQ ID NO: 51, represents FGF-18$^{\Delta 53}$, having a 52 amino acid N-terminal truncation with the Arg53 replaced by a Met residue. This polypeptide is encoded by a polynucleotide sequence as set forth in SEQ ID NO: 52. It is to be understood that the amino acid numbering includes the signal peptide located at amino acids positions 1-27.

SEQ ID NO: 53, represents FGF-18$^{\Delta 54}$, having a 53 amino acid N-terminal truncation with the Leu54 replaced by a Met residue. This polypeptide is encoded by a polynucleotide sequence as set forth in SEQ ID NO: 54. It is to be understood that the amino acid numbering includes the signal peptide located at amino acids positions 1-27.

SEQ ID NO: 55, represents FGF-18$^{\Delta 55}$, having a 54 amino acid N-terminal truncation with the Tyr55 replaced by a Met residue. This polypeptide is encoded by a polynucleotide sequence as set forth in SEQ ID NO: 56. It is to be understood that the amino acid numbering includes the signal peptide located at amino acids positions 1-27.

SEQ ID NO: 57, represents FGF-18$^{\Delta 56}$, having a 55 amino acid N-terminal truncation with the Gln56 replaced by a Met residue. This polypeptide is encoded by a polynucleotide sequence as set forth in SEQ ID NO: 58. It is to be understood that the amino acid numbering includes the signal peptide located at amino acids positions 1-27.

In some embodiments, the isolated FGF-18 polypeptide of the present invention further comprises at least one additional modification in its polypeptide sequence, wherein the modification is selected from an amino acid deletion, an amino acid substitution and an amino acid insertion. Each possibility represents a separate embodiment of the invention. In one embodiment, the additional modification is an amino acid residue substitution in the retained N-terminus sequence. In another embodiment, the amino acid substitution is a conservative substitution. In further embodiments, the isolated FGF-18 polypeptide comprises an amino acid sequence as set forth in SEQ ID NO: 67 representing FGF-18$^{\Delta 51L52X}$, having a 50 amino acid N-terminal truncation with the Gln51 replaced by a Met residue and further having the Leu52 replaced by an amino acid residue other than leucine. In specific embodiments, the Leu52 is replaced by an amino acid residue selected from isoleucine, valine and methionine. Each possibility represents a separate embodiment of the present invention. It is to be understood that the amino acid numbering includes the signal peptide located at amino acids positions 1-27. The polypeptide is encoded by a polynucleotide sequence as set forth in SEQ ID NO: 68. In additional embodiments, the isolated FGF-18 polypeptide comprises an amino acid sequence as set forth in SEQ ID NO: 69 representing FGF-18$^{\Delta 51L52I}$, having a 50 amino acid N-terminal truncation with the Gln51 replaced by a Met residue and further having the Leu52 replaced by an Ile residue. It is to be understood that the amino acid numbering includes the signal peptide located at amino acids positions 1-27. The polypeptide is encoded by a polynucleotide sequence as set forth in SEQ ID NO: 70.

It is to be understood explicitly that the isolated FGF-18 polypeptide having an N-terminal truncation as disclosed herein may comprise extensions at the N-terminus other than reinstating those specific N-terminal residues that have been truncated. In other words, the isolated FGF-18 polypeptide of the present invention comprises at least one amino acid deletion at the N-terminus beyond the signal peptide. The isolated FGF-18 N-terminal truncated polypeptides of the present invention may further comprise at least one additional modification in the polypeptide sequence as described herein.

According to another aspect, the present invention provides an isolated polynucleotide encoding an FGF-18 polypeptide having an N-terminal truncation, wherein the N-terminal truncation is extending beyond the signal peptide, and wherein the polypeptide has increased receptor selectivity when compared to the isolated wild-type FGF-18 polypeptide by a gain of activity or loss of activity by at least a factor of two toward at least one receptor subtype but not toward all FGFR subtypes.

In various embodiments, the isolated polynucleotide comprises a sequence as set forth in any one of SEQ ID NOS: 4, 6, 8, 10, 12, 14, 16, 18, 20, 22, 24, 26, 28, 30, 32, 34, 36, 38, 40, 42, 44, 46, 48, 50, 52, 54, 56, and 58. Each possibility represents a separate embodiment of the invention. In additional embodiments, the isolated polynucleotide consists of a sequence as set forth in any one of SEQ ID NOS: 4, 6, 8, 10, 12, 14, 16, 18, 20, 22, 24, 26, 28, 30, 32, 34, 36, 38, 40, 42, 44, 46, 48, 50, 52, 54, 56, and 58. Each possibility represents a separate embodiment of the invention.

In certain embodiments, the present invention provides an isolated polynucleotide encoding an FGF-18 polypeptide having an N-terminal truncation, wherein the N-terminal truncation is extending beyond the signal peptide, and further having at least one additional modification in its polypeptide sequence, wherein the modification is selected from an amino acid deletion, an amino acid substitution and an amino acid insertion, wherein the polypeptide has increased receptor selectivity when compared to the isolated wild-type FGF-18 polypeptide by a gain of activity or loss of activity by at least a factor of two toward at least one receptor subtype but not toward all FGFR subtypes. In one embodiment, the isolated polynucleotide encodes an FGF-18 polypeptide having an N-terminal truncation, wherein the N-terminal truncation is extending beyond the signal peptide, and further having at least one amino acid residue substitution in the retained N-terminus sequence.

In other embodiments, the present invention provides a vector comprising a polynucleotide encoding an FGF-18 polypeptide having an N-terminal truncation as disclosed herein.

In other embodiments, the present invention provides a host cell comprising a vector, the vector comprising a polynucleotide encoding an FGF-18 polypeptide having an N-terminal truncation as disclosed herein.

In another aspect, the present invention provides a pharmaceutical composition comprising as an active ingredient at least one isolated FGF-18 polypeptide having an N-terminal truncation, wherein the N-terminal truncation is extending beyond the signal peptide, and wherein the polypeptide has increased receptor selectivity when compared to the isolated wild-type FGF-18 polypeptide by a gain of activity or loss of activity by at least a factor of two toward at least one receptor subtype but not toward all FGFR subtypes; and a pharmaceutically acceptable diluent or carrier.

In one embodiment, the pharmaceutical composition comprises at least one isolated FGF-18 polypeptide having an N-terminal truncation, wherein the polypeptide comprises an amino acid sequence as set forth in SEQ ID NO: 11, and a pharmaceutically acceptable diluent or carrier. In another embodiment, the pharmaceutical composition comprises at least one isolated FGF-18 polypeptide having an N-terminal truncation, wherein the polypeptide comprises an amino acid sequence as set forth in SEQ ID NO: 19; and a pharmaceutically acceptable diluent or carrier. In another embodiment, the pharmaceutical composition comprises at least one isolated FGF-18 polypeptide having an N-terminal truncation, wherein the polypeptide comprises an amino acid sequence as set forth in SEQ ID NO: 35; and a pharmaceutically acceptable diluent or carrier. In yet another embodiment, the pharmaceutical composition comprises at least one isolated FGF-18 polypeptide having an N-terminal truncation, wherein the polypeptide comprises an amino acid sequence as set forth in SEQ ID NO: 47; and a pharmaceutically acceptable diluent or carrier.

In further embodiments, the present invention provides a pharmaceutical composition comprising as an active ingredient at least one isolated FGF-18 polypeptide having an N-terminal truncation, wherein the N-terminal truncation is extending beyond the signal peptide, and further having at least one additional modification in its polypeptide sequence, wherein the modification is selected from an amino acid deletion, an amino acid substitution and an amino acid insertion, wherein the polypeptide has increased receptor selectivity when compared to the isolated wild-type FGF-18 polypeptide by a gain of activity or loss of activity by at least a factor of two toward at least one receptor subtype but not toward all FGFR subtypes; and a pharmaceutically acceptable diluent or carrier. In some embodiments, the pharmaceutical composition comprises an FGF-18 polypeptide having an N-terminal truncation, wherein the N-terminal truncation is extending beyond the signal peptide, and further having at least one amino acid residue substitution in the retained N-terminus sequence; and a pharmaceutically acceptable diluent or carrier. In specific embodiments, the pharmaceutical composition comprises at least one isolated FGF-18 polypeptide comprising an amino acid sequence as set forth in SEQ ID NO: 67; and a pharmaceutically acceptable diluent or carrier. In other embodiments, the pharmaceutical composition comprises at least one isolated FGF-18 polypeptide comprising an amino acid sequence as set forth in SEQ ID NO: 69; and a pharmaceutically acceptable diluent or carrier.

In certain embodiments, the FGF-18 N-terminal truncated polypeptides of the present invention are admixed with at least one bioactive agent. In some embodiments, the at least one bioactive agent is a carboxylated polysaccharide. In particular embodiments, the carboxylated polysaccharide is hyaluronic acid. In additional embodiments, the at least one bioactive agent is a natriuretic peptide. In an exemplary embodiment, the at least one bioactive agent is a C-type natriuretic peptide.

According to another aspect, the present invention provides a pharmaceutical composition comprising as an active ingredient at least one isolated polynucleotide encoding an FGF-18 polypeptide having an N-terminal truncation, wherein the N-terminal truncation is extending beyond the signal peptide, and wherein the polypeptide has increased receptor selectivity when compared to the isolated wild-type FGF-18 polypeptide by a gain of activity or loss of activity by at least a factor of two toward at least one receptor subtype but not toward all FGFR subtypes; and a pharmaceutically acceptable diluent or carrier. In additional embodiments, the pharmaceutical composition comprises as an active ingredient at least one isolated polynucleotide encoding an FGF-18 polypeptide having an N-terminal truncation and further having at least one additional modification in its polypeptide sequence, wherein the modification is selected from an amino acid deletion, an amino acid substitution and an amino acid insertion, for example an amino acid substitution in the retained N-terminus sequence. In specific embodiments, the pharmaceutical composition comprises at least one isolated polynucleotide comprising a sequence as set forth in SEQ ID NO: 68; and a pharmaceutically acceptable diluent or carrier. In other embodiments, the pharmaceutical composition comprises at least one isolated polynucleotide comprising a sequence as set forth in SEQ ID NO: 70; and a pharmaceutically acceptable diluent or carrier.

In one embodiment, the pharmaceutical composition comprises at least one polynucleotide comprising a sequence as set forth in SEQ ID NO: 12; and a pharmaceutically acceptable diluent or carrier. In another embodiment, the pharmaceutical composition comprises at least one polynucleotide comprising a sequence as set forth in SEQ ID NO: 20; and a pharmaceutically acceptable diluent or carrier. In another embodiment, the pharmaceutical composition comprises at least one polynucleotide comprising a sequence as set forth in SEQ ID NO: 36; and a pharmaceutically acceptable diluent or carrier. In yet another embodiment, the pharmaceutical composition comprises at least one polynucleotide comprising a sequence as set forth in SEQ ID NO: 48; and a pharmaceutically acceptable diluent or carrier.

In some embodiments, the pharmaceutical compositions of the present invention are formulated for administration via a route selected from intra-articular, intravenous, intramuscular, subcutaneous, intradermal, and intrathecal route. Each possibility represents a separate embodiment of the invention. In certain embodiments, the pharmaceutical compositions are formulated for administration to the site of a cartilage lesion.

In additional embodiments, the present invention provides a pharmaceutical composition comprising as an active ingredient at least one isolated FGF-18 polypeptide having an N-terminal truncation, wherein the N-terminal truncation is extending beyond the signal peptide, and wherein the polypeptide has increased receptor selectivity when compared to the isolated wild-type FGF-18 polypeptide by a gain of activity or loss of activity by at least a factor of two toward at least one receptor subtype but not toward all FGFR subtypes or a polynucleotide encoding same for inducing cartilage repair, particularly joint cartilage repair. In other embodiments, the compositions of the present invention are useful for treating degenerative joint diseases. In one particular embodiment, the compositions of the present invention are useful in treating osteoarthritis.

In further embodiments, the present invention provides a method of inducing cartilage repair comprising the step of administering to an individual in need thereof a pharmaceutical composition comprising at least one isolated FGF-18 polypeptide having an N-terminal truncation extending beyond the signal peptide or a polynucleotide encoding same. The present invention further provides a method of treating a degenerative joint disease, particularly osteoarthritis, comprising the step of administering to an individual in need thereof a pharmaceutical composition comprising at least one isolated FGF-18 polypeptide having an N-terminal truncation extending beyond the signal peptide or a polynucleotide encoding same. In other embodiments, the present invention provides an isolated FGF-18 polypeptide having an N-terminal truncation extending beyond the signal peptide or a polynucleotide encoding same or a pharmaceutical composition comprising at least one isolated FGF-18 polypeptide as disclosed herein or a pharmaceutical composition comprising at least one polynucleotide encoding same for use in inducing cartilage repair or for use in treating a degenerative joint disease, particularly osteoarthritis. These methods of use of the present invention comprise the administration of a therapeutically effective amount of a polypeptide having an amino acid sequence as set forth in any one of SEQ ID NOS: 3, 5, 7, 9, 11, 13, 15, 17, 19, 21, 23, 25, 27, 29, 31, 33, 35, 37, 39, 41, 43, 45, 47, 49, 51, 53, 55, and 57 or a polynucleotide having a nucleotide sequence as set forth in any one of SEQ ID NOS: 4, 6, 8, 10, 12, 14, 16, 18, 20, 22, 24, 26, 28, 30, 32, 34, 36, 38, 40, 42, 44, 46, 48, 50, 52, 54, 56, and 58. Each possibility represents a separate embodiment of the invention.

In additional embodiments, the present invention provides a method of inducing cartilage repair or treating a degenerative joint disease, particularly osteoarthritis comprising the step of administering to an individual in need thereof a pharmaceutical composition comprising at least one isolated FGF-18 polypeptide having an N-terminal truncation extending beyond the signal peptide and further having at least one additional modification in its polypeptide sequence, wherein the modification is selected from an amino acid deletion, an amino acid substitution and an amino acid insertion, for example an amino acid substitution in the retained N-terminus sequence, or a polynucleotide encoding same. In exemplary embodiments, the method comprises the administration of a therapeutically effective amount of a polypeptide having an amino acid sequence as set forth in SEQ ID NO: 67 or 69, or a polynucleotide having a nucleotide sequence as set forth in SEQ ID NO: 68 or 70. Each possibility represents a separate embodiment of the invention.

In yet other embodiments, the present invention provides a method of inducing primary chondrocyte differentiation, comprising the steps of:

a. isolating a population of primary chondrocytes to be differentiated; and b. exposing said chondrocytes to at least one isolated FGF-18 polypeptide having an N-terminal truncation extending beyond the signal peptide as disclosed herein.

In yet another aspect, the present invention provides methods for the use of an isolated FGF-18 polypeptide having an N-terminal truncation extending beyond the signal peptide as disclosed herein for inducing primary chondrocyte differentiation.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1. The amino acid sequence of human FGF-18 (SEQ ID NO:1) and recombinant mature form of FGF-18 (SEQ ID NO:2).

and FGF-18$^{\Delta 51L52I}$ (▲)) were added at increasing concentrations and bound ligands were detected by HRP-streptavidin.

Figure 13A:
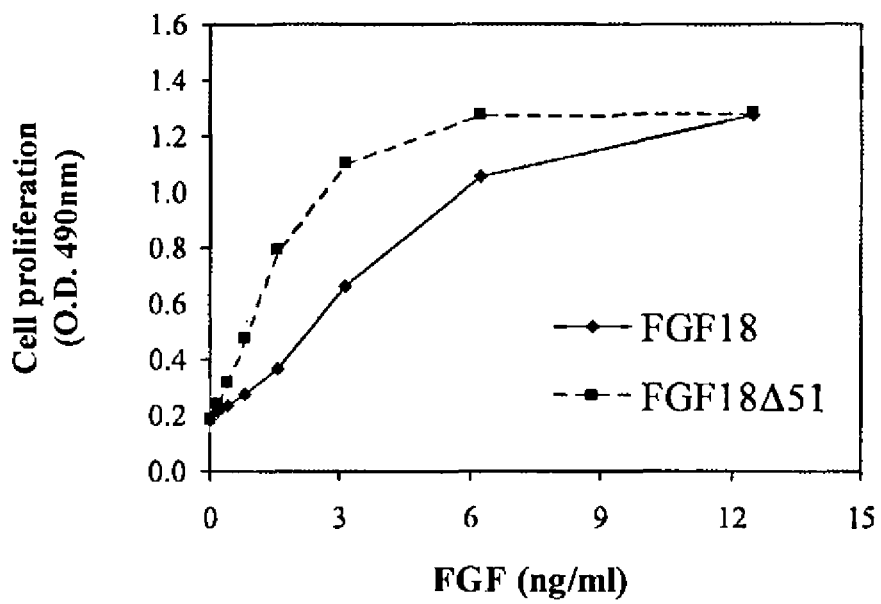
Figure 13B:
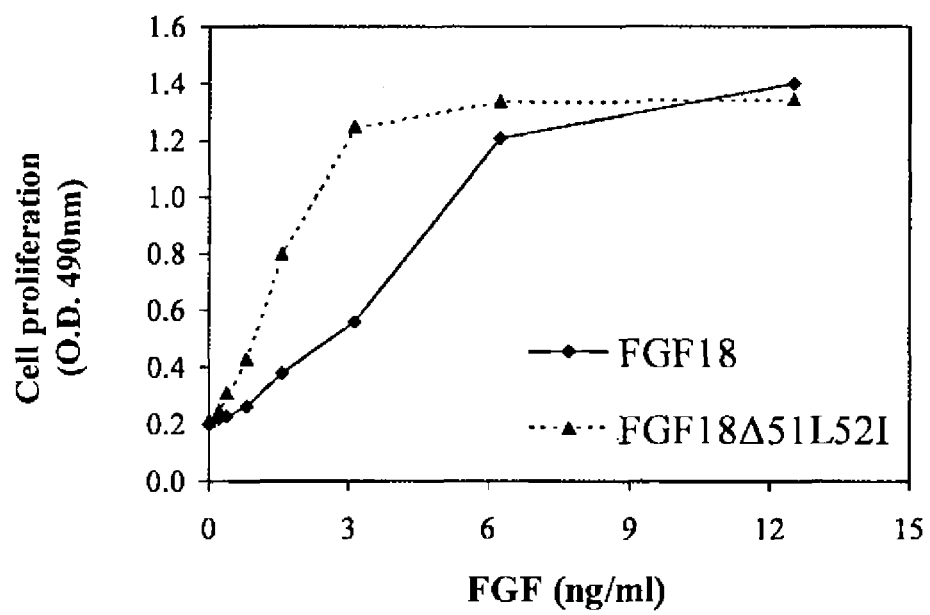

FIGS. 13A-13B. FGF-18$^{\Delta 51L52I}$ is a potent activator of FGFR3. (13A) FGF-18 wild type (♦) vs. FGF-18$^{\Delta 51}$ (■); and (13B) FGF-18 wild type (♦) vs. FGF-18$^{\Delta 51L52I}$ (▲). FDCP-FGFR3 cells were cultured with FGF-18, FGF-18$^{\Delta 51}$ and FGF-18$^{\Delta 51L52I}$ and cell proliferation was measured 2 days later by the XTT assay.

Figure 14:
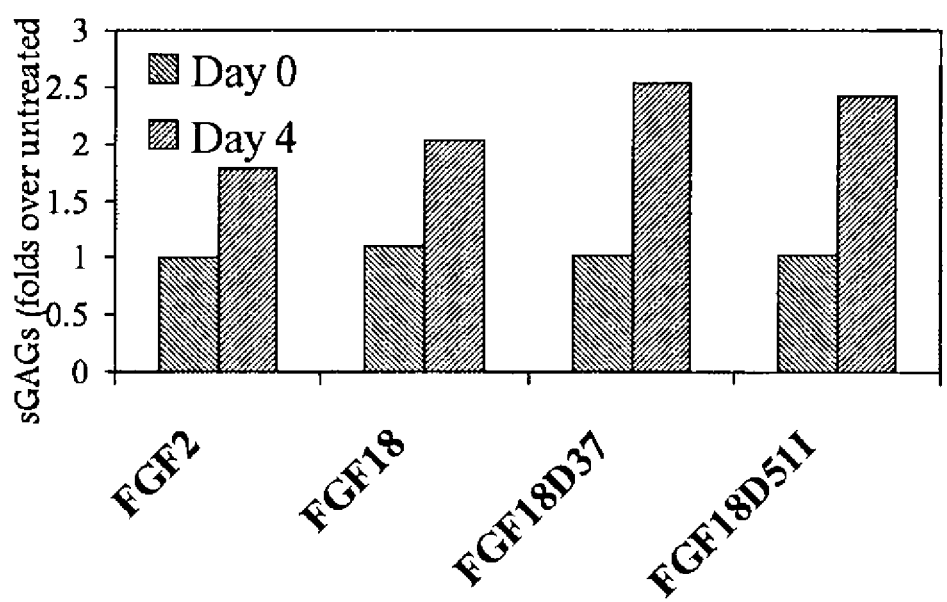

FIG. 14. FGF-induced GAG synthesis in chondrocytes. Cartilage taken from osteoarthritis patients was dissected and pre-incubated for 3 days in control medium (day 0) followed by 4 days in the presence of 50 ng/ml of the indicated FGFs. Cell supernatant was collected and levels of secreted glycosaminoglycans (GAGs) were determined.

DETAILED DESCRIPTION OF THE INVENTION

According to the principles of the present invention, it is now disclosed that isolated FGF-18 polypeptides having an N-terminal truncation which extends beyond the signal peptide show improved specificity for FGFR3. These variants show enhanced chondrogenic activity and are shown to afford differentiation of primary chondrocytes with no mitogenic activity.

The present invention provides an isolated FGF-18 polypeptide having an N-terminal truncation. The location of the N-terminal truncation, according to the principles of the present invention, extends beyond the signal peptide, i.e. an N-terminal truncation of the mature form of FGF-18. In one embodiment, the N-terminus retains between 0 and 28 amino acid residues at the N-terminus of the mature form extending beyond the core domain. When referring to an amino acid numbering which includes the signal peptide located at amino acids positions 1-27 (SEQ ID NO:1), the core domain starts at amino acid residue Leu57. The FGF-18 truncated polypeptides of the present invention include truncations of between 29 amino acids to 56 amino acids. These truncations therefore extend beyond the signal peptide, whereby the variants retain between 28 and 0 amino acid residues, respectively, at the N-terminus of the mature form extending beyond the core domain.

The amino acid sequences of the truncated polypeptides of the present invention are set forth herein below:

(FGF-18$^{\Delta 29}$):
SEQ ID NO: 3
MNVDFRIHVENQTRARDDVSRKQLRLYQLYSRTSGKHIQVLGRRISA
RGEDGDKYAQLLVETDTFGSQVRIKGKETEFYLCMNRKGKLVGKPDGTSK
ECVFIEKVLENNYTALMSAKYSGWYVGFTKKGRPRKGPKTRENQQDVHFM
KRYPKGQPELQKPFKYTTVTKRSRRIRPTHPA (FGF-18$^{\Delta 30}$):
SEQ ID NO: 5
MVDFRIHVENQTRARDDVSRKQLRLYQLYSRTSGKHIQVLGRRISAR
GEDGDKYAQLLVETDTFGSQVRIKGKETEFYLCMNRKGKLVGKPDGTSKE
CVFIEKVLENNYTALMSAKYSGWYVGFTKKGRPRKGPKTRENQQDVHFMK
RYPKGQPELQKPFKYTTVTKRSRRIRPTHPA (FGF-18$^{\Delta 31}$):
SEQ ID NO: 7
MDFRIHVENQTRARDDVSRKQLRLYQLYSRTSGKHIQVLGRRISARG
EDGDKYAQLLVETDTFGSQVRIKGKETEFYLCMNRKGKLVGKPDGTSKEC
VFIEKVLENNYTALMSAKYSGWYVGFTKKGRPRKGPKTRENQQDVHFMKR
YPKGQPELQKPFKYTTVTKRSRRIRPTHPA (FGF-18$^{\Delta 32}$):
SEQ ID NO: 9
MFRIHVENQTRARDDVSRKQLRLYQLYSRTSGKHIQVLGRRISARGE
DGDKYAQLLVETDTFGSQVRIKGKETEFYLCMNRKGKLVGKPDGTSKECV
FIEKVLENNYTALMSAKYSGWYVGFTKKGRPRKGPKTRENQQDVHFMKRY
PKGQPELQKPFKYTTVTKRSRRIRPTHPA (FGF-18$^{\Delta 33}$):
SEQ ID NO: 11
MRIHVENQTRARDDVSRKQLRLYQLYSRTSGKHIQVLGRRISARGED
GDKYAQLLVETDTFGSQVRIKGKETEFYLCMNRKGKLVGKPDGTSKECVF
IEKVLENNYTALMSAKYSGWYVGFTKKGRPRKGPKTRENQQDVHFMKRYP
KGQPELQKPFKYTTVTKRSRRIRPTHPA (FGF-18$^{\Delta 34}$):
SEQ ID NO: 13
MIHVENQTRARDDVSRKQLRLYQLYSRTSGKHIQVLGRRISARGEDG
DKYAQLLVETDTFGSQVRIKGKETEFYLCMNRKGKLVGKPDGTSKECVFI
EKVLENNYTALMSAKYSGWYVGFTKKGRPRKGPKTRENQQDVHFMKRYPK
GQPELQKPFKYTTVTKRSRRIRPTHPA (FGF-18$^{\Delta 35}$):
SEQ ID NO: 15
MHVENQTRARDDVSRKQLRLYQLYSRTSGKHIQVLGRRISARGEDG
DKYAQLLVETDTFGSQVRIKGKETEFYLCMNRKGKLVGKPDGTSKECVFI
EKVLENNYTALMSAKYSGWYVGFTKKGRPRKGPKTRENQQDVHFMKRYPK
GQPELQKPFKYTTVTKRSRRIRPTHPA (FGF-18$^{\Delta 36}$):
SEQ ID NO: 17
MVENQTRARDDVSRKQLRLYQLYSRTSGKHIQVLGRRISARGEDGD
KYAQLLVETDTFGSQVRIKGKETEFYLCMNRKGKLVGKPDGTSKECVFIE
KVLENNYTALMSAKYSGWYVGFTKKGRPRKGPKTRENQQDVHFMKRYPKG
QPELQKPFKYTTVTKRSRRIRPTHPA (FGF-18$^{\Delta 37}$):
SEQ ID NO: 19
MENQTRARDDVSRKQLRLYQLYSRTSGKHIQVLGRRISARGEDGDK
YAQLLVETDTFGSQVRIKGKETEFYLCMNRKGKLVGKPDGTSKECVFIEK
VLENNYTALMSAKYSGWYVGFTKKGRPRKGPKTRENQQDVHFMKRYPKGQ
PELQKPFKYTTVTKRSRRIRPTHPA (FGF-18$^{\Delta 38}$):
SEQ ID NO: 21
MNQTRARDDVSRKQLRLYQLYSRTSGKHIQVLGRRISARGEDGDKY
AQLLVETDTFGSQVRIKGKETEFYLCMNRKGKLVGKPDGTSKECVFIEKV
LENNYTALMSAKYSGWYVGFTKKGRPRKGPKTRENQQDVHFMKRYPKGQP
ELQKPFKYTTVTKRSRRIRPTHPA (FGF-18$^{\Delta 39}$):
SEQ ID NO: 23
MQTRARDDVSRKQLRLYQLYSRTSGKHIQVLGRRISARGEDGDKYA
QLLVETDTFGSQVRIKGKETEFYLCMNRKGKLVGKPDGTSKECVFIEKVL

ENNYTALMSAKYSGWYVGFTKKGRPRKGPKTRENQQDVHFMKRYPKGQPE
LQKPFKYTTVTKRSRRIRPTHPA (FGF-18$^{\Delta 40}$):
SEQ ID NO: 25
MTRARDDVSRKQLRLYQLYSRTSGKHIQVLGRRISARGEDGDKYAQ
LLVETDTFGSQVRIKGKETEFYLCMNRKGKLVGKPDGTSKECVFIEKVLE
NNYTALMSAKYSGWYVGFTKKGRPRKGPKTRENQQDVHFMKRYPKGQPEL
QKPFKYTTVTKRSRRIRPTHPA (FGF-18$^{\Delta 41}$):
SEQ ID NO: 27
MRARDDVSRKQLRLYQLYSRTSGKHIQVLGRRISARGEDGDKYAQLL
VETDTFGSQVRIKGKETEFYLCMNRKGKLVGKPDGTSKECVFIEKVLENN
YTALMSAKYSGWYVGFTKKGRPRKGPKTRENQQDVHFMKRYPKGQPELQK
PFKYTTVTKRSRRIRPTHPA (FGF-18$^{\Delta 42}$):
SEQ ID NO: 29
MARDDVSRKQLRLYQLYSRTSGKHIQVLGRRISARGEDGDKYAQLLV
ETDTFGSQVRIKGKETEFYLCMNRKGKLVGKPDGTSKECVFIEKVLENNY
TALMSAKYSGWYVGFTKKGRPRKGPKTRENQQDVHFMKRYPKGQPELQKP
FKYTTVTKRSRRIRPTHPA (FGF-18$^{\Delta 43}$):
SEQ ID NO: 31
MRDDVSRKQLRLYQLYSRTSGKHIQVLGRRISARGEDGDKYAQLLVE
TDTFGSQVRIKGKETEFYLCMNRKGKLVGKPDGTSKECVFIEKVLENNYT
ALMSAKYSGWYVGFTKKGRPRKGPKTRENQQDVHFMKRYPKGQPELQKPF
KYTTVTKRSRRIRPTHPA (FGF-18$^{\Delta 44}$):
SEQ ID NO: 33
MDDVSRKQLRLYQLYSRTSGKHIQVLGRRISARGEDGDKYAQLLVET
DTFGSQVRIKGKETEFYLCMNRKGKLVGKPDGTSKECVFIEKVLENNYTA
LMSAKYSGWYVGFTKKGRPRKGPKTRENQQDVHFMKRYPKGQPELQKPFK
YTTVTKRSRRIRPTHPA (FGF-18$^{\Delta 45}$):
SEQ ID NO: 35
MDVSRKQLRLYQLYSRTSGKHIQVLGRRISARGEDGDKYAQLLVETD
TFGSQVRIKGKETEFYLCMNRKGKLVGKPDGTSKECVFIEKVLENNYTAL
MSAKYSGWYVGFTKKGRPRKGPKTRENQQDVHFMKRYPKGQPELQKPFKY
TTVTKRSRRIRPTHPA (FGF-18$^{\Delta 46}$):
SEQ ID NO: 37
MVSRKQLRLYQLYSRTSGKHIQVLGRRISARGEDGDKYAQLLVETDT
FGSQVRIKGKETEFYLCMNRKGKLVGKPDGTSKECVFIEKVLENNYTALM
SAKYSGWYVGFTKKGRPRKGPKTRENQQDVHFMKRYPKGQPELQKPFKYT
TVTKRSRRIRPTHPA (FGF-18$^{\Delta 47}$):
SEQ ID NO: 39
MSRKQLRLYQLYSRTSGKHIQVLGRRISARGEDGDKYAQLLVETDTF
GSQVRIKGKETEFYLCMNRKGKLVGKPDGTSKECVFIEKVLENNYTALMS
AKYSGWYVGFTKKGRPRKGPKTRENQQDVHFMKRYPKGQPELQKPFKYTT
VTKRSRRIRPTHPA (FGF-18$^{\Delta 48}$):
SEQ ID NO: 41
MRKQLRLYQLYSRTSGKHIQVLGRRISARGEDGDKYAQLLVETDTFG
SQVRIKGKETEFYLCMNRKGKLVGKPDGTSKECVFIEKVLENNYTALMSA
KYSGWYVGFTKKGRPRKGPKTRENQQDVHFMKRYPKGQPELQKPFKYTTV
TKRSRRIRPTHPA (FGF-18$^{\Delta 49}$):
SEQ ID NO: 43
MKQLRLYQLYSRTSGKHIQVLGRRISARGEDGDKYAQLLVETDTFGS
QVRIKGKETEFYLCMNRKGKLVGKPDGTSKECVFIEKVLENNYTALMSAK
YSGWYVGFTKKGRPRKGPKTRENQQDVHFMKRYPKGQPELQKPFKYTTVT
KRSRRIRPTHPA (FGF-18$^{\Delta 50}$):
SEQ ID NO: 45
MQLRLYQLYSRTSGKHIQVLGRRISARGEDGDKYAQLLVETDTFGSQ
VRIKGKETEFYLCMNRKGKLVGKPDGTSKECVFIEKVLENNYTALMSAKY
SGWYVGFTKKGRPRKGPKTRENQQDVHFMKRYPKGQPELQKPFKYTTVTK
RSRRIRPTHPA (FGF-18$^{\Delta 51}$):
SEQ ID NO: 47
MLRLYQLYSRTSGKHIQVLGRRISARGEDGDKYAQLLVETDTFGSQV
RIKGKETEFYLCMNRKGKLVGKPDGTSKECVFIEKVLENNYTALMSAKYS
GWYVGFTKKGRPRKGPKTRENQQDVHFMKRYPKGQPELQKPFKYTTVTKR
SRRIRPTHPA (FGF-18$^{\Delta 52}$):
SEQ ID NO: 49
MRLYQLYSRTSGKHIQVLGRRISARGEDGDKYAQLLVETDTFGSQVR
IKGKETEFYLCMNRKGKLVGKPDGTSKECVFIEKVLENNYTALMSAKYSG
WYVGFTKKGRPRKGPKTRENQQDVHFMKRYPKGQPELQKPFKYTTVTKRS
RRIRPTHPA (FGF-18$^{\Delta 53}$):
SEQ ID NO: 51
MLYQLYSRTSGKHIQVLGRRISARGEDGDKYAQLLVETDTFGSQVRI
KGKETEFYLCMNRKGKLVGKPDGTSKECVFIEKVLENNYTALMSAKYSGW
YVGFTKKGRPRKGPKTRENQQDVHFMKRYPKGQPELQKPFKYTTVTKRSR
RIRPTHPA (FGF-18$^{\Delta 54}$):
SEQ ID NO: 53
MYQLYSRTSGKHIQVLGRRISARGEDGDKYAQLLVETDTFGSQVRIK
GKETEFYLCMNRKGKLVGKPDGTSKECVFIEKVLENNYTALMSAKYSGWY
VGFTKKGRPRKGPKTRENQQDVHFMKRYPKGQPELQKPFKYTTVTKRSRR
IRPTHPA (FGF-18$^{\Delta 55}$):
SEQ ID NO: 55
MQLYSRTSGKHIQVLGRRISARGEDGDKYAQLLVETDTFGSQVRIKG
KETEFYLCMNRKGKLVGKPDGTSKECVFIEKVLENNYTALMSAKYSGWYV

GFTKKGRPRKGPKTRENQQDVHFMKRYPKGQPELQKPFKYTTVTKRSRRI

RPTHPA (FGF-18^{Δ56}):

SEQ ID NO: 57
MLYSRTSGKHIQVLGRRISARGEDGDKYAQLLVETDTFGSQVRIKGK

ETEFYLCMNRKGKLVGKPDGTSKECVFIEKVLENNYTALMSAKYSGWYVG

FTKKGRPRKGPKTRENQQDVHFMKRYPKGQPELQKPFKYTTVTKRSRRIR

PTHPA

Currently preferred are the N-terminal truncated FGF-18 polypeptides identified by SEQ ID NOS: 11, 19, 35 and 47. Each possibility represents a separate embodiment of the invention.

The present invention further provides an isolated FGF-18 polypeptide having an N-terminal truncation and further having at least one additional modification (e.g. an amino acid deletion, an amino acid substitution or an amino acid insertion), preferably in the retained N-terminus. Without being bound by any theory or mechanism of action, the at least one additional modification provides enhanced stability, solubility or yield of the polypeptide. In some embodiments, the isolated FGF-18 polypeptide has a 50 amino acid N-terminal truncation with Gln51 being replaced by a Met residue and a replacement of the penultimate leucine (L52) with an amino acid other than leucine. In particular embodiments, the at least one modification is the conservative replacement of the penultimate leucine (L52) with another non-charged, hydrophobic amino acid, for example isoleucine, valine or methionine. Each possibility represents a separate embodiment of the invention.

The amino acid sequences of the polypeptides are set forth herein below:

(FGF-18^{Δ51L52X}):

SEQ ID NO: 67
MXRLYQLYSRTSGKHIQVLGRRISARGEDGDKYAQLLVETDTFGSQV

RIKGKETEFYLCMNRKGKLVGKPDGTSKECVFIEKVLENNYTALMSAKYS

GWYVGFTKKGRPRKGPKTRENQQDVHFMKRYPKGQPELQKPFKYTTVTKR

SRRIRPTHPA

X is an amino acid residue other than leucine, for example isoleucine, valine or methionine.

(FGF-18^{Δ51L52I}):

SEQ ID NO: 69
MIRLYQLYSRTSGKHIQVLGRRISARGEDGDKYAQLLVETDTFGSQV

RIKGKETEFYLCMNRKGKLVGKPDGTSKECVFIEKVLENNYTALMSAKYS

GWYVGFTKKGRPRKGPKTRENQQDVHFMKRYPKGQPELQKPFKYTTVTKR

SRRIRPTHPA

According to the principles of the present invention, the polypeptides of the present invention have increased receptor selectivity when compared to the isolated wild-type FGF-18 polypeptide by a gain of activity or loss of activity by at least a factor of two toward at least one receptor subtype but not toward all FGFR subtypes. It has now been disclosed for the first time that these truncated variants specifically activate FGFR3 while essentially eliminating the activation of other receptor subtypes including, in particular FGFR1 and FGFR2.

As used herein and in the claims the term "FGFR" denotes a receptor specific for FGF molecule(s), which is necessary for transducing the signal, exerted by FGF to the cell interior, typically comprising an extracellular ligand-binding domain, a single transmembrane helix, and a cytoplasmic domain that contains a tyrosine kinase activity. The term "FGFR" includes various isotypes of the receptors including soluble versions comprising the extracellular domain and lacking the transmembrane and kinase domains. As used herein and in the claims the term "an isolated FGF-18 polypeptide having increased receptor selectivity" denotes an isolated FGF-18 polypeptide molecule, having either enhanced or reduced biological activity toward at least one but not all FGFR, compared to the corresponding wild type FGF-18. The biological activity toward at least one receptor, but not all FGF receptors, is reduced or increased by a factor of at least 2. In some embodiments, the biological activity toward at least one receptor, but not all FGF receptors, is reduced or increased by a factor of at least 4, at least 5, at least 7 or at least 10. Biological activity, according to the principles of the present invention, can be measured by methods known in the art. In some embodiments, biological activity is measured by a cell proliferation or cell differentiation assay or alternatively by substrate phosphorylation.

As contemplated herein, the variants of the present invention afford differentiation of primary chondrocytes. The differentiation can be determined as is known in the art by morphological and/or phenotypic changes and/or by biochemical or molecular changes. The variants of the present invention essentially do not show mitogenic activity. "Mitogenic activity" as used herein refers to the ability to induce an increase in the number of cells.

The N-terminal truncated variants of the present invention can be prepared by any manner known in the art. Exemplary method for producing the variants is through recombinant DNA technologies, for example by Polymerase Chain Reaction (PCR) using specific primers for each of the truncated forms as disclosed herein. The PCR fragments may be purified on an agarose gel and the purified DNA fragment may be cloned into an expression vector and transfected into host cells. The host cells may be cultured and the protein harvested according to methods known in the art. As used herein, the term "polymerase chain reaction" ("PCR") refers to the methods of amplifying nucleic acids, as disclosed in e.g. U.S. Pat. Nos. 4,683,195; 4,683,202 and 4,965,188 hereby incorporated by reference.

According to the principles of the present invention the N-terminal truncated variants of the present invention may further comprise at least one modification including, but not limited to, a substitution of at least one amino acid, preferably in the retained N-terminus. The term "at least one modification" as used herein refers to an amino acid sequence that is altered by one or more amino acids including an amino acid deletion, an amino acid substitution or an amino acid insertion. An amino acid substitution is selected from a conservative substitution or a non-conservative substitution. "Conservative" substitutions refer to replacements wherein the amino acid that replaces the naturally occurring amino acid has similar structural or chemical properties, e.g., replacement of leucine with any one of isoleucine, valine or methionine. Each possibility represents a separate embodiment of the invention. Of these, leucine and isoleucine are the most closely related amino acids and are therefore considered interchangeable by those of skill in the art. "Non-conservative" substitutions refer to replacements wherein the amino acid that replaces the naturally occurring amino acid has different structural or chemical properties, e.g. replacement of leucine with histidine. Analogous minor modification may also include amino acid deletions or insertions, or both.

The present invention further provides the isolated polynucleotides encoding the N-terminal truncated variants of the present invention and a vector and a host cell comprising the polynucleotides. The polynucleotides encoding the variants of the present invention are identified by SEQ ID NOS: 4, 6, 8, 10, 12, 14, 16, 18, 20, 22, 24, 26, 28, 30, 32, 34, 36, 38, 40, 42, 44, 46, 48, 50, 52, 54, 56, and 58. Each possibility represents a separate embodiment of the invention. Currently preferred are polynucleotides identified by SEQ ID NOS: 12, 20, 36 and 48. Each possibility represents a separate embodiment of the invention. In further embodiments, the present invention provides isolated polynucleotides encoding the N-terminal truncated variants which further comprise at least one modification as defined herein and a vector and a host cell comprising the polynucleotides. The polynucleotides are identified by SEQ ID NO: 68 or 70. Each possibility represents a separate embodiment of the present invention. Selected sequences are set forth herein below:

encoding FGF-18$^{\Delta 37}$:
SEQ ID NO: 20
atggagaaccagacgcgggctcgggacgatgtgagccgtaagcagctgcg gctgtaccagctctacagccggaccagtgggaaacacatccaggtcctgg gccgcaggatcagtgcccgcggcgaggatggggacaagtatgcccagctc ctagtggagacagacaccttcggtagtcaagtccggatcaagggcaagga gacggaattctacctgtgcatgaaccgcaaaggcaagctcgtggggaagc ccgatggcaccagcaaggagtgtgtgttcatcgagaaggttctggagaac aactacacggccctgatgtcggctaagtactccggctggtacgtgggctt caccaagaaggggcggccgcggaagggccccaagacccgggagaaccagc aggacgtgcatttcatgaagcgctaccccaaggggcagccggagcttcag aagcccttcaagtacacgacggtgaccaagaggtcccgtcggatccggcc cacacaccctgcctag encoding FGF-18$^{\Delta 45}$:
SEQ ID NO: 36
atggatgtgagccgtaagcagctgcggctgtaccagctctacagccggac cagtgggaaacacatccaggtcctgggccgcaggatcagtgcccgcggcg aggatggggacaagtatgcccagctcctagtggagacagacaccttcggt agtcaagtccggatcaagggcaaggagacggaattctacctgtgcatgaa ccgcaaaggcaagctcgtggggaagcccgatggcaccagcaaggagtgtg tgttcatcgagaaggttctggagaacaactacacggccctgatgtcggct aagtactccggctggtacgtgggcttcaccaagaaggggcggccgcggaa gggccccaagacccgggagaaccagcaggacgtgcatttcatgaagcgct accccaaggggcagccggagcttcagaagcccttcaagtacacgacggtg accaagaggtcccgtcggatccggcccacacaccctgcctag encoding FGF-18$^{\Delta 51}$:
SEQ ID NO: 48
atgctgcggctgtaccagctctacagccggaccagtgggaaacacatcca ggtcctgggccgcaggatcagtgcccgcggcgaggatggggacaagtatg cccagctcctagtggagacagacaccttcggtagtcaagtccggatcaag ggcaaggagacggaattctacctgtgcatgaaccgcaaaggcaagctcgt ggggaagcccgatggcaccagcaaggagtgtgtgttcatcgagaaggttc tggagaacaactacacggccctgatgtcggctaagtactccggctggtac gtgggcttcaccaagaaggggcggccgcggaagggccccaagacccggga gaaccagcaggacgtgcatttcatgaagcgctaccccaaggggcagccgg agcttcagaagcccttcaagtacacgacggtgaccaagaggtcccgtcgg atccggcccacacaccctgcctag encoding (FGF-18$^{\Delta 51L52X}$)
SEQ ID NO: 68
ATGNNNCGGCTGTACCAGCTCTACAGCCGGACCAGTGGGAAACA

CATCCAGGTCCTGGGCCGCAGGATCAGTGCCCGCGGCGAGGATGGGG

ACAAGTATGCCCAGCTCCTAGTGGAGACAGACACCTTCGGTAGTCAAGT

CCGGATCAAGGGCAAGGAGACGGAATTCTACCTGTGCATGAACCGCAAA

GGCAAGCTCGTGGGGAAGCCCGATGGCACCAGCAAGGAGTGTGTGTTC

ATCGAGAAGGTTCTGGAGAACAACTACACGGCCCTGATGTCGGCTAAGT

ACTCCGGCTGGTACGTGGGCTTCACCAAGAAGGGGCGGCCGCGGAAGG

GCCCCAAGACCCGGGAGAACCAGCAGGACGTGCATTTCATGAAGCGCT

ACCCCAAGGGGCAGCCGGAGCTTCAGAAGCCCTTCAAGTACACGACGG

TGACCAAGAGGTCCCGTCGGATCAGGCCCACACACCCTGCCTAG

NNN is a codon coding for an amino acid other than leucine, for example isoleucine, valine or methionine.

encoding (FGF-18$^{\Delta 51L52I}$)
SEQ ID NO: 70
ATGATACGGCTGTACCAGCTCTACAGCCGGACCAGTGGGAAACA

CATCCAGGTCCTGGGCCGCAGGATCAGTGCCCGCGGCGAGGATGGGG

ACAAGTATGCCCAGCTCCTAGTGGAGACAGACACCTTCGGTAGTCAAGT

CCGGATCAAGGGCAAGGAGACGGAATTCTACCTGTGCATGAACCGCAAA

GGCAAGCTCGTGGGGAAGCCCGATGGCACCAGCAAGGAGTGTGTGTTC

ATCGAGAAGGTTCTGGAGAACAACTACACGGCCCTGATGTCGGCTAAGT

ACTCCGGCTGGTACGTGGGCTTCACCAAGAAGGGGCGGCCGCGGAAGG

GCCCCAAGACCCGGGAGAACCAGCAGGACGTGCATTTCATGAAGCGCT

ACCCCAAGGGGCAGCCGGAGCTTCAGAAGCCCTTCAAGTACACGACGG

TGACCAAGAGGTCCCGTCGGATCAGGCCCACACACCCTGCCTAG

Within the scope of the present invention are nucleic acid molecules containing polynucleotide sequences having at least 90% sequence identity, preferably about 95%, and more preferably about 97% identity to the above encoding nucleotide sequences as understood by those of skill in the art.

The invention also provides isolated nucleic acid molecules that hybridize under high stringency conditions to polynucleotides having SEQ ID NOS: 4, 6, 8, 10, 12, 14, 16, 18, 20, 22, 24, 26, 28, 30, 32, 34, 36, 38, 40, 42, 44, 46, 48, 50, 52, 54, 56, 58, 68 and 70 or the complement thereof. As used herein, highly stringent conditions are those which are tolerant of up to about 5-20% sequence divergence, preferably about 5-10%. Without limitation, examples of highly stringent (−10° C. below the calculated Tm of the hybrid) conditions use a wash solution of 0.1×SSC (standard saline citrate) and 0.5% SDS at the appropriate Ti below the calculated Tm of the hybrid. The ultimate stringency of the conditions is primarily due to the wash conditions, particularly if the hybridization conditions used are those which allow less stable hybrids to form along with stable hybrids. The wash conditions at higher stringency remove the less stable hybrids. A common hybridization condition that can be used with the highly stringent to moderately stringent wash conditions described above may be performed by hybridizing in a solution of 6×SSC (or 6×SSPE), 5×Denhardt's reagent, 0.5% SDS, 100 µg/ml denatured, fragmented salmon sperm DNA at an appropriate incubation temperature Ti. See generally Sambrook et al. (Sambrook et al., Molecular Cloning: A Laboratory Manual, $2^{nd}$ Ed., 1989, Cold Spring Harbor Press) for suitable high stringency conditions.

Stringency conditions are a function of the temperature used in the hybridization experiment and washes, the molarity of the monovalent cations in the hybridization solution and in the wash solution(s) and the percentage of formamide in the hybridization solution. In general, sensitivity by hybridization with a probe is affected by the amount and specific activity of the probe, the amount of the target nucleic acid, the detectability of the label, the rate of hybridization and hybridization duration. The hybridization rate is maximized at a Ti (incubation temperature) of 20-25° C. below Tm for DNA:DNA hybrids and 10-15° C. below Tm for DNA:RNA hybrids. It is also maximized by an ionic strength of about 1.5M $Na^+$. The rate is directly proportional to duplex length and inversely proportional to the degree of mismatching. Specificity in hybridization, however, is a function of the difference in stability between the desired hybrid and "background" hybrids. Hybrid stability is a function of duplex length, base composition, ionic strength, mismatching, and destabilizing agents (if any).

The Tm of a perfect hybrid may be estimated for DNA:DNA hybrids using the equation of Meinkoth et al. (Anal. Biochem. 1984, Vol. 138(2), p. 267), as $$Tm=81.5° C.+16.6(\log M)+0.41(\% GC)-0.61(\% \text{form})-500/L$$

and for DNA:RNA hybrids, as $$Tm=79.8° C.+18.5(\log M)+0.58(\% GC)-11.8(\% GC)^2-0.56(\% \text{form})-820/L$$

where

M, molarity of monovalent cations, 0.01-0.4 M NaCl,

% GC, percentage of G and C nucleotides in DNA, 30%-75%,

% form, percentage formamide in hybridization solution, and

L, length hybrid in base pairs.

Tm is reduced by 0.5-1.5° C. (an average of 1° C. can be used for ease of calculation) for each 1% mismatching. The Tm may also be determined experimentally.

Filter hybridization is typically carried out at 68° C., and at high ionic strength (e.g., 5-6×SSC), which is non-stringent, and followed by one or more washes of increasing stringency, the last one being of the ultimately desired high stringency. The equations for Tm can be used to estimate the appropriate Ti for the final wash, or the Tm of the perfect duplex can be determined experimentally and Ti then adjusted accordingly.

The present invention also relates to a vector comprising the nucleic acid molecule of the present invention. The vector of the present invention may be, e.g., a plasmid, cosmid, virus, bacteriophage or another vector used e.g. conventionally in genetic engineering, and may comprise further genes such as marker genes which allow for the selection of said vector in a suitable host cell and under suitable conditions.

The term "expression vector" and "recombinant expression vector" as used herein refers to a recombinant DNA molecule containing a desired coding sequence and appropriate nucleic acid sequences necessary for the expression of the operably linked coding sequence in a particular host organism. The expression vector may comprise sequences encoding heterologous domains including, but not limited to, protein detection, purification or cleavage sequences that may be fused at the N- or C-terminus to the desired coding sequence, to yield a fusion protein. The present invention encompasses expression vectors that are integrated into host cell genomes, as well as episomal vectors.

Within the scope of the present invention is the combination of the FGF-18 variants with at least one other bioactive agent. As used herein and in the claims a "bioactive agent" refers to a pharmaceutically active compound which provides enhanced effect when mixed with the variants of the present invention. This includes, but is not limited to, peptides and peptide analogs, peptidomimetics, oligopeptides, proteins, apoproteins, glycoproteins, antigens and antibodies or antibody fragments thereto, receptors and other membrane proteins, aptamers, enzymes, coenzymes, enzyme inhibitors, amino acids and their derivatives, hormones, lipids, phospholipids, liposomes; toxins; tyrosine kinase inhibitors, photoreactive agents, antibiotics; analgesics and anti-inflammatory substances; antimicrobial agents; antihypertensive agents; antiviral agents; antihistamines; anti-cancer drugs including chemotherapeutic agents; tranquilizers; neuroprotective agents; antispasmodics; anti-Parkinson agents, vitamins, nucleotides, oligonucleotides, polynucleotides, and their biologically functional analogs and derivatives, plasmids, cosmids, artificial chromosomes, other nucleic acid vectors, antisense polynucleotides including those substantially complementary to at least one endogenous nucleic acid, promoters, enhancers, inhibitors, other ligands for regulating gene transcription and translation and the like. Each possibility represents a separate embodiment of the invention.

In particular embodiments the present invention provides the combination of the FGF-18 variants with at least one other bioactive agent, wherein the at least one other active agent is a carboxylated polysaccharide. In currently preferred embodiments, the carboxylated polysaccharide is hyaluronic acid (HA) and its derivatives including, but not limited to, the partial esters of hyaluronic acid with aliphatic, arylphatic, heterocyclic and cycloaliphatic alcohols. Suitable molecular weights of hyaluronic acid and its partial esters range from about $10^4$ Daltons to about three million ($3×10^6$) Daltons.

Disclosed herein for the first time is a mixture of at least one FGF-18 variant of the present invention and at least one natriuretic peptide which provides a synergistic effect. The terms "synergistic", "cooperative" and "super-additive" and their various grammatical variations as used herein refer to e.g. an observed effect which is higher in the presence of the components together than the sum of the individual effects of each component when administered separately. In one embodiment, the observed combined effect of the FGF-18 variant and the natriuretic peptide is significantly higher than the sum of the individual effects. The term significant means that the observed $p<0.05$. Currently preferred is the admixture of at least one N-terminal truncated variant of FGF-18 with C-type natriuretic peptide (CNP). CNP is a known regulator of longitudinal bone growth. Genetic ablation of CNP or its signaling pathway components results in severe skeletal dysplasias caused by reduced chondrocyte proliferation and differentiation (Chusho et al., PNAS US, 2001, Vol. 98, p. 4016-; Miyazawa et al., 2002, Endocrinology, Vol. 143, p. 3604; Tamura et al., PNAS US, 2004, Vol. 101, p. 17300).

This phenotype is remarkably similar to that caused by mutant FGFR3, the causative agent of achondroplasia. These findings led, in recent years, to intense investigation of the mechanism of action of CNP and its interaction with the FGF signaling pathway in chondrocytes. FGFs exert their effect mainly through the MAPK, STAT and PI3K pathways. Krejci et al. (Journal of Cell Science, 2005, Vol. 118, p. 5089) demonstrated that CNP counteracts FGF's action through MAPK inhibition. Yet, in another study, it has been shown that STAT in not affected by CNP (Ozasa et al., Bone, 2005, Vol. 36, p. 1056). Modulation of PI3K by CNP is currently not well characterized. In addition, CNP increases extracellular matrix mass independent of its interference with FGF signaling (Krejci et al., Journal of Cell Science, 2005, Vol. 118, p. 5089). Thus, CNP may utilize both direct and indirect ways to antagonize FGF signaling in chondrocytes. CNP is known as a chondrogenic factor and is usually considered to be an antagonist to FGFs. It is believed to operate by counteracting FGFs. Unexpectedly, it is now disclosed for the first time that the FGF variants of the present invention when admixed with CNP provide a synergistic effect on FGFR3. According to the principles of the present invention, the terms admixture or combination of FGF-18 variants and CNP exclude covalent conjugate or chimeric recombinant of the two components.

The present invention further provides pharmaceutical compositions comprising at least one polypeptide or polynucleotide encoding same and at least one diluent or carrier. The carrier may be any of those conventionally used and is limited only by chemical-physical considerations, such as solubility and lack of reactivity with the active ingredient of the invention, and by the route of administration. The choice of carrier will be determined by the particular method used to administer the pharmaceutical composition. Some non-limiting examples of suitable carriers include lactose, glucose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, cellulose derivatives (e.g. methylcellulose), water, calcium carbonate, various types of starch, vegetable oils and polyethylene glycols. Each possibility represents a separate embodiment of the invention. The compositions may further comprises lubricating agents such as talc, magnesium stearate, and mineral oil; wetting agents, surfactants, emulsifying and suspending agents; preserving agents such as methyl- and propylhydroxybenzoates; sweetening agents; colorants, buffering agents (e.g., acetates, citrates or phosphates), disintegrating agents, moistening agents, antibacterial agents, antioxidants (e.g., ascorbic acid or sodium bisulfite), chelating agents (e.g., ethylenediaminetetraacetic acid), and agents for the adjustment of tonicity such as sodium chloride. Each possibility represents a separate embodiment of the invention. Other pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerin, propylene glycol or other synthetic solvents. Each possibility represents a separate embodiment of the invention. Water is a preferred carrier when the pharmaceutical composition is administered intravenously. Saline solutions and aqueous dextrose and glycerol solutions can also be employed as liquid carriers, particularly for injectable solutions. Other compounds which are known to increase the resistance to proteolitic degradation might also be added.

The pharmaceutical compositions of the present invention may be manufactured by processes well known in the art, e.g., by means of conventional mixing, dissolving, granulating, grinding, pulverizing, dragee-making, levigating, emulsifying, encapsulating, entrapping or lyophilizing processes. Each possibility represents a separate embodiment of the invention.

The pharmaceutical compositions of this invention may be administered by any suitable means, such as orally, intranasally, subcutaneously, intramuscularly, intravenously, intra-arterially, or parenterally. Each possibility represents a separate embodiment of the invention. Ordinarily, intra-articular administration is currently preferred. The dosage will be prescribed according to common regimes in the art, while taking into consideration variables such as: weight, age, extent of damage etc.

The N-terminal truncated FGF-18 ligands with increased specificity for FGFR3 are useful in the treatment of various pathological conditions of the cartilage and are capable of specifically targeting the cartilage for inducing cartilage repair. Thus, the compositions of the present invention are suitable for treating any cartilage defect or disorder. The terms "cartilage defect" or "cartilage disorder" as used herein refer to cartilage that has been damaged by disease, injury or trauma including indications such as, but not limited to, rheumatoid arthritis, osteoarthritis and joint injuries. Each possibility represents a separate embodiment. The treatment is suitable for an acute injury as well as for a chronic condition requiring prolonged treatment.

The N-terminal truncated FGF-18 ligands with increased specificity for FGFR3 are useful in the treatment of various skeletal disorders and in the treatment of degenerative joint diseases. An exemplary degenerative joint disease is osteoarthritis, a disease which involves the degradation of joints, including articular cartilage and subchondral bone.

The compositions of the present invention are suitable for treating a subject in need thereof, preferably a mammal, particularly a human.

FGF-18 variants activity is conveniently determined using biological assays performed in-vitro, ex-vivo and in vivo. The assays are used to demonstrate the activity elicited upon binding of an FGF-18 variant of the present invention to its receptors. The biological assays routinely used to test activities of variant FGFs include, but are not limited to, the following: binding of variant FGFs to cloned FGF receptors expressed on immortalized cell lines, thereby eliciting a biological response including cell proliferation or inhibition of cell proliferation; cell proliferation and differentiation in cell culture systems; phosphorylation assays; and enhancement of cartilage repair in animal models of cartilage disease and trauma.

The present invention further provides a method of inducing primary chondrocyte differentiation by exposing primary chondrocytes to at least one N-terminal truncated FGF-18 variant of the present invention to induce differentiation.

The principles of the invention are demonstrated by means of the following non-limiting examples.

EXAMPLES

Example 1

Preparation of FGF-18 Polynucleotide and Polypeptide Variants

The FGF-18 variants were prepared by standard PCR amplification and cloning into a pET9a expression vector. The vector has unique NdeI-BamHI restriction sites and the PCR-generated DNA fragments encompassing the coding region of a number of proteins and variants were produced having NdeI and BamHI sites at the 5' and 3' ends, respectively. The polynucleotide fragments encoding the proteins were ligated into digested pET9a and the plasmid was used to transform E. coli cells, such as BL21-DE3, using standard transformation protocols.

The primers used for construction of the variants are shown in Table 1, herein below.

TABLE 1

Forward and reverse primers used in preparation of the FGF-18 variants of the present invention.

| FGF-18 poly-peptide | POLY-NUCLEOTIDE ENCODING THE FGF-18 POLYPEPTIDE SEQ ID NO: | FORWARD PRIMER | Backward Primer |
|---|---|---|---|
| FGF-18$^{\Delta 31}$ | 8 | 5' GGAATTCCATATG GACTTCCGCATC CACG SEQ ID NO: 65 | SEQ ID NO: 61 |
| FGF-18$^{\Delta 33}$ | 12 | 5' GGAATTC CATATG CGCATCCACGTGGAGAAC SEQ ID NO: 66 | SEQ ID NO: 61 |
| FGF-18$^{\Delta 37}$ | 20 | 5' GGAATTC CATATG GAGAACCAGACGCGGGC SEQ ID NO: 60 | 5' ACGT GGATCC CTAGGCAGGG TGTGTGG SEQ ID NO: 61 |
| FGF-18$^{\Delta 45}$ | 36 | 5' GGAATTC CATATG GATGTGAGCCGTAAGCAG SEQ ID NO: 62 | SEQ ID NO: 61 |
| FGF-18$^{\Delta 51}$ | 48 | 5' GGAATTC CATATG CTGCGGCTGTACCAGCTC SEQ ID NO: 63 | SEQ ID NO: 61 |
| FGF-18 (recombinant wild type) | 59 | 5' GGAATTC CATATG GCCGAGGAGAACGTGG SEQ ID NO: 64 | SEQ ID NO: 61 |

A single colony was selected and grown overnight (ON) at 37° C. in 5 ml 2YT (8O g Trypton; 50 g yeast extract; 25 g NaCl for 5 Liters) supplemented with 200 μg/ml ampicillin. The next day, the culture was diluted 100 times. At O.D.600=0.6 0.1 mM IPTG was added and bacteria were further fermented over night. The bacterial suspension was centrifuged at 4000 rpm (4° C.) for 15 minutes, and the medium was discarded. The bacterial pellet was then suspended in 10 ml of 1×PBS+1 M NaCl buffer containing protease inhibitors, sonicated on ice, shaked over night at 4° C. and centrifuged at 10,000 rpm (4° C.) for 15 minutes. The protein supernatant was collected, filtered and diluted 5 times with 1×PBS. FGF polypeptides were purified on FPLC using a heparin Sepharose column (HiTrap™ Heparin, Amersham Pharmacia biotech) with a 0-2.5M NaCl (in PBS). The purified proteins were later stored at −70° C.

Example 2

FGF-18 Variant Binding to FGFR-Transfected FDCP Cell Lines

The FDCP cell line is a murine immortalized, interleukin 3 (IL-3)-dependent cell line of myelocytic bone marrow origin that does not express endogenous FGF Receptors (FGFR). Upon transfection with FGFR cDNA, the FDCP cell line exhibits a dose-dependent proliferative response to FGF that can replace the dependence on IL-3. FGFR transfected FDCP cells can therefore be used to screen variant FGFs for specific inhibitors, activators or for FGFR signaling. FDCP cells response to various ligands is quantitated by a cell proliferation assay with XTT reagent (Cell Proliferation Kit, Biological Industries Co.). The method is based on the capability of mitochondrial enzymes to reduce tetrazolium salts into a colorogenic compound, which can be quantitated and is indicative of cell viability.

Specifically, FDCP cells stably expressing FGFR4, FGFR3-IIIc, FGFR2IIIc or FGFR1IIIc were grown in "full medium" (Iscove's Medium containing 2 ml glutamine, 10% FCS, 100 μg/ml penicillin, 100 μg/ml streptomycin) supplemented with 5 μg/ml heparin and 10 ng/ml FGF. Cells were split every 3 days and kept in culture for up to one month. One day prior to the experiment the cells were split. Before the experiment, the cells were washed 3 times (1000 rpm, 6 min) with full medium. The cells were re-suspended and counted with the VI-cell counter (Beckman Coulter). Twenty thousand ($2 \times 10^4$) cells were added to each well of 96-well plate in 50 μl full medium containing heparin. Conditioned medium containing FGF wild type parent or variants at varying concentrations with heparin was added in an additional volume of 50 μl full medium to bring the final volume to 100 μl. The plate was incubated for 48 hours at 37° C. To assay cell proliferation, 100 μl of PMS reagent was added to 5 ml of XTT reagent and mixed thoroughly (according to manufacturer's protocol). Fifty micro-liters (50 μl) of the latter solution were added into each well, and the plates incubated at 37° C. for 4 hours and the color was read by a spectro-ELISA reader at $A_{490nm}$. In these experiments FDCP cells expressing FGFR4, FGFR3, FGFR2 or FGFR1 were grown in the presence of varying concentrations of the polypeptides of the invention.

Example 3

Effect of Variants on Growth Inhibition of RCS Chondrocytes

RCS is a rat chondrosarcoma derived cell line expressing preferentially high levels of FGFR2 and FGFR3 and low levels of FGFR1. In this cell line, FGFR functions as an inhibitor of cell proliferation similar to its expected role in the growth plate of the developing bone and in accord with the achondroplasia phenotype. In order to inhibit cell proliferation, the variants have to specifically induce FGFR signal transduction allowing the measuring of FGF affinity and specificity to the FGFRs reflected by the concentration dependence of induced growth inhibition.

The screening was performed on RCS cells in 96 well plates. Cells were seeded at a concentration of about 2,000 cells/well. The following day 10 ng/ml FGF or FGF variants and 5 μg/ml heparin were added to the cells. Positive and negative controls for cell proliferation were included in this assay at the same concentrations as the tested compounds. The Cy-Quant® assay kit was used to measure the amount of the cells. The results were measured in a fluoro ELISA reader.

Example 4

Chondrocyte Expansion

The effect of FGF-18 and FGF-18 variants on proliferation of articular chondrocytes was tested.

Articular Chondrocyte Culture:

Chondrocytes were isolated from human biopsies and cultured using the FGF variants of the present invention to identify the effect of the variants on proliferation and differentiation. The procedure employed for the isolation and propagation of articular chondrocytes is presented below.

Reagents:

Dulbecco's DMEM/F12 (Gibco BRL)

Fetal Bovine Serum (FBS) (Gibco BRL)

Streptomycin, Penicillin, Nystatin Solution (Biological Indus. Ltd.)

Trypsin-EDTA (Gibco BRL, cat. no. T8154) or Versene-Trypsin (Bio LAB Ltd.)

Isolation of Cells from Cartilage Biopsy:

A piece of cartilage tissue was minced into 2 to 4 mm pieces with a sterile scalpel. The collagenase solution was diluted 1:4 in FBS-DMEM, added to the tissue sample and left to incubate on a rotator at 37° C., overnight (ON). The cells were centrifuged (1200 rpm, 5-10 min). The medium was aspirated, the cells washed in 5 ml medium and re-centrifuged. The cells were re-suspended in culture medium and seeded in 25 cm$^2$ or 75 cm$^2$ flasks at a concentration of approximately 1×10$^6$ cells per flask. The cells were incubated in a 5% $CO_2$ incubator at 37° C. The cell medium was replaced every 2-3 days.

Procedure for Passaging Cells (Trypsinization):

When the cell culture reached the desired confluency, the medium was removed and the cells trypsinized in the following manner: One milliliter (1 ml) of the trypsin solution was added to a 25 cm$^2$ flask or 2.5 ml to a 75 cm$^2$ flask. The flask was gently shaken by hand for two seconds and the trypsin solution was immediately removed. Another 1 ml of trypsin was added to a 25 cm$^2$ flask or 2.5 ml to a 75 cm$^2$ flask. The flask was gently shaken by hand for ~30 seconds and left to incubate at 37° C. for 3-5 minutes. Verification that cells were detached was performed under the microscope. The trypsin was neutralized by adding FBS-DMEM; followed by addition of 10 ml to a 25 cm$^2$ flask and 25 ml to a 75 cm$^2$ flask. The cells were split to 2-3 new flasks and 20 ml fresh pre-warmed medium was added. The expansion of cells and trypsinization was performed as necessary.

Furthermore, the cell population grown on the above matrices expresses several of the chondrocyte differentiation markers. One of several phenotypes expressed during chondrocyte differentiation is glycosaminoglycan (GAG) production. The production of GAGs is identified in histological staining using Alcian blue and quantitated using the DMB (3,3'-dimethoxybenzidine dihydrochloride) dye method.

Proliferation of the cartilage cells in the presence of the different variants can be quantitated by cell counting, CyQUANT® (Molecular Probes) or XTT reagent (Biological Industries, Co.).

Example 5

Human Articular Chondrocytes: Isolation and Proliferation

Human articular chondrocytes were isolated from pieces of cartilage using digestion enzymes. Isolated primary chondrocytes were seeded in 75 cm$^2$ flasks (5×10$^4$ cells) containing DMEM/F12, 20% pooled human serum, 10 ng/ml of different FGF variants of the present invention and 5 µg/ml low molecular weight heparin (LMW). Cells were counted at different time points using the Vi-Cell XR.

Example 6

Human Articular Chondrocytes: In-Vitro Chondrogenesis Assay

The expanded chondrocytes were used for in-vitro chondrogenesis assay to produce high density pellet cultures. The pellet cultures were incubated for up to 21 days in chondrocytes differentiation medium containing DMEM, 10 ng/ml TGF-b, 100 nM dexamethasone, 0.28 mM ascorbic acid, 1 mM sodium pyruvate, 40 µg/ml proline, 10 µg/ml bovine insulin, 5.5 µg/ml human transferin, 5 µg/ml sodium selenite, 0.5 mg/ml bovine serum albumin and 1.7 µg/ml linoleic acid. Some pellet cultures were supplemented with FGF variant of the present invention or the FGF wt.

Example 7

Human Articular Chondrocytes: Histology Analysis of Pellet Cultures

Pellet cultures incubated for up to weeks in differentiation medium were fixed in PFA solution and paraffin blocks were prepared. Sections were used for analysis of proteoglycans by Alcian blue (AB) and Safranin O (SO) stains.

Example 8

Cell Proliferation of Primary Porcine Chondrocytes

Primary porcine chondrocytes were harvested from articular cartilage of adult pig using overnight collagenase:pronase digestion. The cells were seeded in 6-well plate (300,000/well) that was pre-coated with 200 ug/ml plasma fibrinogen in DMEM-F12 for 1 hr at 370 C. The cells were cultured in 2 ml/well DMEM-F12+2% FBS+100 ug/ml ascorbic acid+ITS-1 (1:100)+pen-strep. The variants (100 ng/ml) were added the next day. The media were replaced with fresh variants 3 days later. The cells were harvested at day 5 and counted.

Example 9

Chondrocyte Differentiation

Cartilage taken from osteoarthritis patients was dissected and pre-incubated for 3 days in control medium (day 0) followed by 4 days in the presence of 50 ng/ml of different FGFs. Cell supernatant was collected and levels of secreted glycosaminoglycans (sGAGs) were determined.

Example 10

In-Vivo Studies in a Mouse Model of Injury-Induced Osteoarthritis

The beneficial effects of the FGF-18 variants of the present invention are evaluated in a mouse model of injury-induced osteoarthritis using intra-articular injections. Specifically, the variants of the present invention are compared to wild type FGF-18 in terms of their efficacy. An evaluation of the possible side effects is also performed. Three groups, each containing 6 mice, are tested. Group 1. carrier (0.5% hyaluronic acid); Group 2. FGF-18 wild type (0.1 µg)+carrier; and Group 3. FGF-18 variant of the present invention (0.1 µg)+carrier. The injections are administered bi-weekly for a period of 3 weeks. The FGFs are administered in sterile PBS and a sterile solution of 2× concentrated carrier solution (1% hyaluronic acid (HA; MW=1.5×10⁶ Da)).

Experimental osteoarthritis is induced by transsection of the medial anterior meniscotibial ligament which causes destabilization of the medial meniscus (DMM). The DMM model was developed by Glasson et al (Osteoarthritis Cartilage. 2007; 15:1061-9). Briefly, mice are anesthetized, hair is removed from the skin of the right knee joint and an incision is made in the skin medial from the patellar ligament. Subsequently, an incision is made in the joint capsule, again medial from the patellar ligament. The joint is opened and suppatellar fat is removed. The ligament is identified and transected. After verifying that all bleeding into the joint has stopped, the joint is flushed with excess saline and the joint capsule is closed with 3 sutures (resorbable). Finally, the skin is closed using 1 suture (resorbable) and tissue adhesive. The mice are housed in groups of 5-6 animals and 8 weeks after surgery full blown osteoarthritis pathology is present and knee joints are isolated for histology.

Treatment with various formulations is initiated 3-4 weeks post surgery. Immediately prior to injection, sterile solution of 2× carrier solution (1% hyaluronic acid) is mixed with an equal volume of sterile PBS containing the various FGF ligands at concentration that yields amounts of 0.1 μg or 0.5 μg of ligand per injection. Final dilution before injection is performed by diluting the ligands with equal volume of 2× carrier solution. The final volume of injection is 6-10 μl per animal. Animals receive bi-weekly intra-articular injections for 3 consecutive weeks (a total of 6 injections).

Evaluation is performed at 8 weeks post surgery using both H&E and proteoglycan staining (e.g. toluidine blue, saffranin-O).

Mouse strain: C57Bl/6 (12 weeks old, 25-30 g)

Group size: 6 animals

Osteoarthritis model: DMM

Housing: 6 mice per cage with wood chip bedding

Conditions: Mice are acclimatized after arrival for at least 2 weeks

Food/water: Food and acidified water ad libitum

Scoring of the osteoarthritis by histology is performed as follows: osteoarthritis joints are fixed in formalin for 3 days, followed by decalcification for 1 week and embedding in paraffin. All joints are sectioned semi-serial: coronal plane, 7 μm whole knee joint sections. Staining by Fast Green/Saffranin 0. Scoring of osteoarthritis cartilage damage is performed following an advanced version of the murine OARSI score, at 4 locations (med and lat femur; med and lat tibia). Extra scores which are further included are synovial inflammation, osteophyte formation and subchondral bone changes.

Results:

FGF-18 and the N-terminal truncated variants (FGF-18$^{\Delta37}$, FGF-18$^{\Delta45}$ and FGF-18$^{\Delta51}$) were tested for receptor specificity by binding to immobilized extracellular domain of FGFR1-4 (FIG. 2). Biotinylated FGF's were added at increasing concentrations to FGFR1-4 anchored to a MaxiSorp ELISA plate. Bound ligands were detected by HRP-streptavidin. While FGF-18 wild type activates FGFR1-4, the FGF-18 truncated variants of the present invention do not activate FGFR1-2 while maintaining the activation toward FGFR3-4 (Table 2). The variants of the present invention are thus shown to be specific for FGFR3-4.

TABLE 2

EC$_{50}$ scores of biotinylated FGF ligands in immobilized receptor assay of FDCPR1-4-Fc.

| EC$_{50}$ (ng/ml) | R1 | R2 | R3 | R4 |
| --- | --- | --- | --- | --- |
| F18 | 28.21 | 9.51 | 5.04 | 9.23 |
| F18Δ37 | — | — | 5.94 | 5.86 |
| F18Δ45 | — | — | 9.16 | 8.10 |
| F18Δ51 | — | — | 10.21 | 9.93 |

Figure 2A:
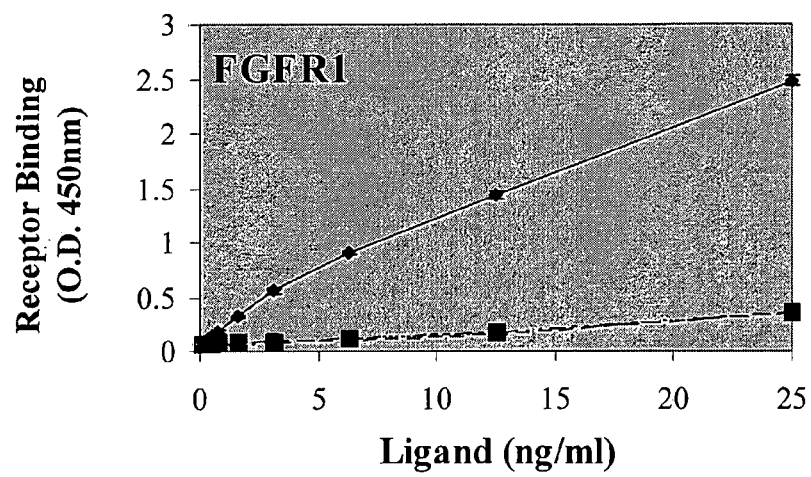
FIGS. 2A-2D. Immobilized receptor binding assay analysis of FGF-18 variants demonstrating FGF receptor specificity. (2A) FGFR1; (2B) FGFR2; (2C) FGFR3 and (2D) FGFR4. Biotinylated FGF-18 (♦) and three FGF-18 variants (Δ37, v1, (●); Δ45, v2, (■); and Δ51, v3, (■)) were added at increasing concentrations to FGFR1-4 anchored to a Max- iSorp ELISA plate. Bound ligands were detected by HRP-streptavidin. Data are the average of duplicate wells.
Figure 2B:
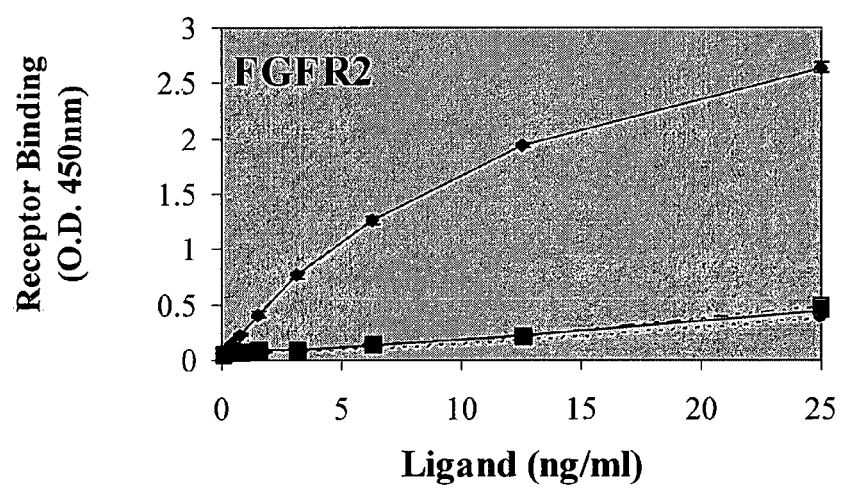
Figure 2C:
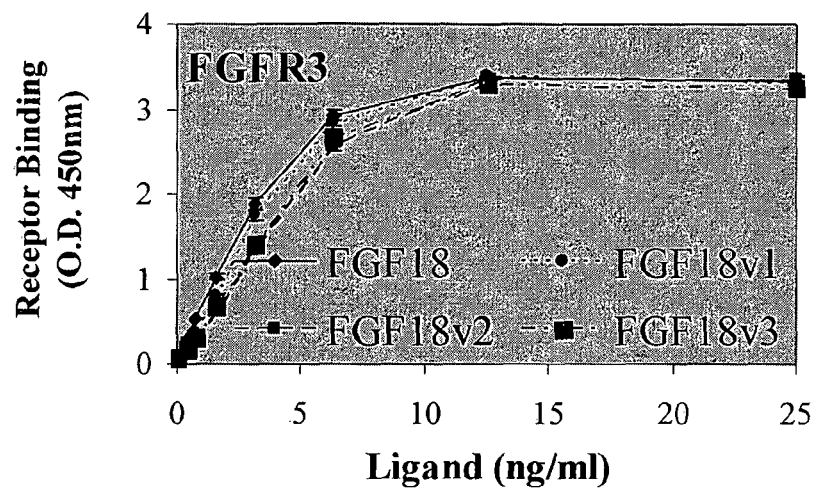
Figure 2D:
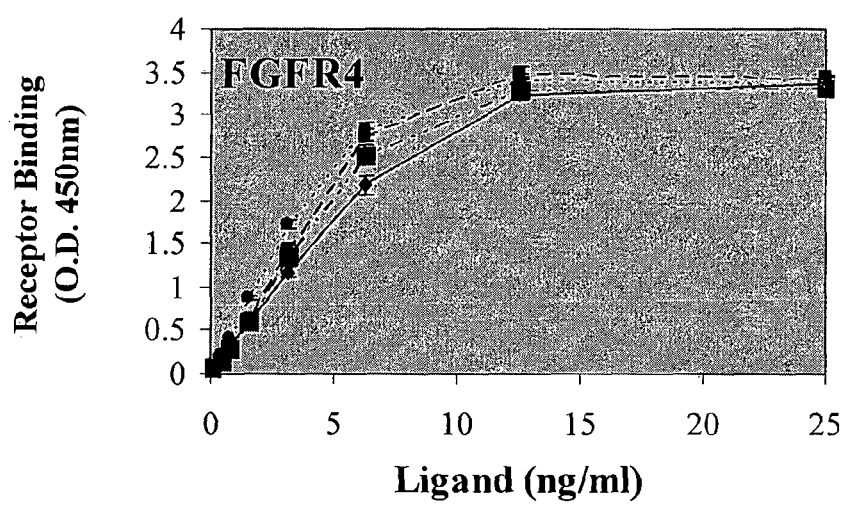
Figure 3:
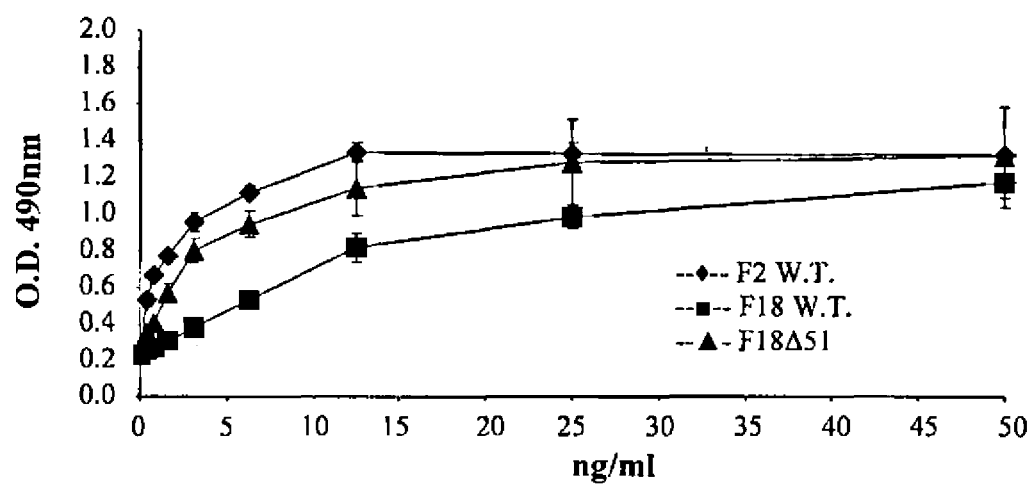
FIG. 3. Effect of FGF-18$^{\Delta 51}$ on cells proliferation of FDCPR3. FGF-18$^{\Delta 51}$ (▲) effect on FDCPFGFR3 cell proliferation was compared to that of FGF-2 (♦) or FGF-18 wild type ligands (■). Each of the three ligands was added to FDCPFGFR3 cells at different concentrations (100 ng/ml→0.39 ng/ml). After two days incubation at 37° C., cell proliferation was measured by the XXT reagent kit.
Figure 4:
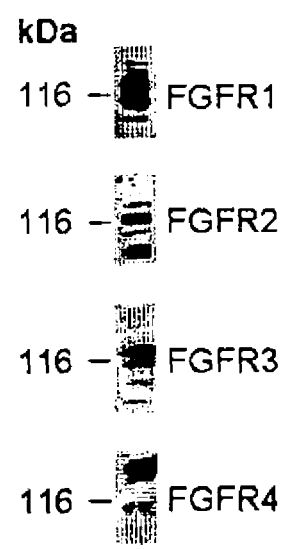
FIG. 4. Expression of FGFRs in primary chondrocytes. Primary chondrocytes were lyzed and probed by Western with anti-FGFRs antibodies. The receptors were detected by ECL.

To further explore the receptor binding specificity of these variants, their biological activity in a receptor dependent cell based FDCP assay was examined (FIG. 3). Table 3 summaries the EC$_{50}$ scores of FGF-2 wild type, FGF-18 wild type, FGF-18$^{\Delta37}$, FGF-18$^{\Delta45}$ and FGF-18$^{\Delta51}$ ligands used. Primary chondrocytes harbor multiple FGFRs (FIG. 4) and respond to various FGFs by proliferation or differentiation depending on their differentiation state and expressed receptor profile. Activation of FGFR1 and FGFR2 usually leads to cell division and prolifreration while FGFR3 signaling typically results in chondrocyte differentiation, maturation and matrix deposition.

TABLE 3

EC$_{50}$ scores of FGF ligands in cell proliferation of FDCPR3.

| Ligand | EC50 (ng/ml) |
| --- | --- |
| F18 w.t. | 15.40 |
| F18Δ37 | 3.14 |
| F18Δ45 | 5.44 |
| F18Δ51 | 3.97 |
| F2 w.t. | 1.19 |

Figure 5:
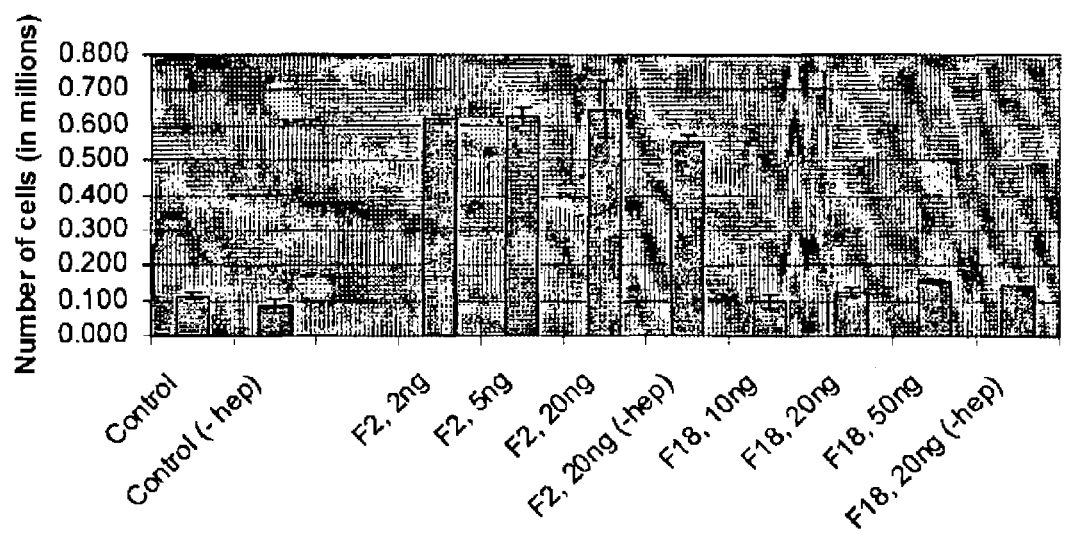
FIG. 5. Effect of FGF-2 (F2) and FGF-18 (F18) on PAC proliferation. Human primary articular chondrocytes (PAC), passage 1, were seeded in 12 well plate (10,000 cells/well) in DMEM-F12+10% FBS. Ligands (FGFs) were added with 5 μg/ml heparin (where indicated) and cells proliferation was determined using an automated cell counter.
Figure 6:
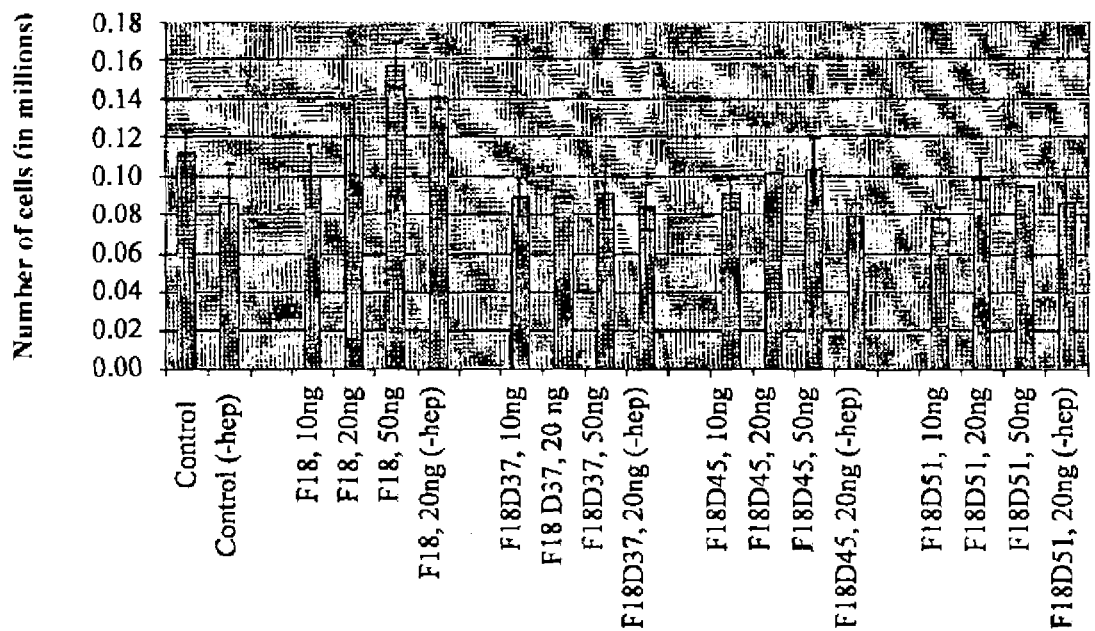
FIG. 6. Effect of low doses of FGF-18 and FGF-18 variants on PAC Proliferation. Human primary articular chondrocytes (PAC), passage 1, were seeded in 12 well plate (10,000 cells/well) in DMEM-F12+10% FBS. Ligands (FGFs) were added the next day and the cells were grown for four days without further medium exchanges. Heparin was used at 5 μg/ml final concentration. Cells were harvested by trypsinization and counted using an automated cell counter.

FGF-18 was further compared to FGF-2 wild type, a ligand that preferentially binds and activates FGFR1 and FGFR2, for its proliferative effect on young primary articular chondrocytes (PAC). FGF-18 was found to be approximately 5 folds less active than FGF-2 (both at 20 ng/ml, FIG. 5) in activating PAC. In a subsequent experiment, FGF-18 and the N-terminal variants of the present invention were tested for their proliferative effect on the same cells. While FGF-18 wild type treatment led to approximately 1.5 folds increase in PAC proliferation as compared to the control, FGF-18 truncated variants showed no detectable effect on chondrocytes cell proliferation (FIG. 6).

Figure 7:
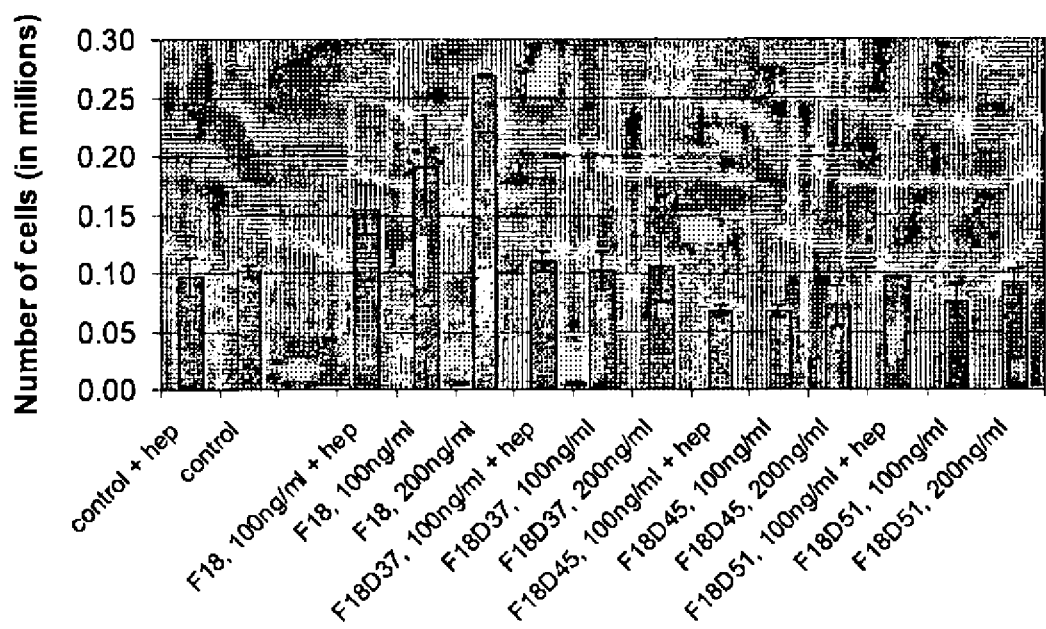
FIG. 7. Effect of high doses of FGF-18 and FGF-18 variants on PAC Proliferation. Human primary articular chondrocytes (PAC), passage 3, were seeded in 24 well plate (7,000 cells/well) in DMEM-F12+10% FBS. Ligands (FGFs) were added the next day to cells and cells were grown for one week without further medium change. Heparin was used at 5 μg/ml final concentration. Cells were harvested by trypsinization and counted using an automated cell counter.

In order to further explore the proliferative capacity of FGF-18 and its FGFR3 specific variants, FGF-18 wild type and FGF-18$^{\Delta51}$ were tested at very high doses of up to 200 ng/ml. Remarkably, even at 200 ng/ml, FGF-18 was not saturable with approximately 2.5 folds increase in PAC as compared to un-treated cells, suggesting an extremely low affinity of this ligand to its receptors at the conditions tested. At all concentrations used, FGF-18$^{\Delta51}$ had no proliferative activity. Thus, the FGF N-terminal truncated variants of the present invention are highly selective to FGFR3 and show lack of a proliferative response via FGFR3 in primary chondrocytes (FIG. 7).

Figure 8:
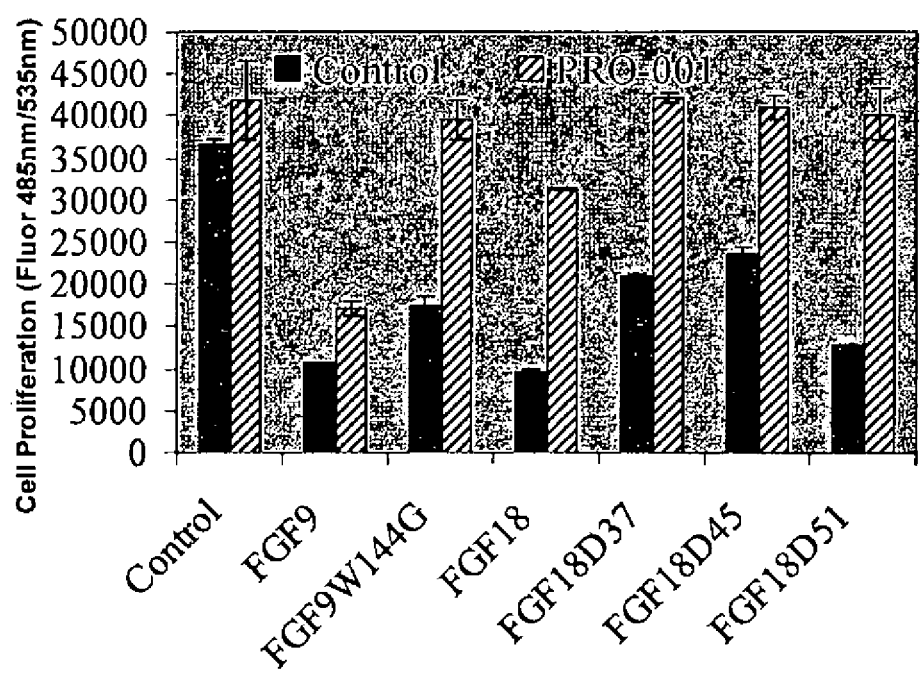
FIG. 8. FGF-18 N-terminal variants inhibit RCS cell proliferation in a receptor specific manner. RCS cells were treated with wild-type or mutant FGFs with or without the anti-FGFR3 PRO-001 (WO 07/144,893) antibody for 3 days. Then, cell proliferation was measured by the CyQuant analysis. Untreated cells were included as control.

Rat chondrosarcoma (RCS) cell line is a unique chondrocyte derived cell type representing a mature prehypertrophic chondrocyte that responds to FGF signaling by growth arrest in the G1 phase of the cell cycle (Aikawa et al., J. Biol. Chem., 2001, Vol. 276, p. 29347). Addition of FGF-9 or FGF-18 to RCS cells resulted in a complete block of cell proliferation (FIG. 8). Addition of N-terminal truncated FGF-18 variants also inhibited RCS cell proliferation yet to a lesser extent. Incubation of RCS cells with PRO-001 (WO 07/144,893), a potent and highly specific anti-FGFR3 antibody partially reversed the inhibitory action of FGF-9 yet completely restored cell proliferation in the presence of the receptor specific FGF9W144G ligand (WO 02/36732). Likewise, PRO-001 moderately reversed the action of wild-type FGF-18 and completely reversed the action of FGF-18 N-terminal variants suggesting that the wild-type FGF-18 activates in addition to FGFR3 other FGFRs while the N-terminal variants are FGFR3 specific.

Figure 9A:
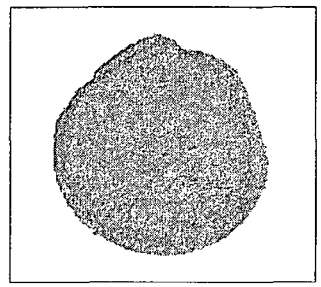
FIGS. 9A-9C. Effect of FGF-18 wild type or FGF-18$^{\Delta 51}$ treatment on chondrocytes' pellet culture formation. (9A) control; (9B) FGF-18 wild type; and (9C) FGF-18$^{\Delta 51}$. Human articular chondrocytes (passage 1, d11, 0.5*10$^6$/pellet) were grown in chondrocyte differentiation medium for 2 weeks. Some pellets were supplemented with 15 ng/ml of FGF-18 wild type (wt) or FGF-18$^{\Delta 51}$. Media was changed every 3 days. At the end of the experiment, pellets were fixed for histology. H&E stain of X40 magnification of representative pellets is presented.
Figure 9B:
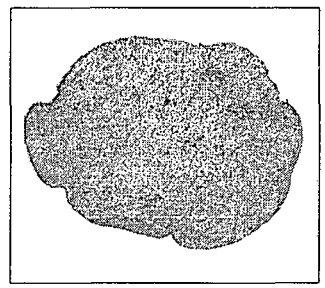
Figure 9C:
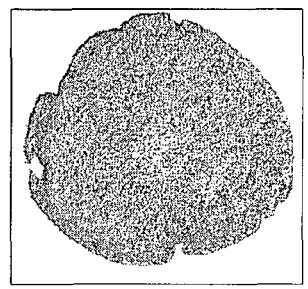

The effect of FGF-18 wild type and FGF-18$^{\Delta 51}$ on chondrocytes' pellet culture formation is shown in FIG. 9. The ligands provided an increase in mass culture of PAC.

To further delineate the location of receptor specificity, FGF-18 variants lacking 31 or 33 amino acids from the N-terminus (FGF-18$^{\Delta 31}$ and FGF-18$^{\Delta 33}$, respectively) were tested using functional ELISA. While FGF-18$^{\Delta 33}$ did not bind FGFR2 and FGFR1, FGF-18$^{\Delta 31}$ recognized all 4 receptors similar to wild-type FGF-18. Table 4 indicates the EC$_{50}$ of the different N-terminal FGF-18 variants to each FGF receptor.

TABLE 4

EC$_{50}$ scores of the indicated variants to each receptor type using functional ELISA.

| | EC$_{50}$ (ng/ml) | | | |
|---|---|---|---|---|
| | FGFR1 | FGFR2 | FGFR3 | FGFR4 |
| FGF18 WT | 22.80 | 8.76 | 6.59 | 10.21 |
| FGF18Δ31 | 24.38 | 11.22 | 8.55 | 9.36 |
| FGF18Δ33 | ND | ND | 8.27 | 7.11 |
| FGF18Δ37 | ND | ND | 9.75 | 8.28 |
| FGF18Δ51 | 41.94 | 43.47 | 9.99 | 10.62 |

ND—Not Detected

Figure 10:
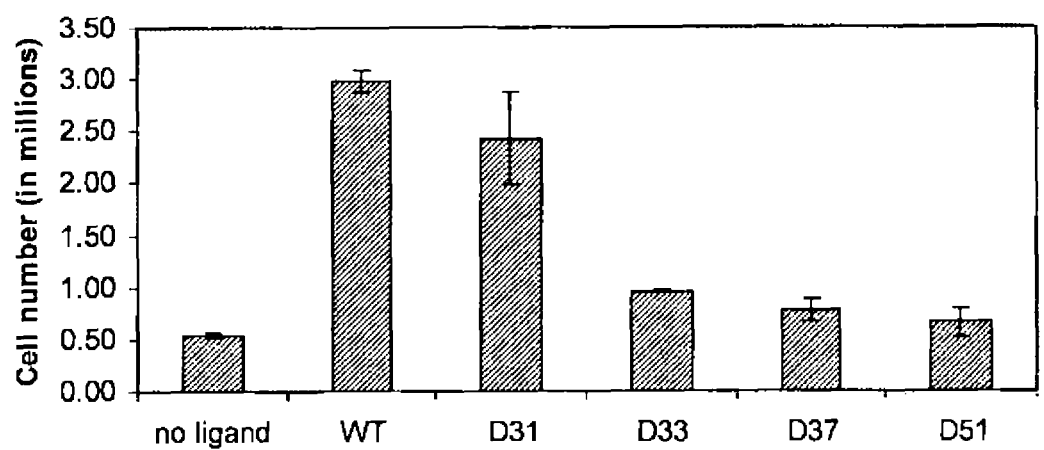
FIG. 10. Effect of FGF-18 N-terminal variants on chondrocyte proliferation. Primary porcine chondrocytes were harvested from articular cartilage of adult pig. 300,000 cells were seeded per well. The ligands were added the next day at 100 ng/ml, followed by media replacement 3 days later. The cells were harvested at day 5 and counted.

The mitogenic activity of FGF-18$^{\Delta 31}$ and FGF-18$^{\Delta 33}$ was further compared to the mitogenic activity of FGF-18$^{\Delta 37}$, FGF-18$^{\Delta 51}$ and wild-type FGF-18 in primary porcine chondrocytes. FGF-18$^{\Delta 33}$ did not induce proliferation while FGF-18$^{\Delta 31}$ demonstrated comparable mitogenic activity with that of the wild-type FGF-18 (FIG. 10). Without being bound by any theory or mechanism of action, the receptor binding activity as well as the mitogenic activity results imply that amino acids residues 32-37 of FGF-18 are important for binding and activation of FGFR1 and FGFR2 by FGF-18.

Figure 11:
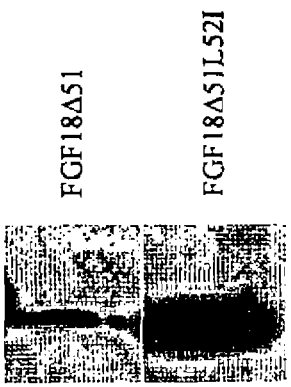
FIG. 11. FGF-18$^{\Delta 51 L 52 I}$ is expressed at higher levels than FGF-18$^{\Delta 51}$. FGF-18$^{\Delta 51}$ and FGF-18$^{\Delta 51 L 52 I}$ transformed BL21(DE3) bacteria were cultured overnight. Overnight lysates were analyzed by Western blotting with anti-FGF-18 antibody.
Figure 12A:
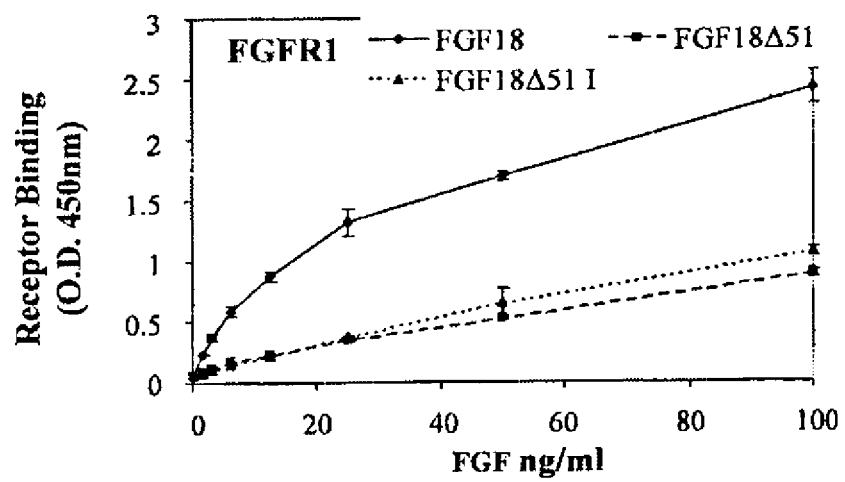
FIGS. 12A-12D. FGF-18$^{\Delta 51 L 52 I}$ receptor specificity. (12A) FGFR1; (12B) FGFR2; (12C) FGFR3; and (12D) FGFR4. FGFRs were anchored to a MaxiSorp plate. Biotinylated FGF ligands (FGF-18 wild type (♦); FGF-18$^{\Delta 51}$ (■)
Figure 12B:
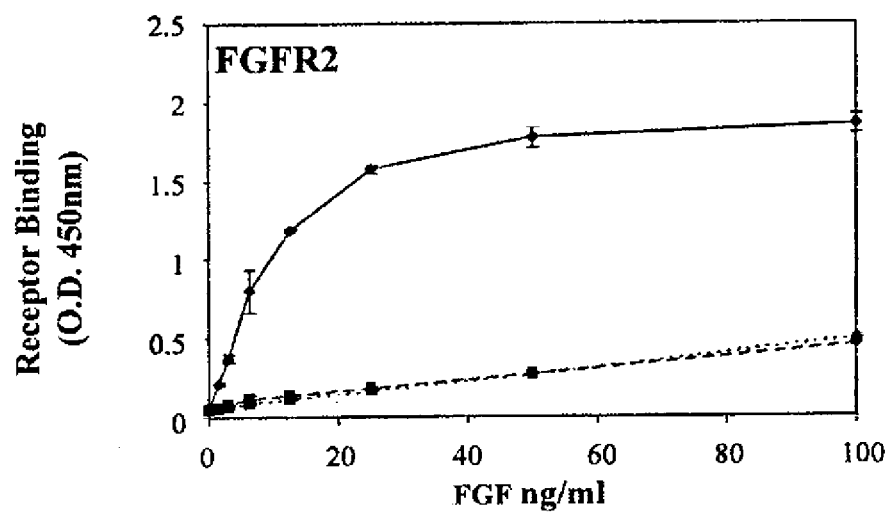
Figure 12C:
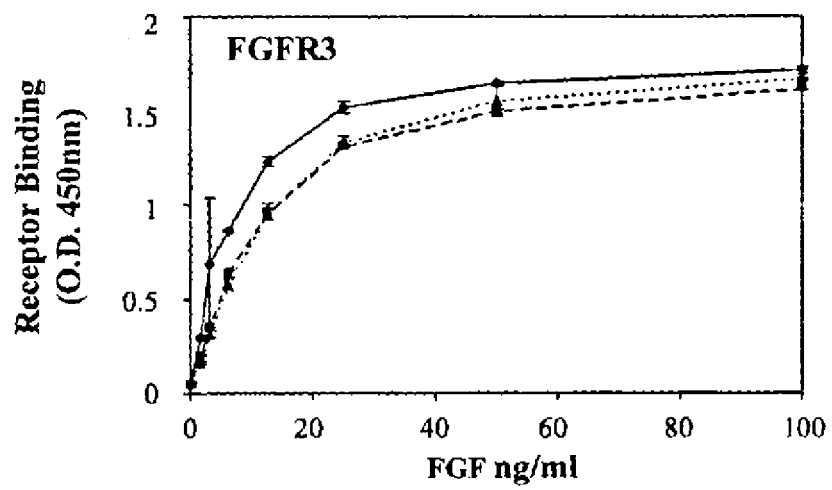
Figure 12D:
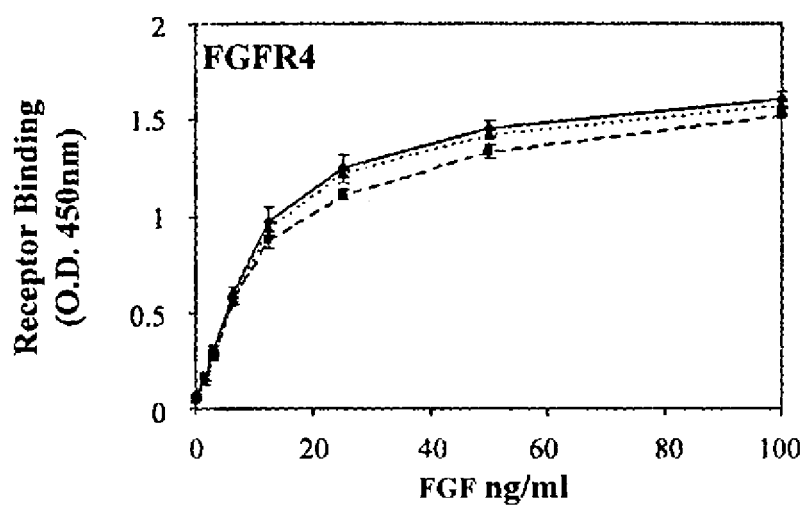

Another FGF-18 N-terminal truncated variant (451) which further comprises a conservative substitution at the penultimate leucine (L52) with isoleucine denoted FGF-18$^{\Delta 51L52I}$ (also denoted as FGF-18$^{\Delta 51I}$) was produced. BL21 DE3 bacteria were transformed with pET-FGF-18$^{\Delta 51L52I}$ and the expression level was compared to that of pET-FGF-18$^{\Delta 51}$. Western immunoblot analysis demonstrated a significant increase in protein level of FGF-18$^{\Delta 51L52I}$ (FIG. 11). The specificity of FGF-18$^{\Delta 51L52I}$ was then compared to that of FGF-18$^{\Delta 51}$ by functional ELISA. FIG. 12 shows that FGF-18$^{\Delta 51L52I}$ retained the same receptor specificity as FGF-18$^{\Delta 51}$. In order to evaluate the biological activity of FGF-18$^{\Delta 51L52I}$, the variant was added to FDCP-FGFR3 cells and cell proliferation was compared to that induced by FGF-18$^{\Delta 51}$ and wild-type FGF-18. FGF-18$^{\Delta 51L52I}$ and FGF-18$^{\Delta 51}$ were both superior to the wild-type FGF-18 (FIG. 13).

Next, the effect of FGF-18$^{\Delta 51L52I}$ on chondrocyte differentiation was examined. FGFs induced GAG secretion and FGF-18$^{\Delta 51L52I}$ was at least as potent as wild-type FGF-18 (FIG. 14). FGF-18$^{\Delta 37}$ induced GAG synthesis most effectively.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. An isolated FGF-18 polypeptide having a 50 amino acid N-terminal truncation with the Gln51 replaced by a Met residue, the isolated FGF-18 polypeptide comprising an amino acid sequence selected from the group consisting of SEQ ID NO: 47, SEQ ID NO: 67, and SEQ ID NO: 69, and having increased receptor selectivity when compared to an isolated wild-type FGF-18 polypeptide by a gain of activity by at least a factor of two toward FGFR3 but not toward all FGFR subtypes.

2. The isolated FGF-18 polypeptide according to claim 1, wherein the isolated FGF-18 polypeptide comprises the amino acid sequence of SEQ ID NO: 47.

3. The isolated FGF-18 polypeptide according to claim 1, wherein the isolated FGF-18 polypeptide comprises the amino acid sequence of SEQ ID NO: 67.

4. The isolated FGF-18 polypeptide according to claim 1, wherein the isolated FGF-18 polypeptide comprises the amino acid sequence of SEQ ID NO: 69.

5. A pharmaceutical composition comprising as an active ingredient at least one isolated FGF-18 polypeptide having a 50 amino acid N-terminal truncation with the Gln51 replaced by a Met residue, the isolated FGF-18 polypeptide comprising an amino acid sequence selected from the group consisting of SEQ ID NO: 47, SEQ ID NO: 67, and SEQ ID NO: 69, and having increased receptor selectivity when compared to an isolated wild-type FGF-18 polypeptide by a gain of activity by at least a factor of two toward FGFR3 but not toward all FGFR subtypes.

6. The pharmaceutical composition of claim 5, further comprising at least one bioactive agent.

7. The pharmaceutical composition according to claim 6, wherein the at least one bioactive agent is a carboxylated polysaccharide.

8. The pharmaceutical composition according to claim 7, wherein the carboxylated polysaccharide is hyaluronic acid.

9. The pharmaceutical composition according to claim 6, wherein the at least one bioactive agent is a C-type natriuretic peptide.

10. A method of inducing cartilage repair comprising the step of administering to an individual in need thereof a pharmaceutical composition according to claim 5.

11. A method of inducing cartilage repair in an individual with a degenerative joint disease comprising the step of administering to an individual in need thereof a pharmaceutical composition according to claim 5.

12. The method according to claim 11, wherein the degenerative joint disease is osteoarthritis.

13. The pharmaceutical composition of claim 5, wherein the isolated FGF-18 polypeptide comprises the amino acid sequence of SEQ ID NO: 47.

14. The pharmaceutical composition of claim 5, wherein the isolated FGF-18 polypeptide comprises an amino acid sequence selected from the group consisting of SEQ ID NO: 67 and SEQ ID NO: 69.

15. A pharmaceutical composition comprising as an active ingredient at least one isolated polynucleotide encoding an FGF-18 polypeptide having a 50 amino acid N-terminal truncation with the Gln51 replaced by a Met residue, the polypeptide comprising an amino acid sequence selected from the group consisting of SEQ ID NO: 47, SEQ ID NO: 67, and SEQ ID NO: 69, and having increased receptor selectivity when compared to an isolated wild-type FGF-18 polypeptide by a gain of activity by at least a factor of two toward FGFR3 but not toward all FGFR subtypes.

16. A method of inducing cartilage repair comprising the step of administering to an individual in need thereof a pharmaceutical composition according to claim 15.

17. A method of inducing cartilage repair in an individual with a degenerative joint disease comprising the step of administering to an individual in need thereof a pharmaceutical composition according to claim 15.

18. An isolated FGF-18 polypeptide having a 50 amino acid N-terminal truncation with the Gln51 replaced by a Met residue and the Leu52 replaced by an amino acid residue other than leucine, the isolated FGF-18 polypeptide comprising an amino acid sequence selected from the group consisting of SEQ ID NO: 67 and SEQ ID NO: 69, and having increased receptor selectivity when compared to an isolated wild-type FGF-18 polypeptide by a gain of activity by at least a factor of two toward FGFR3 but not toward all FGFR subtypes.

19. The polypeptide according to claim 18, wherein the Leu52 is replaced by an amino acid residue selected from isoleucine, valine and methionine and wherein said polypeptide has the amino acid sequence of SEQ ID NO: 67.

20. The polypeptide according to claim 19, wherein the Leu52 is replaced by isoleucine, and wherein said polypeptide has the amino acid sequence of SEQ ID NO: 69.

* * * * *